(12) United States Patent
Anderson et al.

(10) Patent No.: US 7,544,861 B2
(45) Date of Patent: *Jun. 9, 2009

(54) DEFENSIN-ENCODING NUCLEIC ACID MOLECULES, USES THEREFOR AND TRANSGENIC PLANTS COMPRISING SAME

(75) Inventors: Marilyn Anne Anderson, Keilor (AU); Fung Tso Lay, Reservoir (AU); Robyn Louise Heath, Clifton Hill (AU)

(73) Assignee: Hexima Limited, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/372,761

(22) Filed: Mar. 10, 2006

(65) Prior Publication Data

US 2006/0156433 A1     Jul. 13, 2006

Related U.S. Application Data

(60) Division of application No. 11/062,999, filed on Feb. 22, 2005, now Pat. No. 7,297,840, which is a continuation of application No. 10/072,809, filed on Feb. 8, 2002, now Pat. No. 7,041,877.

(60) Provisional application No. 60/267,271, filed on Feb. 8, 2001.

(51) Int. Cl.
*A01H 5/00* (2006.01)
*C12N 15/29* (2006.01)
*C12N 15/82* (2006.01)

(52) U.S. Cl. ...................... 800/298; 536/23.6
(58) Field of Classification Search ........................ None
See application file for complete search history.

(56) References Cited

U.S. PATENT DOCUMENTS 7,041,877 B2 *   5/2006   Anderson et al. ........... 800/301
7,297,840 B2 *  11/2007   Anderson et al. ........... 800/302

FOREIGN PATENT DOCUMENTS

WO      WO 93/04586     *  3/1993

OTHER PUBLICATIONS

Gu et al, 1992, Mol. Gen. Genet. 234:89-96.*
Yamada et al (1999, GenBank Accession No AB005266).*
Anderson et al. (May 1989) "Sequence Variability of Three Alleles of the Self-Incompatibility Gene of Nicotiana alata," Plant Cell 1:483-491.
Anderson et al. (1987) "Immuno-Gold Localization of α-L-arabinofuranosyl Residues in Pollen Tubes of Nicotiana alata Link et Otto," Planta 171:438-442.
Atkinson et al. (Feb. 1993) "Proteinase Inhibitors in Nicotiana alata Stigmas are Derived from a Precursor Protein Which is Processed into Five Homologous Inhibitors," Plant Cell 5:203-213.
Bloch and Richardson (Feb. 1991) "A New Family of Small (5 kDa) Protein Inhibitors of Insect Alpha-Amylases From Seeds or Sorghum (Sorghum bicolor (L) Moench) have Sequence Homologies with Wheat Gamma-Purothionins" FEBS Lett. 279(1):101-104.
Broekaert et al. (1990) "An Automated Quantitative Assay for Fungal Growth Inhibition" FEMS Microbiol. Lett. 69:55-60.
Chiang and Hadwiger (1991) "The Fusarium solani-Induced Expression of a Pea Gene Family Encoding High Cysteine Content Proteins" Mol. Plant-Mircobe. Interact. 4(4):324-331.
Choi et al. (1993) "Nucleotide Sequence of a cDNA Encoding a Low Molecular Weight Sulfur-Rich Protein in Soybean Seeds" Plant Physiol. 101:699.
Choi et al. (1995) "Tissue-specific and Developmental Regulation of a Gene Encoding a Low Molecular Weight Sulfur-rich Protein In Soybean Seeds" Mol. Gen. Genet 246:266-268.
Colilla et al. (Sep. 1990) "Gamma-Purothionins: Amino Acid Sequence of Two Polypeptides of a New Family of Thionins from Wheat Endosperm" FEBS Lett. 270(1-2):191-194.
Drews et al. (Jun. 1991) "Negative Regulation of the Arabidopsis Homeotic Gene AGAMOUS by the APETALA2 Product" Cell 65:991-1002.
Fant et al. (1994) "The Solution Structure by 1H NMR of a Plant Antifungal Protein from Radish Seeds (Rs-AFP1)" In: LP Ingman, J. Jokissaari, J. Lounila (eds), Abstracts of the 12th European Expereimental NMR Conference p. 247.
Gao et al. (Dec. 2000) "Fungal Pathogen Protection in Potato by Expression of a Plant Defensin Peptide," Nat. Biotechnol. 18:1307-1310.
Gu et al. (1992) "A Flower-Specific cDNA Encoding a Novel Thionin in Tobacco" Mol. Gen. Genet. 234:89-96.
Heath et al. (1997) "Proteinase Inhibitors from Nicotiana alata Enhance Plant Resistance to Insect Pests" J. Insect Physiol. 43(9):833-842.
Ishibashi et al. (1990) "Stored mRNA in Cotyledons of Vigna unguiculata Seeds: Nucleotide Sequence of Cloned cNDA for a Stored mRNA and Induction of its Synthesis by Precocious Germination" Plant Mol. Biol. 15:59-64.
Karunanadaa et al. (1994) "Characterization of a Predominantly Pistil-Expressed Gene Encoding a Gamma-Thionin-Like Protein of Petunia inflata" Plant Mol. Biol. 26:459-464.
Komori et al. (Dec. 15, 1998) "Gamma-Thionin 1 Precursor," EMBL Accession No. O24115.
Laemmli (Aug. 1970) "Cleavage of Structural Proteins During the Assembly of the Head of Bacteriophase T4" Nature 227:680-685.
Lay et al. (2000) "Strucutre and Function of a Floral Defensin From Nicotiana alata," COMBIO Conference, New Zealand.

(Continued)

*Primary Examiner*—Anne R Kubelik
(74) *Attorney, Agent, or Firm*—Greenlee, Winner and Sullivan, P.C.

(57) ABSTRACT

The present invention provides nucleic acid molecules derived from *Nicotiana alata*, which encode defensin-like molecules. The present invention contemplates the use of such nucleic acid molecules in the generation of transgenic plants having resistance or at least reduced sensitivity to plant pests including insects, microorganisms, fungi and/or viruses. The transgenic plants provided by the present invention include monocotyledonous and dicotyledonous plants, and particularly include crop plants and ornamental flowering plants.

16 Claims, 18 Drawing Sheets

OTHER PUBLICATIONS

Lay et al. (2000) "Structure and Function of a Floral Defensin From Nicotiana alata," FAOBMB Conference, Beijing. China.

Lay et al. (2000) "Structural Characterisation of a Flower-Specific Defensin," LORNE Conference, Melbourne, Australia.

Lay et al. (1999) "A Tail of a Floral Defensin from Nicotiana alata," COMBIO Conference, Goldcoast, Australia.

Lay et al. (1998) "Characterization of an Antifungal Defensin Protein from Nicotiana alata," ASBMB Conference, Adelaide, Australia.

Lay et al. (1998) "Temporal and Spatial Characterisation of a Predominantly Flower Specific Defensin-Like Protein from Nicotiana alata," LORNE Conference, Melbourne, Australia.

Lay et al. (1997) "Isolation and Characterisation of a Flower Specific Defensin-Like Protein from the Flowers of Nicotiana alata," ASBMB Conference, Melbourne, Australia.

Li and Gray (Aug. 1999) "Molecular Characterization of a cDNA, NTS 13, Encoding a Defensin-Like Protein in Tobacco Styles," (Accession No. X99403) Plant Gene Register PGR 99-071 Plant Physiol. 120:633.

Mendez et al. (1990) "Primary Structure and Inhibition of Protein Synthesis in eukaryotic Cell-free System of a Novel Thionin, Gamma-hordothionin, from Barley Endosperm" Eur. J. Biochem. 194:533-539.

Milligan et al. (1995) "Nature and Regulation of Pistil-Expressed Genes in Tomato," Plant Mol. Biol. 28:691-711.

Moreno et al. (1994) "Pseudothionin-St1, a Potato Peptide Active Against Potato Pathogens" Eur. J. Biochem 223:135-139.

Neumann et al. (1996) "Purification and Mass Spectrometry-based Sequencing of Yellow Mustard (Sinapis alba L.) 6 kDa Proteins" Int. J. Peptide Protein Res. 47:437-446.

Nitti et al. (1995) "Amino Acid Sequence and Disulphide-Bridge Pattern of Three Gamma-Thionins from Sorghum bicolor" Eur. J. Biochem. 228:250-256.

Osborn et al. (1995) "Isolation and Characterisation of Plant Defensins from Seeds of Asteraceae, Fabaceae. Hippocastanaceae and Saxifragaceae" FEBS Lett. 368:257-262.

Ozaki et al. (1980) "Amino Acid Sequence of a Purothionin Homolog from Barley Flour" J. Biochem. 87(2):549-555.

Romero et al. (1997) "Processing of Thionin Precursors in Barley Leaves by a Vacuolar Proteinase," Eur. J. Biochem. 243:202-208.

Schultz et al. (1997) "Molecular Characterisation of a cDNA Sequence Encoding the Backbone of a Style-Specific 120 kDa Glycoprotein Which has Features of Both Extensins and Arabinogalactan Proteins" Plant Mol. Biol. 35:833-845.

Stiekema et al. (1988) "Molecular Cloning and Analysis of Four Potato Tuber mRNAs" Plant Mol. Biol. 11:255-269.

Terras et al. (Aug. 1992) "Analysis of Two Novel Classes of Plant Antifungal Proteins from Radish (Raphanus sativus L.) Seeds" Journal of Biological Chem. 267(22):15301-15309.

Terras et al. (Feb. 1993) "A New Family of Basic Cysteine-Rich Plant Antifungal Proteins From Brassicaceae Species" FEBS Letters 316(3):233-240.

Terras et al. (May 1995) "Small Cysteine-Rich Antifungal Proteins from Radish: their Role in Host Defense" Plant Cell 7:573-588.

Yamada, S. (Jul. 6, 1997) "Nicotiana Excelsior mRNA for Gamma-Thionin, Complete cds," EMBL Accession No. AB005266.

Yamada et al. (1997) "cDNA Cloning of Gamma-Thionin from Nicotiana excelsior" Accession No. AB005266 Plant Physiol. 115:314.

Yu et al. (2000) Direct Submission Accession No. S30578.

* cited by examiner

*NaPdf1*

```
            10         20         30         40         50         60
             |          |          |          |          |          |
          ATGGCTCGCTCCTTGTGCTTCATGGCATTTGCTATCTTGGCAAGGATGCTCTTTGTTGCC
            M  A  R  S  L  C  F  M  A  F  A  I  L  A  R  M  L  F  V  A
             |                                                |
           -25         -20                                   -10

70         80         90        100        110        120
             |          |          |          |          |          |
          TATGAGGTGCAAGCTAGAGAATGCAAAACAGAAAGCAACACATTTCCTGGAATATGCATT
            Y  E  V  Q  A  R  E  C  K  T  E  S  N  T  F  P  G  I  C  I
                         ↑                                   |
                         1                                   10

130        140        150        160        170        180
             |          |          |          |          |          |
          ACCAAACCACCATGCAGAAAAGCTTGTATCAGTGAGAAATTTACTGATGGTCATTGTAGC
            T  K  P  P  C  R  K  A  C  I  S  E  K  F  T  D  G  H  C  S
                         |                                   |
                         20                                  30

190        200        210        220        230        240
             |          |          |          |          |          |
          AAAATCCTCAGAAGGTGCCTATGTACTAAGCCATGTGTGTTTGATGAGAAGATGACTAAA
            K  I  L  R  R  C  L  C  T  K  P  C  V  F  D  E  K  M  T  K
                         |                   ↑               |
                         40                                  50

250        260        270        280        290        300
             |          |          |          |          |          |
          ACAGGAGCTGAAATTTTGGCTGAGGAAGCAAAAACTTTGGCTGCAGCTTTGCTTGAAGAA
            T  G  A  E  I  L  A  E  E  A  K  T  L  A  A  A  L  L  E  E
                         |                                   |
                         60                                  70

310        320        330        340        350        360
             |          |          |          |          |          |
          GAGATAATGGATAACTAATTAGAGATTAGAAGAAATTAAGGATGCAGTATCACACATAAT
            E  I  M  D  N  *
                         |
                         80

370        380        390        400        410        420
             |          |          |          |          |          |
          AAAGTTTCTACCTTTCTTAAAAGTGTAGCTAATGTTGTGTTTTAATTGGCTTTTAGTAGC 430        440        450        460        470        480
             |          |          |          |          |          |
          CTTTTATTACACTTTAAATAAGTGTGGCACTTCAATCCTTTGTGCAATCTTGCACTAAGT 490        500        510        520        530        540
             |          |          |          |          |          |
          TTATTTGTGTACTTTTAATGAAAATGACCTTCTATGGTCTTTGGTTAAAAAAAAAAAAA

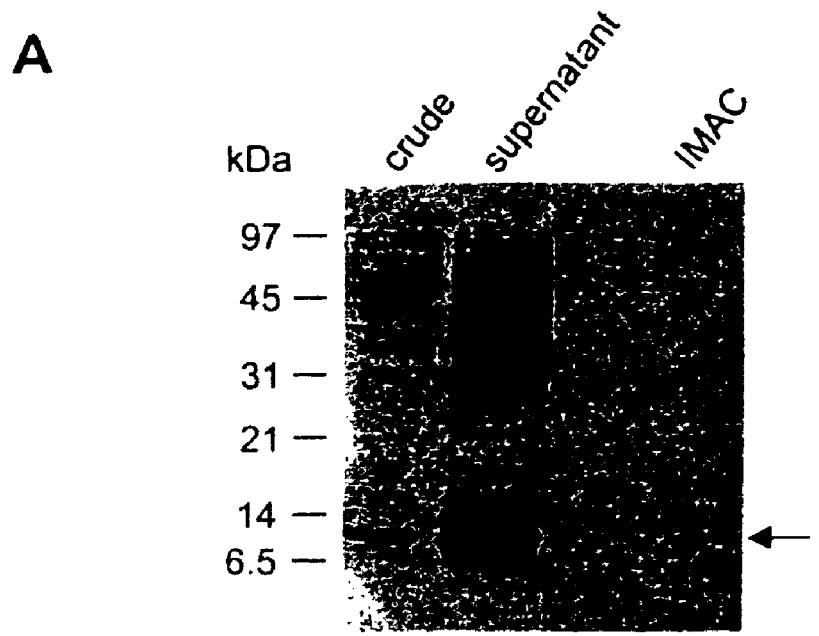
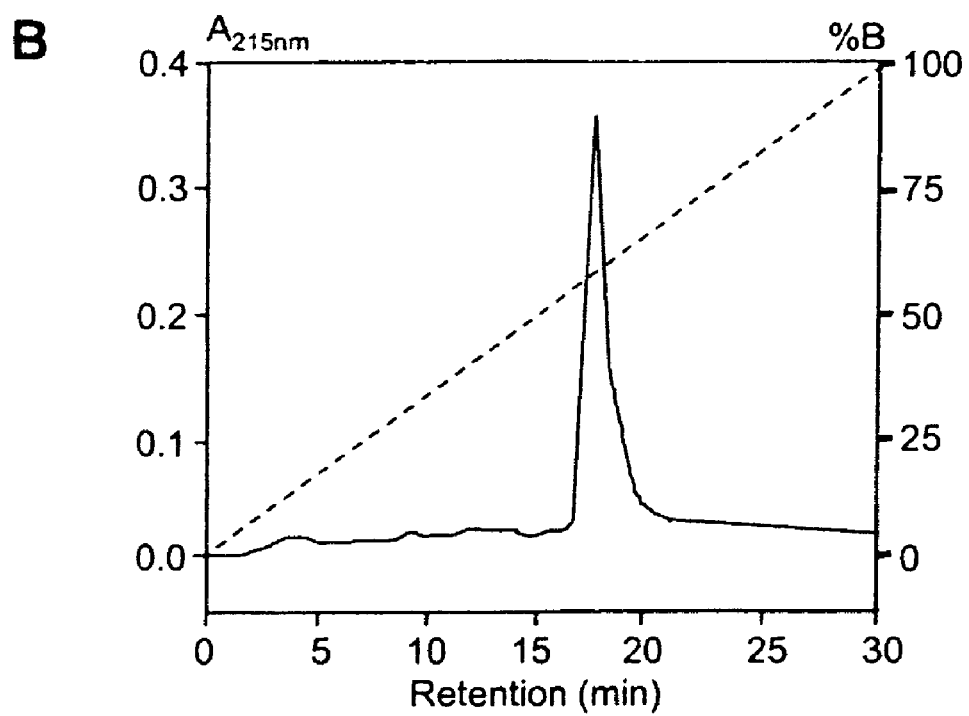
Figure 4

```
NaPdf1   (<400>18)  MARSLCFMAFAILAMMLFVAYEV------QA-RECKTESNTFPGICITKPP
PST      (<400>20)  MARSLCFMAFAILAMMLFVAYEV------QA-RECKTESNTFPGICITKPP
TTP3     (<400>21)  MARSIFFMAFLVLAMMLFVTYEV------EAQQICKAPSQTFPGLCFMDSS
NTS13    (<400>22)  MANSMRFFATVLLIALLVTATEMGPMTIAEA-RTCESQSHRFKGPCSRDSN
PPT      (<400>23)  MGRSIRLFATFFLIAMLFLSTEMGPMTSAEA-RTCESQSHRFHGTCVRESN
ATPIIIa  (<400>24)  MKLSMRLISAVLIMFMIFVATGMGPVT-VEA-RTCESQSHRFKGTCVSASN

NaPdf1   CRKACISEKFTDGHCSKILRRCLCTKPCVFDEKMTKTGAEILAEEAKTLAAALLEEEIMDN
PST      CRKACISEKFTDGHCSKLLRRCLCTKPCVFDEKMIKTGAETLVEEAKTLAAALLEEEIMDN
TTP3     CRKYCIKEKFTGGHCSKLQRKCLCTKPCVFDKISSEVKA-TLGEEAKTLSEVVLEEEIMME
NTS13    CATVCLTEGFSGGRCPWIPPRCFCTSPC--------------------------------
PPT      CASVCQTEGFIGGNCRAFRRRCFCTRNC--------------------------------
ATPIIIa  CANVCHNEGFVGGNCRGFRRRCFCTRHC--------------------------------
```

Figure 9

| | | | |
|---|---|---|---|
| Nicotiana alata | NaPdf1 | -REC-KTESNTFP-GICITKPPCRKACIS-EKFTDGH-CSK--ILRRCLCTKPC- | (<400>8) |
| Nicotiana tabacum | FST | -REC-KTESNTFP-GICITKPPCRKACIS-EKFTDGH-CSK--LLRRCLCTKPC- | (<400>25) |
| Lycopersicon esculentum | TPP3 | -QIC-KAPSQTFP-GLCFMDSSCRKYCIK-EKFTGGH-CSK--LQRKCLCTKPC- | (<400>26) |
| Solanum tuberosum | P322 | -RHC-ESLSHRFK-GPCTRDSNCASVCET-ERFSGGN-CHG-F-RRRCFCTKPC- | (<400>27) |
| Petunia inflata | PPT | -RTC-ESQSHRFH-GTCVRESNCASVCQT-EGFIGGN-CRA-F-RRRCFCTRNC- | (<400>28) |
| Glycine max | SE60 | -RVC-ESQSHGFH-GLCNRDHNCALVCRNE-G-FSGGRCKG-F-RRRCFCTRIC- | (<400>29) |
| Hordeum vulgare | γ1-H | -RIC-RRRSAGFK-GPCVSNKNCAQVCMQE-G-WGGGNCDG--PLRRCKCMRRC- | (<400>30) |
| Sinapis alba | M2A | PQKLC-QRPSGTWS-GVCGNNNACRNQCINLEKARHGS-CNYVFPAHKCICYFPC- | (<400>31) |
| Solanum tuberosum | PTH-St1 | -RNC-ESLSHRFK-GPCTRDSNC--------------------------------- | (<400>32) |
| Raphanus sativus | Rs-AFP1 | PQKLC-ERPSGTWS-GVCGNNNACKNQCINLEKARHGS-CNYVFPAHKCICYFPC- | (<400>33) |
| Raphanus sativus | Rs-AFP2 | PQKLC-QRPSGTWS-GVCGNNNACKNQCIRLEKARHGS-CNYVFPAHKCICYFPC- | (<400>34) |
| Sinapis alba | M1 | PQKLC-ERPSGTWS-GVCGNNNACKNQCINLEKARHGS-CNYVFPAHKCICYFPC- | (<400>35) |
| Sinapis alba | M2B | PQKLC-ARPSGTWSSGNCRNNNACRNFCIKLEKSRHGS-CNIPFPSNKCICYFPC- | (<400>36) |
| Triticum turgidium | γ1-P | -KIC-RRRSAGFK-GPCMSNKNCAQVCQQE-G-WGGGNCDG--PFRRCKCIRQC- | (<400>37) |
| Triticum turgidium | γ2-P | -KVC-RQRSAGFK-GPCVSDKNCAQVCLQE-G-WGGGNCDG--PFRRCKCIRQC- | (<400>38) |
| Vigna unguiculata | 10kDa | -KTC-ENLVDTYR-GPCFTTGSCDDHCKNKEHLLSGR-CR---DDVRCWCTRNC- | (<400>39) |
| Sorghum bicolor | SIα2 | -RVC-MGKSAGFK-GLCMRDQNCAQVCLQE-G-WGGGNCDG--VMRQCKCIRQCW | (<400>40) |
| Sorghum bicolor | SIα3 | -RVC-RRRSAGFK-GLCMSDHNCAQVCLQE-G-WGGGNCDG--VIRQCKCIRQCW | (<400>41) |
| Dalia merckii | Dm-AMP2 | -EVC-EKASKTWS-GNCGNTGHC--------------------------------- | (<400>42) |
| Sorghum bicolor | SIα1 | -RVC-MKGSQHHS-FPCISDRLCSNECVKEEGGWTAGYCH---LRYCRCQKAC- | (<400>43) |
| Pisum sativum | P1230 | -NTC-ENLAGSYK-GVCF--GGCDRHCRTQEGAISGR-CR---DDFRCWCTKNC- | (<400>44) |
| Aesculus hippocastanum | Ah-AMP1 | --LCNERPSQTWS-GNCGNTAHCDKQCQDWEKASHGA-CHKRENHWKCFCYFNC- | (<400>45) |
| Heuchera sanguinea | Hs-AFP1 | -KLC-DVPSGTWS-GHCGSSSKCSQQCKDREHFAYGGACHYQFPSVKCFCKRQC- | (<400>46) |
| Dalia merckii | Dm-AMP1 | -ELC-EKASKTWS-GNCGNTGHCDNQCKSWEGAAHGA-CHVRNGKHMCFCYFNC- | (<400>47) |
| Pisum sativum | P139 | -NTC-EHLADTYR-GVCFTNASCDDHCKNKAHLISGT-CH----DWKCFCTQNC- | (<400>48) |
| Clitoria ternatea | Ct-AMP1 | -NLC-ERASLTWT-GNCGNTGHCDTQCRNWESAKHGA-CHKRGN-WKCFCYFNC- | (<400>49) |

Figure 10

*H. punctigera* bioassay with transgenic tobacco

*H. armigera* bioassay with transgenic tobacco

DEFENSIN-ENCODING NUCLEIC ACID MOLECULES, USES THEREFOR AND TRANSGENIC PLANTS COMPRISING SAME

CROSS-REFERENCE TO RELATED APPLICATIONS

This application is a divisional application of U.S. patent application Ser. No. 11/062,999, filed Feb. 22, 2005; now U.S. Pat. No. 7,297,840 which is a continuation application of U.S. patent application Ser. No. 10/072,809, filed Feb. 8, 2002, now U.S. Pat. No. 7,041,877 which claims benefit of U.S. Provisional Application No. 60/267,271, filed Feb. 8, 2001, all of which are incorporated herein in their entirety to the extent not inconsistent herewith.

The present invention provides genetic molecules encoding plant floral defensin-like molecules and their use in generating transgenic plants having resistance or at least reduced sensitivity to plant pests including insects, microorganisms, fungi and/or viruses. The present invention further provides for the use of floral- and seed-derived defensins in the generation of insect resistance in plants. The plants may be monocotyledonous or dicotyledonous plants and are in particular, crop plants and ornamental flowering plants. The genetic molecules are also useful in generating recombinant defensin-like molecules for use in the topical application of compositions to prevent or otherwise retard pest-infestation of plants. The floral defensin-like molecules or genetic molecules encoding same of the present invention may be used alone or in combination with other agents such as a proteinase inhibitor precursor or a nucleic acid molecule encoding same or other molecules or their encoding nucleotide sequences.

Reference to any prior art in this specification is not, and should not be taken as, an acknowledgment or any form of suggestion that this prior art forms part of the common general knowledge in Australia or any other country.

The increasing sophistication of recombinant DNA techniques is greatly facilitating research and development in the agricultural industry. This is particularly the case in the horticultural area including the area of crop research. Of particular importance are the development of herbicide resistant plants and the development of pathogen resistant plants.

A number of approaches have been adopted to induce herbicide resistance in plants. For example, genes encoding enzymes, which deactivate or neutralize the active components of herbicides, have been expressed in plants. Whilst there has been some success in this approach, it is one component of a multi-disciplined and multi-strategy approach to maximizing yields of crops and products of crops and for maximizing returns from other activities within the agricultural and horticultural industries.

One of the major difficulties facing the agricultural and horticultural industries is the control of insect and other pathogen infestation of plants. Insects and other pathogens account for millions of tonnes of lost production on an annual basis. Although insecticides and other anti-pathogenic chemical agents have been successfully employed, there is a range of environmental and regulatory concerns with the continued use of chemical agents to control plant pests. Furthermore, the increasing use of chemical pesticides is providing selective pressure for the emergence of resistance in populations of pests. There is clearly a need to further investigate alternative mechanisms of inducing resistance in plants to pathogens such as insects, microorganisms, fungi, arachnid and viruses.

A range of genetic measures has been adopted in test trials. Whilst some success has been achieved, it is important for new and alternative genetic approaches to be developed to combat the difficulties of resistance.

One approach which has been suggested is the use of a group of proteins collectively known as "defensins". The defensins have previously been known as γ-thionins and are structurally distinct from the α- and β-thionin families. Most defensins isolated and studied to date have been derived from seeds, especially those from *Raphanus sativus* and other members of the Brassicaceae family. Seed defensins are small (~5 kDa) basic, cysteine-rich proteins and many have anti-fungal activity.

Over the last few years several cDNA clones have been isolated from the floral organs of solanaceous plants and *Arabidopsis* that encode proteins that are related to seed defensins. Unlike seed defensins, floral defensins are produced from precursor proteins that have an acidic C-terminal domain in addition to the defensin domain. The role of this acidic domain is unknown.

The defensin domain has little sequence in common with seed-derived defensins apart from eight cysteine residues that are strongly conserved. Although several cDNAs, which encode floral defensins, have been isolated, the corresponding proteins have not been isolated and their biological function has not been examined. The inventors have isolated both the cDNA and the corresponding floral defensin from the ornamental tobacco *Nicotiana alata*. They have determined that the defensin precursor is processed proteolytically to release mature defensin from the acidic C-terminal domain.

In accordance with the present invention, the inventors have determined that floral defensins have useful properties in inhibiting plant pest attack or infestation. Furthermore, a floral defensin from *Nicotiana alata* is shown to be particularly effective in controlling insect attack. The present invention also provides a new use of seed and known floral defensins in the control of insect infestation of plants.

SUMMARY OF THE INVENTION

Throughout this specification, unless the context requires otherwise, the word comprise, or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

The present invention relates generally to genetic molecules alone or in combination with other genetic molecules and their use to induce resistance in plants or parts of plants to pathogen infestation such as but not limited to insect infestation. More particularly, the present invention provides genetic molecules encoding defensin-like molecules alone or in combination with genetic molecules encoding a proteinase inhibitor or precursor thereof or other active molecule to inhibit insect, microbial, fungal, arachnid or viral attack or other form of infestation in plants. The present invention further encompasses compositions comprising the defensin-like molecules alone or in combination with a proteinase inhibitor or precursor thereof or other active molecule for topical application to plants or parts of plants to assist in the control of insect, microbial, fungal, arachnid or viral infestation of plants. The present invention further contemplates the use of the subject genetic molecules in the manufacture of transgenic plants with resistance or at least reduced susceptibility to insect, microbial, fungal, arachnid or viral attack or other form of infestation. The defensin molecules may also be used as molecular frameworks to carry heterologous amino acid sequences where the folding of the molecule is altered to a more active form. The present invention further encompasses genetic constructs comprising a promoter and/or other regulatory sequence naturally associated with the gene encoding the defensin-like molecule. The promoter and/or other regulatory sequence may be operably linked to a cDNA molecule encoding the defensin-like protein or may be operably linked to another gene or nucleotide sequence of interest such as but not limited to a gene encoding a proteinase inhibitor precursor. The present invention still further extends to transgenic plants or parts of transgenic plants with resistance or at least reduced sensitivity to attack or other form of infestation by insects, microorganisms, fungi and/or viruses. Particularly preferred plants are food and non-food crops such as cotton plants.

Accordingly, one aspect of the present invention provides an isolated nucleic acid molecule comprising a sequence of nucleotides encoding or complementary to a sequence encoding a polypeptide comprising, in its precursor form, an N-terminal signal domain, a mature domain and an acidic C-terminal domain wherein said polypeptide is produced during flower development and its mature domain has activity against one or more plant pests.

Another aspect of the present invention is directed to an isolated nucleic acid molecule comprising a sequence of nucleotides encoding or complementary to a sequence encoding a polypeptide comprising, in its precursor form, an N-terminal signal domain, a mature domain and an acidic C-terminal domain wherein said polypeptide is produced during flower development and its mature domain comprises the structure:

(SEQ ID NO:62)

$a_1a_2C_Ia_3a_4a_5a_6a_7a_8a_9a_{10}a_{11}a_{12}C_{II}a_{13}a_{14}a_{15}a_{16}a_{17}$ $C_{III}a_{18}a_{19}a_{20}C_{IV}a_{21}a_{22}a_{23}a_{24}a_{25}a_{26}a_{27}a_{28}a_{29}C_Va_{30}$ $a_{31}a_{32}a_{33}a_{34}a_{35}C_{VI}a_{36}C_{VII}a_{37}a_{38}a_{39}C_{VIII}$ wherein "a" may be the same or different and represents any amino acid residue, the numerical subscript on each "a" represents its position in the amino acid sequence and "C" represents a cysteine residue at a position indicated by its Roman numeral and wherein the mature domain has activity against one or more plant pests with the proviso that the polypeptide is not FST or TPP3.

A further aspect of the present invention contemplates an isolated nucleic acid molecule comprising a sequence of nucleotides encoding or complementary to a sequence encoding a polypeptide comprising, in its precursor form, an N-terminal signal domain, a mature domain and an acidic C-terminal domain wherein said polypeptide is produced in the epidermal layers of petals and sepals, the cortical cells of the style and the connective tissue of the anthers and its mature domain comprises the structure:

(SEQ ID NO:62)

$a_1a_2C_Ia_3a_4a_5a_6a_7a_8a_9a_{10}a_{11}a_{12}C_{II}a_{13}a_{14}a_{15}a_{16}a_{17}$ $C_{III}a_{18}a_{19}a_{20}C_{IV}a_{21}a_{22}a_{23}a_{24}a_{25}a_{26}a_{27}a_{28}a_{29}C_Va_{30}$ $a_{31}a_{32}a_{33}a_{34}a_{35}C_{VI}a_{36}C_{VII}a_{37}a_{38}a_{39}C_{VIII}$ wherein "a" may be the same or different and represents any amino acid residue, the numerical subscript on each "a" represents its position in the amino acid sequence and "C" represents a cysteine residue at a position indicated by its Roman numeral and wherein the mature domain has activity against one or more plant pests with the proviso that the polypeptide is not FST or TPP3.

Still another aspect of the present invention provides an isolated nucleic acid molecule comprising a sequence of nucleotides encoding or complementary to a sequence encoding a polypeptide comprising, in its precursor form, an N-terminal signal domain, a mature domain and an acidic C-terminal domain wherein said mature domain comprises the amino acid sequence set forth in SEQ ID NO:8 or an amino acid sequence having at least about 70% similarity thereto or is encoded by a nucleotide sequence set forth in SEQ ID NO:7 or a nucleotide sequence having at least about 70% similarity thereto or a nucleotide sequence capable of hybridizing to SEQ ID NO:7 or its complementary form under low stringency conditions at 42° C.

Still a further aspect of the present invention provides a genetic construct comprising a promoter or functional equivalent thereof operably linked to a nucleotide sequence encoding a floral-derived, defensin-like molecule having a mature domain comprising the amino acid sequence:

(SEQ ID NO:62)

$a_1a_2C_Ia_3a_4a_5a_6a_7a_8a_9a_{10}a_{11}a_{12}C_{II}a_{13}a_{14}a_{15}a_{16}a_{17}$ $C_{III}a_{18}a_{19}a_{20}C_{IV}a_{21}a_{22}a_{23}a_{24}a_{25}a_{26}a_{27}a_{28}a_{29}C_Va_{30}$ $a_{31}a_{32}a_{33}a_{34}a_{35}C_{VI}a_{36}C_{VII}a_{37}a_{38}a_{39}C_{VIII}$ wherein "a" may be the same or different and represents any amino acid residue, the numerical subscript on each "a" represents its position in the amino acid sequence and "C" represents a cysteine residue at a position indicated by its Roman numeral and wherein said mature domain exhibits inhibitory activity against plant pests such as insect pests with the proviso that the defensin-like molecule is not FST or TPP3.

Yet another aspect of the present invention is directed to the amino acid sequence of the mature domain comprising the amino acid sequence [SEQ ID NO:58]:

$X_{30}X_{31}CX_{32}X_{33}X_{34}SX_{35}X_{36}FX_{37}GX_{38}CX_{39}X_{40}X_{41}X_{42}X_{43}CX_{44}X_{45}X_{46}CX_{47}X_{48}EX_{49}FX_{50}X_{51}GX_{52}CX53X_{54}X_{55}X_{56}X_{57}X_{58}CX_{59}CTX_{60}X_{61}C$ wherein
$X_{30}$=R or Q
$X_{31}$=E, I or T
$X_{32}$=K or E
$X_{33}$=T, A or S
$X_{34}$=E, P or Q
$X_{35}$=N, Q or H
$X_{36}$=T or R
$X_{37}$=P, K or H
$X_{38}$=I, L, P or T
$X_{39}$=I, F, S or V
$X_{40}$=T, M, R or S
$X_{41}$=K, D, E or A
$X_{42}$=P or S
$X_{43}$=P, S or N
$X_{44}$=R or A
$X_{45}$=K, T, S or N
$X_{46}$=A, Y or V
$X_{47}$=I, L, Q or H
$X_{48}$=S, K, T or N
$X_{49}$=K or G
$X_{50}$=T, S, I, or V $X_{51}$=D or G
$X_{52}$=H, R, or N
$X_{53}$=S, P or R
$X_{54}$=K, W, A or G
$X_{55}$=I, L or F
$X_{56}$=L, Q, P or R
$X_{57}$=R or P
$X_{58}$=R or K
$X_{59}$=L or F
$X_{60}$=K, S or R
$X_{61}$=P, N or H Yet a further aspect of the present invention is directed to the mature domain-encoding sequence operably linked to a signal domain comprising the amino acid sequence [SEQ ID NO:59]:

$$MX_1X_2SX_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}X_{25}X_{26}X_{27}X_{28}AX_{29}$$

wherein
$X_1$=A, G or K
$X_2$=R, N, or L
$X_3$=L, I or M
$X_4$=C, F or R
$X_5$=F or L
$X_6$=M, F or I
$X_7$=A or S
$X_8$=F, T or A
$X_9$=A, L, V or F
$X_{10}$=I, V, L or F
$X_{11}$=L or I
$X_{12}$=A, I or M
$X_{13}$=M, A or F
$X_{14}$=M or L
$X_{15}$=L or I
$X_{16}$=F or V
$X_{17}$=V, T or L
$X_{18}$=A, T or S
$X_{19}$=Y or T
$X_{20}$=E or G
$X_{21}$=V or M
$X_{22}$=no amino acid or G
$X_{23}$=no amino acid or P
$X_{24}$=no amino acid, M or V
$X_{25}$=no amino acid or T
$X_{26}$=no amino acid, I or S
$X_{27}$=no amino acid, A or V
$X_{28}$=Q or E
$X_{29}$=no amino acid or Q Even still another aspect of the present invention is directed to the mature domain-encoding sequence operably linked to an acidic C-terminal domain comprising the sequence [SEQ ID NO:60]:

$$X_{62}X_{63}X_{64}X_{65}X_{66}X_{67}X_{68}X_{69}X_{70}X_{71}X_{72}X_{73}X_{74}X_{75}X_{76}X_{77}X_{78}X_{80}X_{81}X_{82}X_{83}X_{84}X_{85}X_{86}X_{87}X_{88}X_{89}X_{90}X_{91}X_{92}X_{93}X_{94}X_{95}$$

wherein
$X_{62}$=no amino acid or V
$X_{63}$=no amino acid or F
$X_{64}$=no amino acid or D
$X_{65}$=no amino acid or E or K
$X_{66}$=no amino acid or K or I
$X_{67}$=no amino acid or M or S
$X_{68}$=no amino acid or T, I or S
$X_{69}$=no amino acid or K or E
$X_{70}$=no amino acid or T or V
$X_{71}$=no amino acid or G or K
$X_{72}$=no amino acid or A
$X_{73}$=no amino acid or E
$X_{74}$=no amino acid or I or T
$X_{75}$=no amino acid or L
$X_{76}$=no amino acid or A, V or G
$X_{77}$=no amino acid or E
$X_{78}$=no amino acid or E
$X_{79}$=no amino acid or A
$X_{80}$=no amino acid or K
$X_{81}$=no amino acid or T
$X_{82}$=no amino acid or L
$X_{83}$=no amino acid or A or S
$X_{84}$=no amino acid or A or E
$X_{85}$=no amino acid or A or V
$X_{86}$=no amino acid or L or V
$X_{87}$=no amino acid or L
$X_{88}$=no amino acid or E
$X_{89}$=no amino acid or E
$X_{90}$=no amino acid or E
$X_{91}$=no amino acid or I
$X_{92}$=no amino acid or M
$X_{93}$=no amino acid or D or M
$X_{94}$=no amino acid or N or E Even yet another aspect of the present invention is directed to the defensin-like molecule comprising the sequence [SEQ ID NO:61]:

$$MX_1X_2SX_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}X_{25}X_{26}X_{27}X_{28}AX_{29}X_{30}X_{31}CX_{32}X_{33}X_{34}SX_{35}X_{36}FX_{37}GX_{38}CX_{39}X_{40}X_{41}X_{42}X_{43}CX_{44}X_{45}X_{46}C X_{47}X_{48}EX_{49}FX_{50}X_{51}GX_{52}CX_{53}X_{54}X_{55}X_{56}X_{57}X_{58}CX_{59}CTX_{60}X_{61}CX_{62}X_{63}X_{64}X_{65}X_{66}X_{67}X_{68}X_{69}X_{70}X_{71}X_{72}X_{73}X_{74}X_{75}X_{76}X_{77}X_{78}X_{79}X_{80}X_{81}X_{82}X_{83}X_{84}X_{85}X_{86}X_{87}X_{88}X_{89}X_{90}X_{91}X_{92}X_{93}X_{94}$$

wherein
$X_1$=A, G or K
$X_2$=R, N, or L
$X_3$=L, I or M
$X_4$=C, F or R
$X_5$=F or L
$X_6$=M, F or I
$X_7$=A or S
$X_8$=F, T or A
$X_9$=A, L, V or F
$X_{10}$=I, V, L or F
$X_{11}$=L or I
$X_{12}$=A, I or M
$X_{13}$=M, A or F
$X_{14}$=M or L
$X_{15}$=L or I
$X_{16}$=F or V
$X_{17}$=V, T or L
$X_{18}$=A, T or S
$X_{19}$=Y or T
$X_{20}$=E or G
$X_{21}$=V or M
$X_{22}$=no amino acid or G
$X_{23}$=no amino acid or P
$X_{24}$=no amino acid, M or V
$X_{25}$=no amino acid or T
$X_{26}$=no amino acid, I or S
$X_{27}$=no amino acid or A or V
$X_{28}$=Q or E
$X_{29}$=no amino acid or Q
$X_{30}$=R or Q
$X_{31}$=E, I or T
$X_{32}$=K or E
$X_{33}$=T, A or S $X_{34}$=E, P or Q
$X_{35}$=N, Q or H
$X_{36}$=T or R
$X_{37}$=P, K or H
$X_{38}$=I, L, P or T
$X_{39}$=I, F, S or V
$X_{40}$=T, M, R or S
$X_{41}$=K, D, E or A
$X_{42}$=P or S
$X_{43}$=P, S or N
$X_{44}$=R or A
$X_{45}$=K, T, S or N
$X_{46}$=A, Y or V
$X_{47}$=I, L, Q or H
$X_{48}$=S, K, T or N
$X_{49}$=K or G
$X_{50}$=T, S, I, or V
$X_{51}$=D or G
$X_{52}$=H, R, or N
$X_{53}$=S, P or R
$X_{54}$=K, W, A or G
$X_{55}$=I, L or F
$X_{56}$=L, Q, P or R
$X_{57}$=R or P
$X_{58}$=R or K
$X_{59}$=L or F
$X_{60}$=K, S or R
$X_{61}$=P, N or H
$X_{62}$=no amino acid or V
$X_{63}$=no amino acid or F
$X_{64}$=no amino acid or D
$X_{65}$=no amino acid or E or K
$X_{66}$=no amino acid or K or I
$X_{67}$=no amino acid or M or S
$X_{68}$=no amino acid or T, I or S
$X_{69}$=no amino acid or K or E
$X_{70}$=no amino acid or T or V
$X_{71}$=no amino acid or G or K
$X_{72}$=no amino acid or A
$X_{73}$=no amino acid or E
$X_{74}$=no amino acid or I or T
$X_{75}$=no amino acid or L
$X_{76}$=no amino acid or A, V or G
$X_{77}$=no amino acid or E
$X_{78}$=no amino acid or E
$X_{79}$=no amino acid or A
$X_{80}$=no amino acid or K
$X_{81}$=no amino acid or T
$X_{82}$=no amino acid or L
$X_{83}$=no amino acid or A or S
$X_{84}$=no amino acid or A or E
$X_{85}$=no amino acid or A or V
$X_{86}$=no amino acid or L or V
$X_{87}$=no amino acid or L
$X_{88}$=no amino acid or E
$X_{89}$=no amino acid or E
$X_{90}$=no amino acid or E
$X_{91}$=no amino acid or I
$X_{92}$=no amino acid or M
$X_{93}$=no amino acid or D or M
$X_{94}$=no amino acid or N or E Another aspect of the present invention is directed to the genetic construct comprising a nucleotide sequence selected from SEQ ID NO:7, SEQ ID NO:13, SEQ ID NO:15 and SEQ ID NO:17 or a nucleotide sequence having at least 70% similarity to one or more of SEQ ID NO:8, SEQ ID NO:14, SEQ ID NO:16 and SEQ ID NO:18 or a nucleotide sequence capable of hybridizing to SEQ ID NO:7, SEQ ID NO:13, SEQ ID NO:15 and SEQ ID NO:17 or a complementary form thereof.

A further aspect of the present invention provides a genetic construct for use in generating insect-resistant transgenic plants, said transgenic plants producing a defensin or defensin-like molecule selected from SEQ ID NO:8, SEQ ID NO:14, SEQ ID NO:16 and SEQ ID NO:18 as well as SEQ ID NO:20 to SEQ ID NO:49 or an amino acid sequence having at least 70% similarity to any one of SEQ ID NO:8, SEQ ID NO:14, SEQ ID NO:16 and SEQ ID NO:18.

Still another aspect of the present invention further contemplates a method for generating a plant with increased or enhanced resistance to a plant pest, said method comprising introducing into the genome of a plant cell or genome of a group of plant cells a genetic construct comprising a promoter or functional equivalent thereof operably linked to a nucleotide sequence encoding a floral-derived, defensin-like molecule having a mature domain comprising the amino acid sequence:

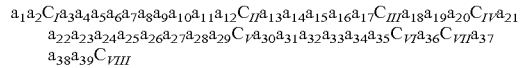

wherein "a" may be the same or different and represents any amino acid residue, the numerical subscript on each "a" represents its position in the amino acid sequence and "C" represents a cysteine residue at a position indicated by its Roman numeral and wherein said mature domain exhibits inhibitory activity against plant pests such as insect pests and regenerating a plant from said cell or group of cells.

Still a further aspect of the present invention is directed to the defensin-like molecule comprising a mature domain having the amino acid sequence [SEQ ID NO:58]:

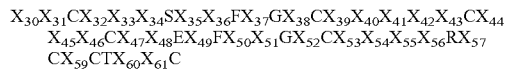

wherein
$X_{30}$=R or Q
$X_{31}$=E, I or T
$X_{32}$=K or E
$X_{33}$=T, A or S
$X_{34}$=E, P or Q
$X_{35}$=N, Q or H
$X_{36}$=T or R
$X_{37}$=P, K or H
$X_{38}$=I, L, P or T
$X_{39}$=I, F, S or V
$X_{40}$=T, M, R or S
$X_{41}$=K, D, E or A
$X_{42}$=P or S
$X_{43}$=P, S or N
$X_{44}$=R or A
$X_{45}$=K, T, S or N
$X_{46}$=A, Y or V
$X_{47}$=I, L, Q or H
$X_{48}$=S, K, T or N
$X_{49}$=K or G
$X_{50}$=T, S, I, or V
$X_{51}$=D or G
$X_{52}$=H, R, or N
$X_{53}$=S, P or R
$X_{54}$=K, W, A or G
$X_{55}$=I, L or F
$X_{56}$=L, Q P or R
$X_{57}$=R o P $X_{58}$=R or K
$X_{59}$=L or F
$X_{60}$=K, S or R
$X_{61}$=P, N or H Yet another aspect of the present invention provides a method for generating a plant with increased or enhanced resistance to an insect, said method comprising introducing into the genome of a plant cell or genome of a group of plant cells a genetic construct comprising a promoter or functional equivalent thereof operably linked to a nucleotide sequence encoding a defensin-like molecule having a mature domain comprising the amino acid sequence:

(SEQ ID NO:62)
$a_1a_2C_Ia_3a_4a_5a_6a_7a_8a_9a_{10}a_{11}a_{12}C_{II}a_{13}a_{14}a_{15}a_{16}a_{17}$ $C_{III}a_{18}a_{19}a_{20}C_{IV}a_{21}a_{22}a_{23}a_{24}a_{25}a_{26}a_{27}a_{28}a_{29}C_Va_{30}$ $a_{31}a_{32}a_{33}a_{34}a_{35}C_{VI}a_{36}C_{VII}a_{37}a_{38}a_{39}C_{VIII}$ wherein "a" may be the same or different and represents any amino acid residue, the numerical subscript on each "a" represents its position in the amino acid sequence and "C" represents a cysteine residue at a position indicated by its Roman numeral and wherein said mature domain exhibits inhibitory activity against plant pests such as insect pests and regenerating a plant from said cell or group of cells.

Yet a further aspect of the present invention provides a transfected or transformed cell, tissue or organ from a plant or a transformed microbial cell, said cell, tissue or organ comprising a nucleic acid molecule comprising a sequence of nucleotides encoding or complementary to a sequence encoding a polypeptide comprising, in its precursor form, an N-terminal signal domain, a mature domain and an acidic C-terminal domain wherein said polypeptide is produced during flower development and its mature domain has activity against one or more plant pests.

Even still another aspect of the present invention is directed to the nucleic acid molecule comprising a sequence of nucleotides encoding or complementary to a sequence encoding a polypeptide comprising, in its precursor form, an N-terminal signal domain, a mature domain and an acidic C-terminal domain wherein said polypeptide is produced during flower development and its mature domain comprises the structure:

(SEQ ID NO:62)
$a_1a_2C_Ia_3a_4a_5a_6a_7a_8a_9a_{10}a_{11}a_{12}C_{II}a_{13}a_{14}a_{15}a_{16}a_{17}$ $C_{III}a_{18}a_{19}a_{20}C_{IV}a_{21}a_{22}a_{23}a_{24}a_{25}a_{26}a_{27}a_{28}a_{29}C_Va_{30}$ $a_{31}a_{32}a_{33}a_{34}a_{35}C_{VI}a_{36}C_{VII}a_{37}a_{38}a_{39}C_{VIII}$ wherein "a" may be the same or different and represents any amino acid residue, the numerical subscript on each "a" represents its position in the amino acid sequence and "C" represents a cysteine residue at a position indicated by its Roman numeral and wherein the mature domain has activity against one or more plant pests.

Even yet another aspect of the present invention, insofar as it relates to plants, further extends to progeny of the plants engineered to express the nucleic acid molecule encoding the defensin-like molecule or a variant or homologue thereof as well as vegetative, propagative and reproductive parts of the plants, such as flowers (including cut or severed flowers), parts of plants, fibrous material from plants (for example, cotton) and reproductive portions including cuttings, pollen, seeds and callus.

Another aspect of the present invention provides a genetically modified plant cell or multicellular plant or progeny thereof or parts of a genetically modified plant capable of producing a heterologous defensin-like molecule as herein described wherein said transgenic plant is resistant or has reduced sensitivity to plant pests such as insects.

A further aspect of the present invention comprises one or more genetic constructs alone or in combination comprising a first promoter operably linked to a first nucleotide sequence wherein said first nucleotide sequence encodes a defensin-like molecule capable of inhibiting a plant pest such as an insect, said construct further comprising a second promoter operably linked to a second nucleotide sequence wherein said second nucleotide sequence encodes a proteinase inhibitor or precursor thereof.

BRIEF DESCRIPTION OF THE FIGURES

FIG. 1 is a representation of the nucleotide sequence (SEQ ID NO:17) and the predicted amino acid sequence (SEQ ID NO:18) of NaPdf1 (*Nicotiana alata* plant defensin 1), the cDNA encoding the floral defensin from *Nicotiana alata*. Only one strand with the polarity of the mRNA is shown and the nucleotides are numbered above. The amino acid sequence, shown in single letter code, is given below the nucleotide sequence and is numbered beginning with 1 for the first amino acid of the mature protein. The putative signal peptide is indicated by negative numbers and is underlined. The mature protein is boxed and arrows depict the predicted cleavage sites of the signal peptide and the end of the mature protein. The first stop codon is marked with an asterisk (*) and the two polyadenylation sites are in bold. For further detail, refer to Example 7.

FIG. 4A is a representation showing bacterial expression of N-terminal hexahistidine-tagged pro-defensin (6H.NaproPdf1) encoded by the NaPdf1 cDNA. Lane 1: total protein extracted 6 h post-induction with 1 mM IPTG in 1×SDS sample loading buffer. Lane 2: soluble proteins in the 8 M urea lysate. Lane 3: induced protein purified by IMAC. The proteins were separated on a 15% w/v SDS-polyacrylamide gel and were stained with Coomassie Blue. Molecular size markers are the Broad Range standards from Bio-Rad. The induced ~12 kDa protein (arrowed) was substantially pure after immobilized metal affinity chromatography (IMAC).

FIG. 4B shows a reverse-phase HPLC chromatogram of a sample of the metal affinity purified 6H.NaproPdf1 protein (IMAC from A), eluted as described in Example

FIG. 9 is an alignment of the amino acid sequence of NaPdf1 (SEQ ID NO:18) with the predicted amino acid sequences encoded from five other flower-derived cDNA clones, as follows:

FST (SEQ ID NO:20)
(flower specific thionin): Gu et al., *Mol. Gen. Genet* 234: 89-96, 1992;
TPP3: (SEQ ID NO:21) Milligan and Gasser, *Plant Mol. Biol.* 28: 691-711, 1995;
NTS13: (SEQ ID NO:22) Li and Gray, *Plant Physiology* 120: 633, 1999;
PPT: (SEQ ID NO:23) Karunanandaa et al., *Plant Mol. Biol.*, 26: 459-464, 1994;
ATPIIIa: (SEQ ID NO:24) Yu et al., Direct Submission, Accession No. S30578, 1999.

Some, but not all floral defensins have a C-terminal acidic domain of 32-33 amino acids.

FIG. 10 is an alignment of the amino acid sequence of the mature domain of NaPdf1 with the amino acid sequences of the mature domain of other members of the plant defensin family. The N-terminal amino acid in the Rs-AFP1, Rs-AFP2, M1, M2A and M2B sequence which is represented by "pQ" is a pyroglutamic acid. The sequences are derived from the following sources:—

FST: Gu et al. (1992; supra) (SEQ ID NO:25);
TPP3: Milligan and Gasser (1995; supra) (SEQ ID NO:26);
p322: Steikema et al., *Plant Mol. Biol.* 11: 255-269, 1988 (SEQ ID NO:27);
PPT: Karunanandaa et al. (1994; supra) (SEQ ID NO:28);
SE60: Choi et al., *Plant Physiology* 101: 699-700, 1993; Choi et al., *Mol. Gen. Genet.* 246: 266-268, 1995 (SEQ ID NO:29);
γ1-H: Mendez et al., *Eur. J. Biochem.* 194: 533-539, 1990 (SEQ ID NO:30);
M2A, M1 and M2B: Neumann et al., *Int. J. Protein & Peptide Research* 47: 437-446, 1996 (SEQ ID NO:31, SEQ ID NO:35 and SEQ ID NO:36, respectively);
Pth-St1: Moreno et al., *Eur. J. Biochem.* 223: 135-139, 1995 (SEQ ID NO:32);
Rs-AFP1 and Rs-AFP2: Terras et al., *J. Biological Chemistry* 267: 15301-15309, 1992; Terras et al., *FEBS Letters* 316: 233-240, 1993; Terras et al., *Plant Cell* 7: 573-588, 1995; and Fant et al., *The solution structure by $^1$H-NMR of Rs-AFP*1, *a plant antifungal protein from radish seeds*. In: LP Ingman, J Jokissaari, J Lounila (eds), *Abstracts of the 12th European Experimental NMR Conference*, p 247, 1994 (SEQ ID NO:33 and SEQ ID NO:34, respectively);
γ1-P: Collila et al., *FEBS Letters* 270: 191-194, 1990 (SEQ ID NO:37);
γ2-P: Collila et al., (1990; supra) (SEQ ID NO:38);
10 kDa: Ishibashi et al., *Plant Mol. Biol.* 15: 59-64, 1990 (SEQ ID NO:39);
SIα2, SIα3 and SIα1: Bloch and Richardson, *FEBS Letters* 279: 101-104, 1991 and Nitti et al., *Eur. J. Biochem.* 228: 250-256, 1995 (SEQ ID NO:40, SEQ ID NO:41 and SEQ ID NO:43, respectively);
Dm-AMP2, Ah-AMP1,
Hs-AFP1, Dm-AMP1 and
Ct-AMP1: Osborn et al., *FEBS Letters* 368: 257-262, 1995 (SEQ ID NO:42, SEQ ID NO:45, SEQ ID NO:46, SEQ ID NO:47 and SEQ ID NO:49, respectively);
pI230 and P139: Chiang and Hagwiger, *Mol. Plant-Microbe Interact* 4: 324-331, 1991 (SEQ ID NO:44 and SEQ ID NO:48, respectively);
NeThio1 and NeThio2: Yamada et al., *Plant Physiology* 115: 314, 1997; (SEQ ID NO:50 and SEQ ID NO:51); and
NpThio1: Komori et al., *Plant Physiology* 115: 314, 1997 (SEQ ID NO:52).

Figure 11:
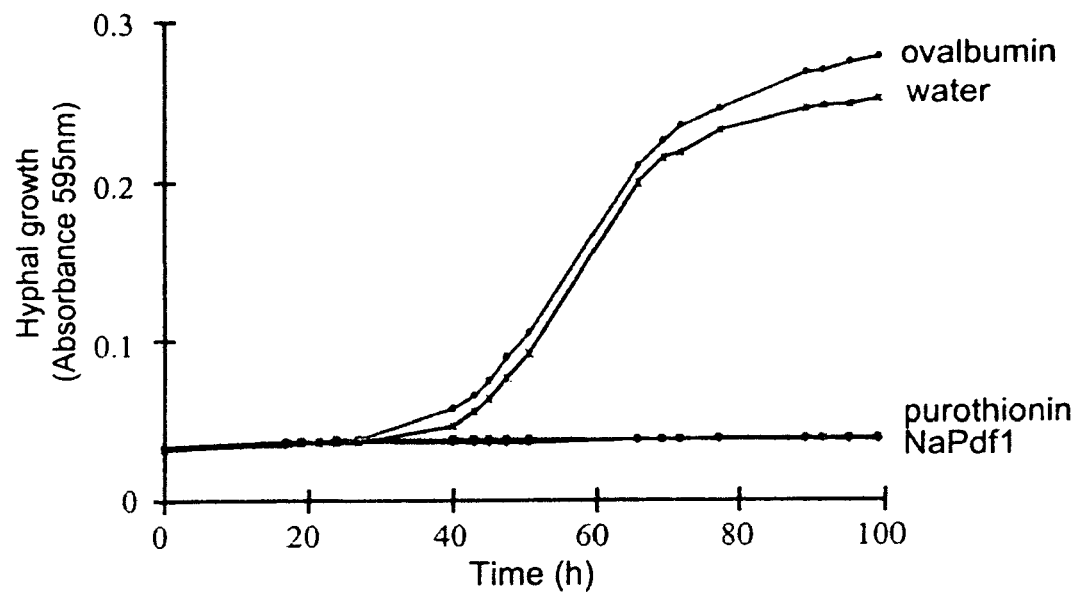

FIG. 11 shows growth inhibition curves of various agents against *Botrytis cinerea*, as monitored by absorbance at 595 nm. Each treatment was performed in quadruplicate. Purified NaPdf1 protein at 20 μg/ml was assayed. Water and ovalbumin (20 μg/ml) served as negative controls and a mixture of the antifungal proteins α- and β-purothionin (20 μg/ml) was used as a positive control.

Figure 12A:
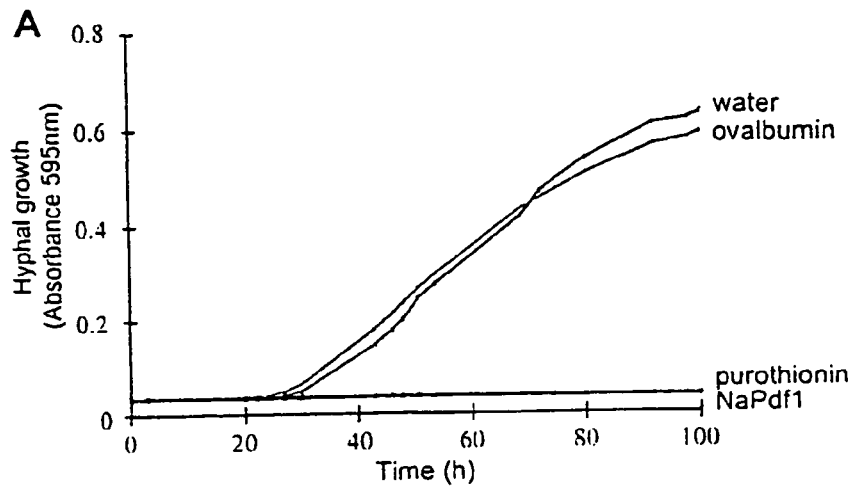
Figure 12B:
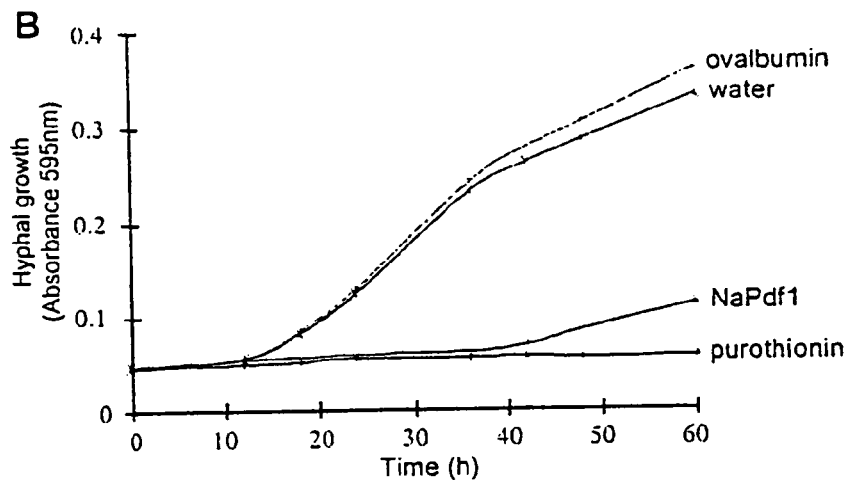
Figure 12C:
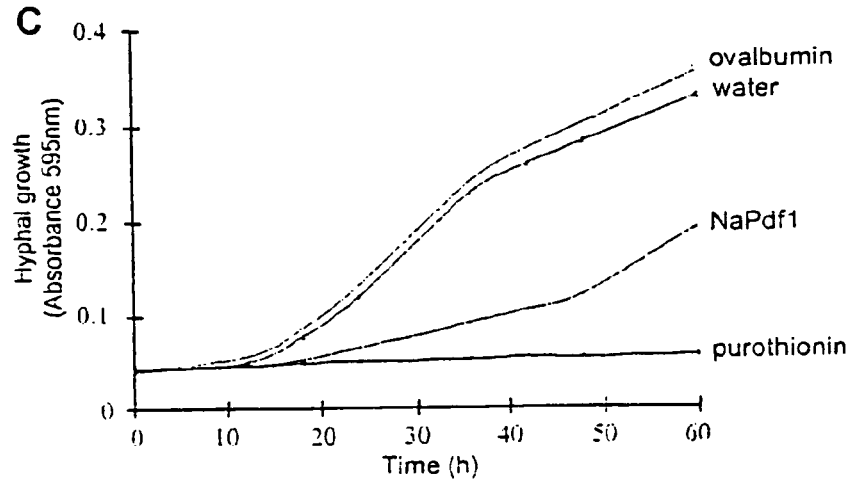

FIGS. 12A-12C show growth inhibition curves of various agents against *Fusarium oxysporum* f. sp. *dianthi* (12A) and *F. oxysporum* f. sp. *vasinfectum* (12B and 12C), as monitored by absorbance at 595 nm. Each treatment was performed in quadruplicate. Purified NaPdf1 protein at 20 μg/ml (12A and 12B) and 10 μg/ml (12C) were assayed. Water and ovalbumin (20 μg/ml, 12A and 12B; 10 μg/ml, 12C) served as negative controls, and a mixture of the antifungal proteins α- and β-purothionin (20 μg/ml, A and B; 10 μg/ml, C) was used as a positive control.

Figure 13:
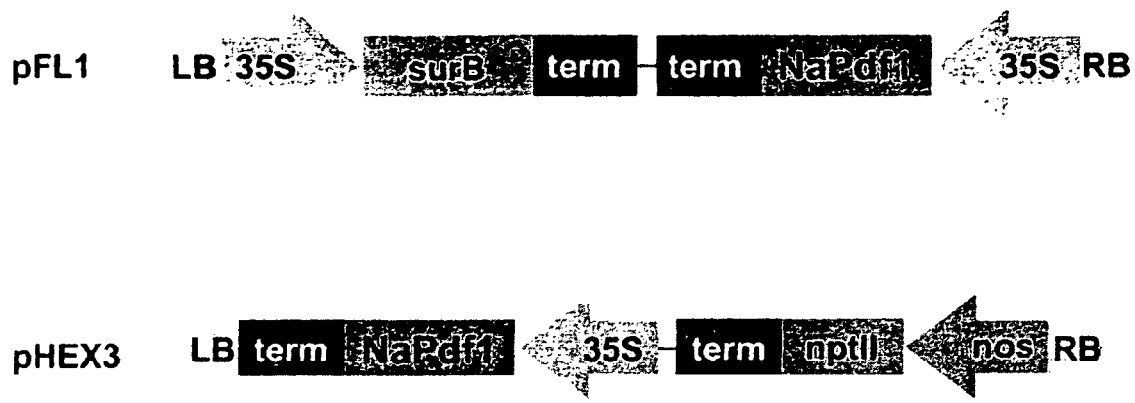

FIG. 13 is a schematic of plant transformation constructs pFL1 and pHEX3, used for the transformation of tobacco and cotton. Both constructs contain the *N. alata* defensin, NaPdf1, under the control of the CaMV35S promoter/terminator. The region designated "surB" codes for resistance to the herbicide glean, and that designated "nptII" codes for resistance against the antibiotic kanamycin.

Figure 14:
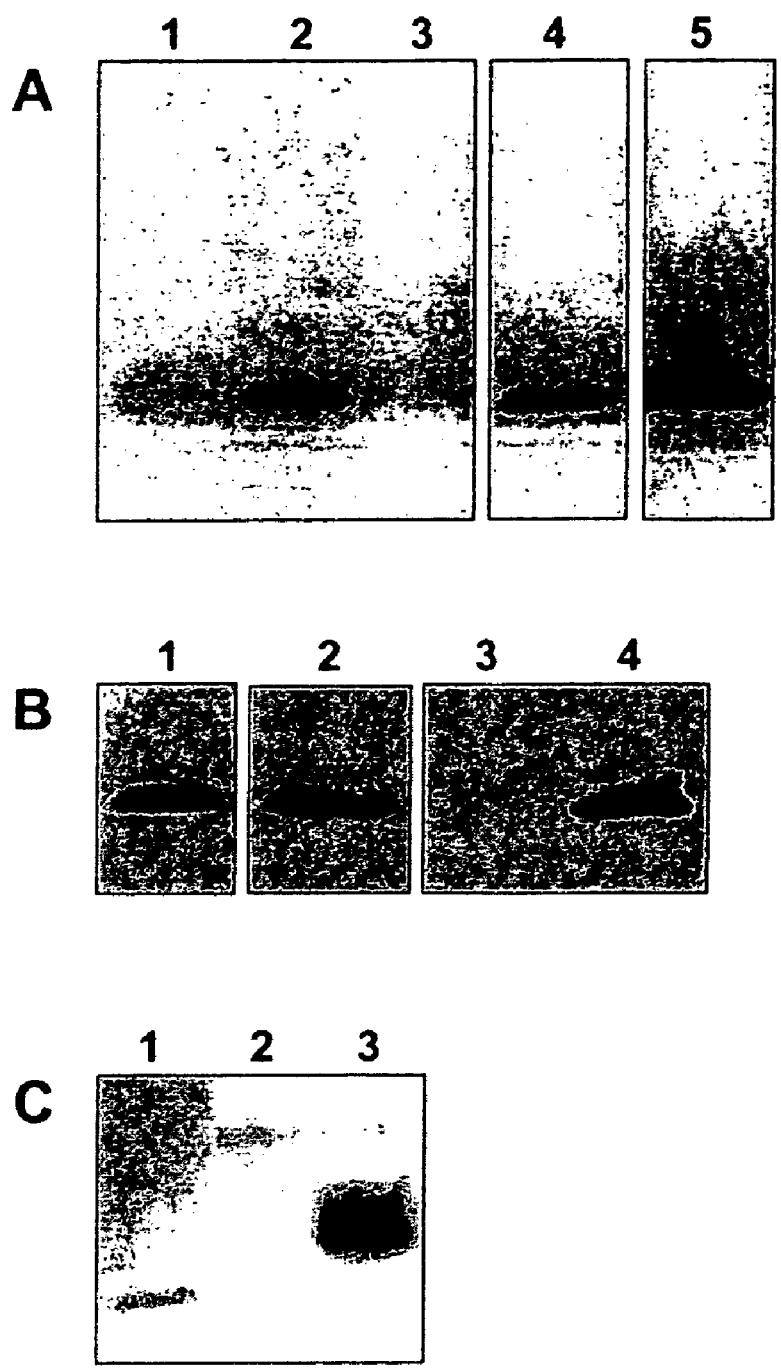
Figure 15A:
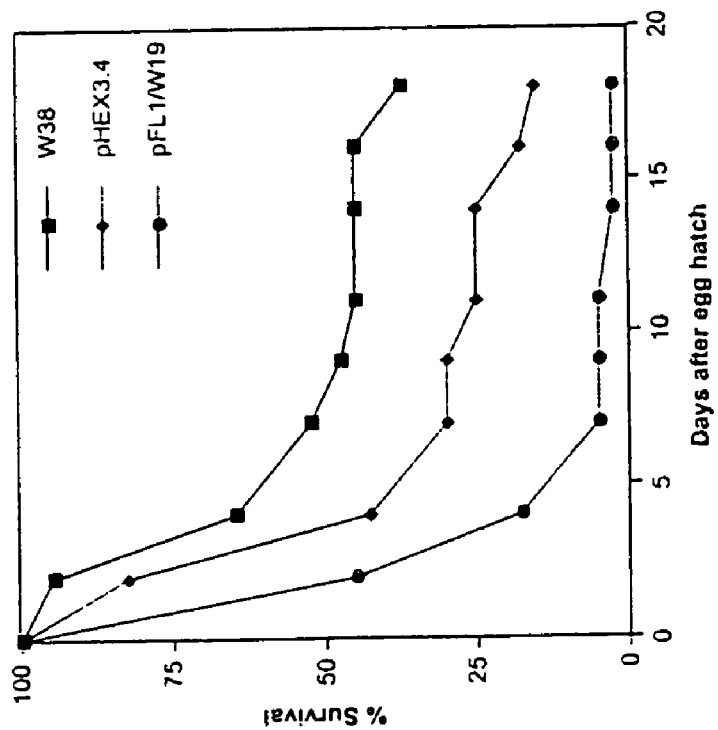
Figure 15B:
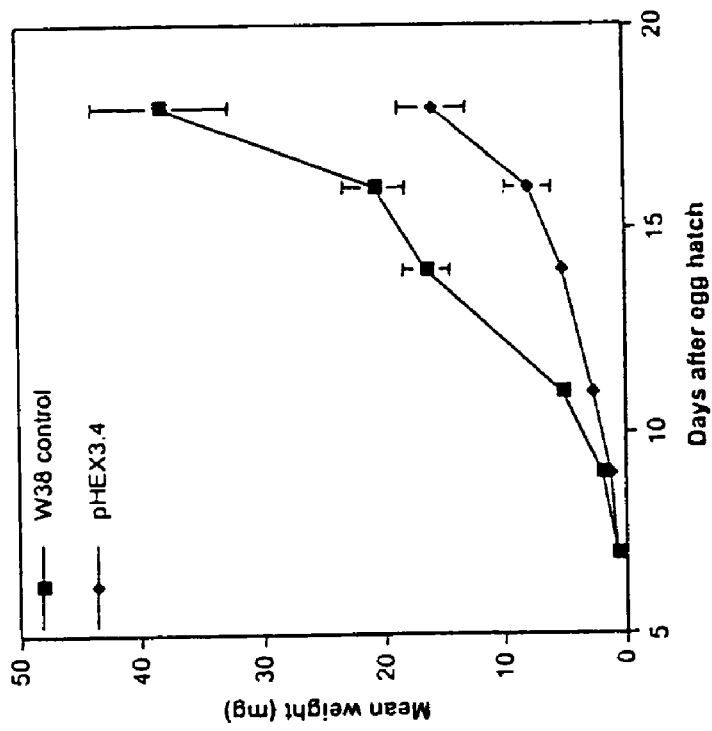
Figure 15D:
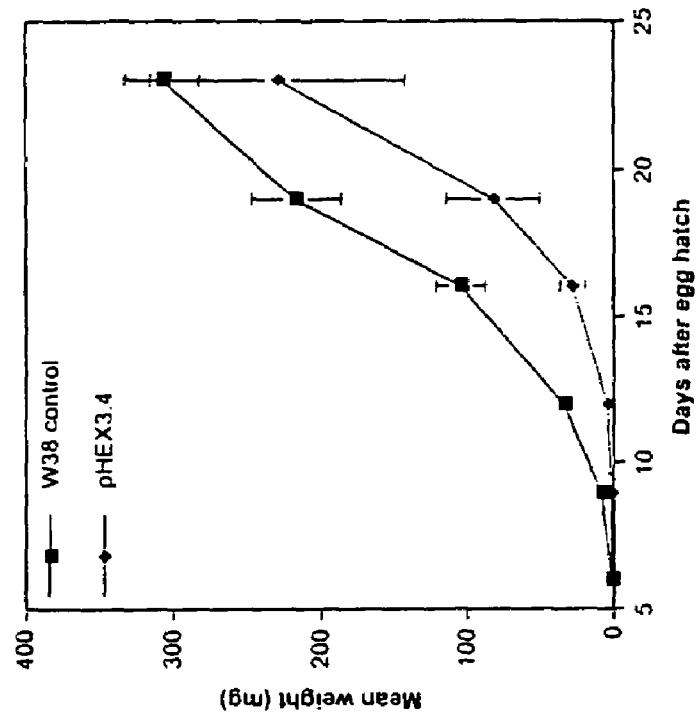
Figure 15C:
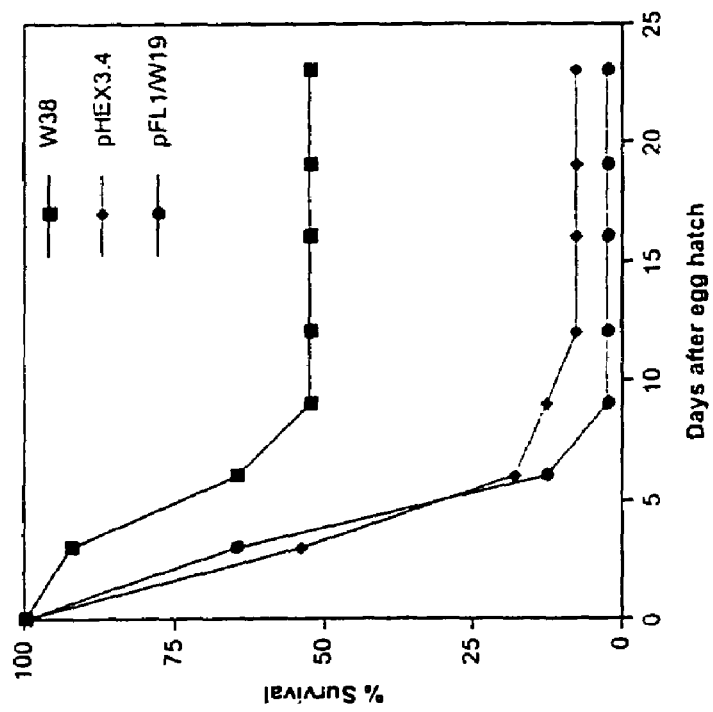

FIG. 14 shows representations of protein blots indicating expression of (A) *N. alata* proteinase inhibitor (NaPI) protein and (B) NaPdf1 protein in transgenic tobacco plants. In A, lane 1: 25 ng NaPI; lane 2: 100 ng NaPI; lane 3: pHEX3.4; lane 4: untransformed W38 and lane 5: pFL1/W19. In B, lane 1: pHEX3.4; lane 2: pFL1/W19; lane 3: untransformed W38 and lane 4: *N. alata* bud extract. (C) indicates expression of NaPdf1 protein in a transgenic cotton plant. Lane 1: 25 ng purified NaPdf1; lane 2: plant CT28.14.1 (transformed with unrelated plasmid) and lane 3: plant CT35.9.1 (transformed with pHEX3).

FIGS. 15A-15D show growth curves for *H. punctigera* and *H. armigera* fed on transgenic *N. tabacum* leaves (lines pHEX3.4 and pFL1/W19) transformed with the NaPdf1 gene and an untransformed W38 parent plant. (15A) Survival of *H. punctigera* larvae, measured between days 2 and 18, (15B) the average mean weight of *H. punctigera* larvae measured between days 7 and 18, (15C) survival of *H. armigera* larvae measured between days 3 and 23, (15D) the average mean weight of *H. armigera* larvae measured between days 6 and 23.

Figure 16:
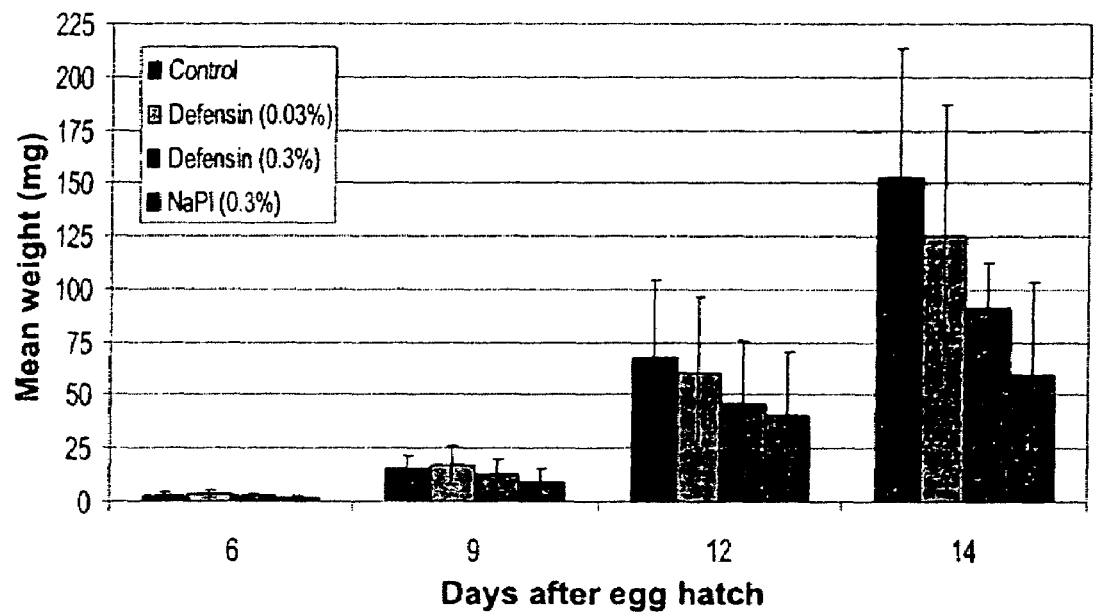

FIG. 16 shows the average mean weight of *H. armigera* larvae fed on artificial diet containing either 0.03% NaPdf1, 0.3% NaPdf1, 0.3% NaPI or casein in place of the test protein (control). Weight of larvae was measured after 6, 9, 12 and 14 days of feeding.

Figure 17:
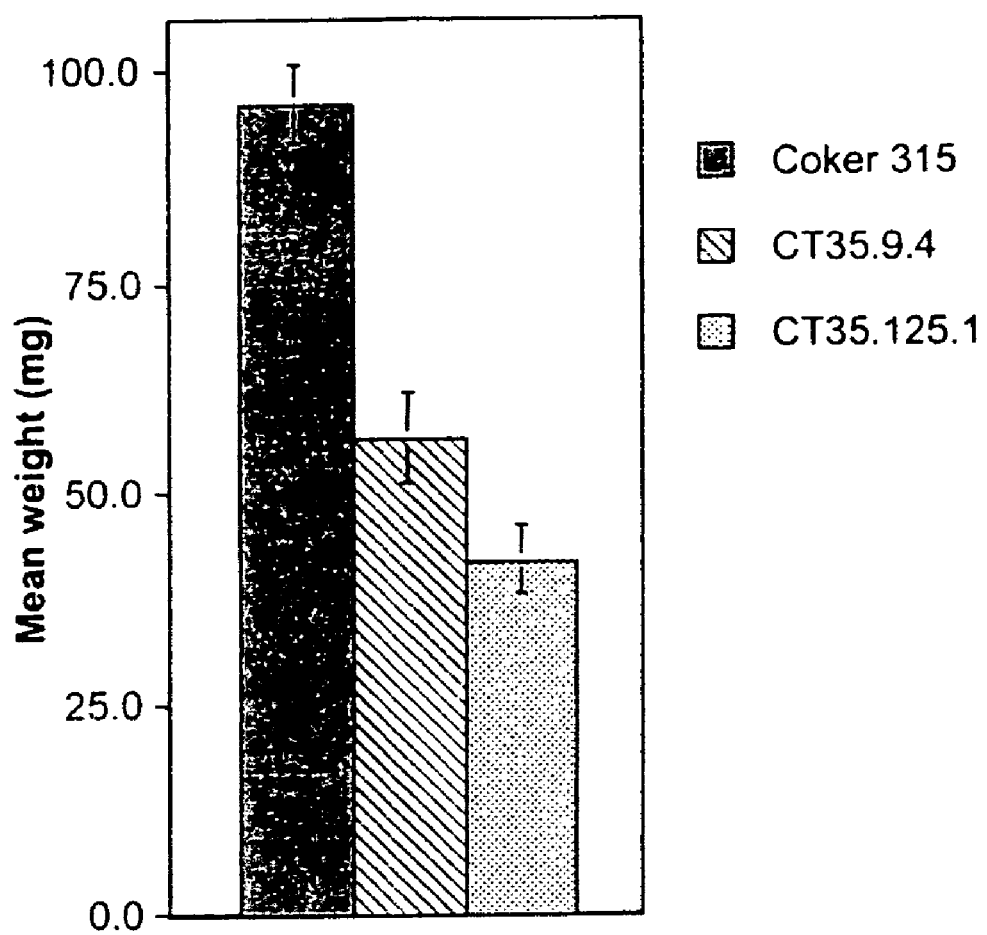

FIG. 17 shows the average mean weight of *H. armigera* larvae fed on transgenic cotton (lines CT35.9.4 and CT35.125.1) transformed with NaPdf1 and non-transformed parent Coker 315 at day 8.

Table 1 is a summary of amino acid and nucleotide sequence identifiers.

Table 2 Artificial diet ingredients used in the feeding trial of *H. armigera*

TABLE 1

| SEQUENCE ID NO: | DESCRIPTION |
|---|---|
| SEQ ID NO: 1 | Primer FST1 |
| SEQ ID NO: 2 | Primer FST2 |
| SEQ ID NO: 3 | Primer PDF1 |
| SEQ ID NO: 4 | Primer PDF2 |

TABLE 1-continued

| SEQUENCE ID NO: | DESCRIPTION |
|---|---|
| SEQ ID NO: 5 | Primer FLOR1 |
| SEQ ID NO: 6 | Primer FLOR2 |
| SEQ ID NO: 7 | cDNA encoding mature domain (NaPdf1) |
| SEQ ID NO: 8 | Amino acid sequence corresponding to SEQ ID NO: 7 |
| SEQ ID NO: 9 | cDNA encoding N-terminal domain (NaPdf1) |
| SEQ ID NO: 10 | Amino acid sequence corresponding to SEQ ID NO: 9 |
| SEQ ID NO: 11 | cDNA encoding C-terminal acidic tail (NaPdf1) |
| SEQ ID NO: 12 | Amino acid sequence corresponding to SEQ ID NO: 11) |
| SEQ ID NO: 13 | cDNA encoding N-terminal + mature domain (NaPdf1) |
| SEQ ID NO: 14 | Amino acid sequence corresponding to SEQ ID NO: 13 |
| SEQ ID NO: 15 | cDNA encoding mature + acidic C-terminal domain (NaPdf1) |
| SEQ ID NO: 16 | Amino acid sequence corresponding to SEQ ID NO: 15 |
| SEQ ID NO: 17 | cDNA encoding NaPdf1 |
| SEQ ID NO: 18 | Amino acid sequence corresponding to SEQ ID NO: 17 |
| SEQ ID NO: 19 | cDNA corresponding to 3' end of NaPdf1 |
| SEQ ID NO: 20 | Amino acid sequence of full FST |
| SEQ ID NO: 21 | Amino acid sequence of full TPP3 |
| SEQ ID NO: 22 | Amino acid sequence of full NTS13 |
| SEQ ID NO: 23 | Amino acid sequence of full PPT |
| SEQ ID NO: 24 | Amino acid sequence of full ATPIIIa |
| SEQ ID NO: 25 | Amino acid sequence of mature domain of FST |
| SEQ ID NO: 26 | Amino acid sequence of mature domain of TPP3 |
| SEQ ID NO: 27 | Amino acid sequence of mature domain of P322 |
| SEQ ID NO: 28 | Amino acid sequence of mature domain of PPT |
| SEQ ID NO: 29 | Amino acid sequence of mature domain of SE60 |
| SEQ ID NO: 30 | Amino acid sequence of mature domain of γ1-H |
| SEQ ID NO: 31 | Amino acid sequence of mature domain of M2A |
| SEQ ID NO: 32 | Amino acid sequence of mature domain of PTH-St1 |
| SEQ ID NO: 33 | Amino acid sequence of mature domain of Rs-AFP1 |
| SEQ ID NO: 34 | Amino acid sequence of mature domain of Rs-AFP2 |
| SEQ ID NO: 35 | Amino acid sequence of mature domain of M1 |
| SEQ ID NO: 36 | Amino acid sequence of mature domain of M2B |
| SEQ ID NO: 37 | Amino acid sequence of mature domain of γ1-P |
| SEQ ID NO: 38 | Amino acid sequence of mature domain of γ2-P |
| SEQ ID NO: 39 | Amino acid sequence of mature domain of 10 kDa |
| SEQ ID NO: 40 | Amino acid sequence of mature domain of SIα2 |
| SEQ ID NO: 41 | Amino acid sequence of mature domain of SIα3 |
| SEQ ID NO: 42 | Amino acid sequence of mature domain of Dm-AMP2 |
| SEQ ID NO: 43 | Amino acid sequence of mature domain of SIα1 |
| SEQ ID NO: 44 | Amino acid sequence of mature domain of P1230 |
| SEQ ID NO: 45 | Amino acid sequence of mature domain of Ah-AMP1 |
| SEQ ID NO: 46 | Amino acid sequence of mature domain of Hs-AFP1 |
| SEQ ID NO: 47 | Amino acid sequence of mature domain of Dm-AMP1 |
| SEQ ID NO: 48 | Amino acid sequence of mature domain of P139 |
| SEQ ID NO: 49 | Amino acid sequence of mature domain of Ct-AMP1 |
| SEQ ID NO: 50 | Amino acid sequence of mature domain of NeThio1 |
| SEQ ID NO: 51 | Amino acid sequence of mature domain of NeThio2 |
| SEQ ID NO: 52 | Amino acid sequence of mature domain of NpThio1 |
| SEQ ID NO: 53 | Amino acid sequence of mature domain of NTS13 |
| SEQ ID NO: 54 | Amino acid sequence of mature domain of PPT |
| SEQ ID NO: 55 | Amino acid sequence of mature domain of ATPIIIa |
| SEQ ID NO: 56 | cDNA encoding mature domain of NaPI |
| SEQ ID NO: 57 | Amino acid sequence corresponding to SEQ ID NO: 56 |
| SEQ ID NO: 58 | Consensus sequence of mature domain of defensin |
| SEQ ID NO: 59 | Consensus sequence of internal domain of defensin |
| SEQ ID NO: 60 | Consensus sequence of C-terminal domain of defensin |
| SEQ ID NO: 61 | Consensus amino acid sequence of defensin |

TABLE 2

| Reagent | Control (10 g) | 0.3% NaPdf1 (3 g) | 0.03% NaPdf1 (3 g) | 0.3% NaPI (3 g) |
|---|---|---|---|---|
| Powdered cotton leaf | 300 mg | 90 mg | 90 mg | 90 mg |
| Yeast | 200 mg | 60 mg | 60 mg | 60 mg |
| Wheatgerm | 240 mg | 72 mg | 72 mg | 72 mg |
| Ascorbic acid | 320 mg | 96 mg | 96 mg | 96 mg |
| Sorbic acid | 8 mg | 2.4 mg | 2.4 mg | 2.4 mg |
| Paraben | 16 mg | 4.8 mg | 4.8 mg | 4.8 mg |
| Linseed oil | 8 µl | 2.4 µl | 2.4 µl | 2.4 µl |
| Wheatgerm oil | 16 µl | 4.8 µl | 4.8 µl | 4.8 µl |
| Casein | 26.5 mg | — | 7.155 mg | — |
| Inhibitor protein (15 mg/ml) | — | 530 µl | 53 µl | 600 µl |
| Distilled water | 1.66 ml | — | 444 µl | — |
| The above reagents were mixed and then added to melted agar | | | | |
| Agar | 320 mg | 96 mg | 96 mg | 96 mg |
| Distilled water | 6 ml | 1.77 ml | 1.8 ml | 1.7 ml |
| Add and mix | | | | |
| Ampicillin (200 mg/ml) | 14 µl | 4.2 µl | 4.2 µl | 4.2 µl |
| Streptomycin (200 mg/ml) | 14 µl | 4.2 µl | 4.2 µl | 4.2 µl |

DETAILED DESCRIPTION OF THE INVENTION

The present invention is predicated in part on the determination of the biological properties of floral-derived, defensin-like molecules from plants and the elucidation of new properties in seed-derived defensins and previously known floral-derived defensins. Importantly, a novel floral-derived, defensin-like molecule is described which exhibits activity against plant pathogens and in particular plant pests such as insects and fungi. Other defensin molecules are described which are contemplated to exhibit anti-insect activity.

Accordingly, one aspect of the present invention provides an isolated nucleic acid molecule comprising a sequence of nucleotides encoding or complementary to a sequence encoding a polypeptide comprising, in its precursor form, an N-terminal signal domain, a mature domain and an acidic C-terminal domain wherein said polypeptide is produced during flower development and its mature domain has activity against one or more plant pests.

This aspect of the present invention does not extend to the defensins FST [flower specific thionin] (Gu et al., {1992; supra}) or TPP3 (Milligan and Gasser, {1995; supra}).

Reference herein to a "polypeptide" includes reference to a peptide or protein. Generally, the polypeptide comprises cysteine residues, the location of which is conserved within members of floral and non-floral-derived defensin molecules. The location of the eight cysteine residues may be defined as follows:

(SEQ ID NO:62)

$a_1 a_2 C_I a_3 a_4 a_5 a_6 a_7 a_8 a_9 a_{10} a_{11} a_{12} C_{II} a_{13} a_{14} a_{15} a_{16} a_{17}$ $C_{III} a_{18} a_{19} a_{20} C_{IV} a_{21} a_{22} a_{23} a_{24} a_{25} a_{26} a_{27} a_{28} a_{29} C_V a_{30}$ $a_{31} a_{32} a_{33} a_{34} a_{35} C_{VI} a_{36} C_{VII} a_{37} a_{38} a_{39} C_{VIII}$ wherein "a" may be the same or different and represents any amino acid residue, the numerical subscript on each "a" represents its position in the amino acid sequence and "C" represents a cysteine residue at a position indicated by its Roman numeral.

Accordingly, another aspect of the present invention is directed to an isolated nucleic acid molecule comprising a sequence of nucleotides encoding or complementary to a sequence encoding a polypeptide comprising, in its precursor form, an N-terminal signal domain, a mature domain and an acidic C-terminal domain wherein said polypeptide is produced during flower development and its mature domain comprises the structure:

(SEQ ID NO:62)

$a_1 a_2 C_I a_3 a_4 a_5 a_6 a_7 a_8 a_9 a_{10} a_{11} a_{12} C_{II} a_{13} a_{14} a_{15} a_{16} a_{17}$ $C_{III} a_{18} a_{19} a_{20} C_{IV} a_{21} a_{22} a_{23} a_{24} a_{25} a_{26} a_{27} a_{28} a_{29} C_V a_{30}$ $a_{31} a_{32} a_{33} a_{34} a_{35} C_{VI} a_{36} C_{VII} a_{37} a_{38} a_{39} C_{VIII}$ wherein "a" may be the same or different and represents any amino acid residue, the numerical subscript on each "a" represents its position in the amino acid sequence and "C" represents a cysteine residue at a position indicated by its Roman numeral and wherein the mature domain has activity against one or more plant pests with the proviso that the polypeptide is not FST or TPP3.

The term "isolated" means that the nucleic acid molecule has undergone at least one step towards being isolated or concentrated or enriched from a more complex solution or source. For example, the term "isolated" includes nucleic acid molecules concentrated or enriched from a biological or chemical sample by precipitation, centrifugation, electrophoresis, micro-filtration, electroporation or chromatography. The term "isolated", however, is in no way intended to limit the nucleic acid molecule to a particular location or state and the present invention extends to the nucleic acid molecule when introduced into the genome of a cell or when it is resident in progeny of cells into which the nucleic acid molecule has been introduced into its genome.

Reference herein to a "nucleic acid molecule" includes reference to DNA or RNA (e.g. mRNA) or DNA/RNA hybrids. A nucleic acid molecule may be regarded inter alia as a genetic molecule, nucleotide sequence or polynucleotide sequence. Preferably, the nucleic acid molecule is a cDNA molecule although the present invention extends to genomic forms of the nucleic acid molecule. The nucleic acid molecule of the present invention may also encode separately the N-terminal signal domain, the mature domain and/or the acidic C-terminal domain or combinations thereof. For example, the nucleic acid molecule may encode for the N-terminal signal domain operably linked to the mature domain. Alternatively, it may encode for the mature domain operably linked to the acidic C-terminal domain. The nucleic acid molecule may also encode all three domains or comprise heterologous domains from other defensin or defensin-like molecules. The development of heterologous defensin-like molecules is encompassed in the present invention and provides a means of broadening the anti-insect or anti-pest spectrum. A heterologous molecule may also comprise multiple mature domains and random repeats of mature domains or other domains required for activity.

Reference herein to production of the polypeptide during "flower development" includes reference to production in flowering parts such as but not limited to production in the pistils, anthers, ovaries, sepals and petals of the flowering region. Preferably, the polypeptide is produced in the epidermal layers of the petals and sepals, the cortical cells of the style and the connective tissue of the anthers.

Accordingly, another aspect of the present invention contemplates an isolated nucleic acid molecule comprising a sequence of nucleotides encoding or complementary to a sequence encoding a polypeptide comprising, in its precursor form, an N-terminal signal domain, a mature domain and an acidic C-terminal domain wherein said polypeptide is produced in the epidermal layers of petals and sepals, the cortical cells of the style and connective tissue of the anthers and its mature domain comprises the structure:

(SEQ ID NO:62)

$a_1a_2C_Ia_3a_4a_5a_6a_7a_8a_9a_{10}a_{11}a_{12}C_{II}a_{13}a_{14}a_{15}a_{16}a_{17}$ $C_{III}a_{18}a_{19}a_{20}C_{IV}a_{21}a_{22}a_{23}a_{24}a_{25}a_{26}a_{27}a_{28}a_{29}C_Va_{30}$ $a_{31}a_{32}a_{33}a_{34}a_{35}C_{VI}a_{36}C_{VII}a_{37}a_{38}a_{39}C_{VIII}$ wherein "a" may be the same or different and represents any amino acid residue, the numerical subscript on each "a" represents its position in the amino acid sequence and "C" represents a cysteine residue at a position indicated by its Roman numeral and wherein the mature domain has activity against one or more plant pests with the proviso that the polypeptide is not FST or TPP3.

In an alternative embodiment, the present invention provides an isolated nucleic acid molecule comprising a sequence of nucleotides encoding or complementary to a sequence encoding a polypeptide comprising two or more mature domains having activity against one or more plant pests and optionally an N-terminal signal domain and optionally an acidic C-terminal domain. The polypeptide according to the latter embodiment would be regarded as a fusion polypeptide.

The location of production of the subject polypeptide may be altered depending on the genetic construct employed to express the nucleic acid molecule. For example, a developmentally regulated and/or tissue-specific promoter may be employed to direct expression of the nucleic acid molecule in any tissue. However, the naturally occurring polypeptide is produced during flower development and more particularly in the tissues of flowers outlined above.

The term "plant pests" is not to confer any limitation as to the type of organism targeted by the subject defensin-like molecule. A plant pest includes an insect, arachnid, microorganism, fungus or virus. In a particularly preferred embodiment, the plant pest is an insect.

In a most preferred embodiment, the defensin-like molecule or its encoding nucleic acid molecule is isolatable from *N. alata* and related species or varieties or strains thereof. The amino acid sequence of the mature domain of the *N. alata* defensin is as follows (in single letter code):

RECKTESNTF PGICITKPPC RKACISEKFT DGHCSKILRR CLCTKPC [SEQ ID NO:8].

The nucleotide sequence encoding SEQ ID NO:8 is set forth in SEQ ID NO:7.

The present invention extends to novel variants of SEQ ID NO:8 such as variants with an amino acid sequence having at least 70% similarity to the sequence set forth in SEQ ID NO:8 or variants encoded by a nucleotide sequence capable of hybridizing to the nucleotide sequence encoding SEQ ID NO:8 (i.e. SEQ ID NO:7) under low stringency conditions at 42° C.

Accordingly, another aspect of the present invention provides an isolated nucleic acid molecule comprising a sequence of nucleotides encoding or complementary to a sequence encoding a polypeptide comprising, in its precursor form, an N-terminal signal domain, a mature domain and an acidic C-terminal domain wherein said mature domain comprises the amino acid sequence set forth in SEQ ID NO:8 or an amino acid sequence having at least about 70% similarity thereto or is encoded by a nucleotide sequence set forth in SEQ ID NO:7 or a nucleotide sequence having at least about 70% similarity thereto or a nucleotide sequence capable of hybridizing to SEQ ID NO:7 or its complementary form under low stringency conditions at 42° C.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al. (*Nucl. Acids Res.* 25: 3389, 1997). A detailed discussion of sequence analysis can be found in Unit 19.3 of Ausubel et al. ("Current Protocols in Molecular Biology" John Wiley & Sons Inc, 1994-1998, Chapter 15).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Reference herein to a "low stringency" includes and encompasses from at least about 0 to at least about 15% v/v formamide and from at least about 1 M to at least about 2 M salt for hybridization, and at least about 1 M to at least about 2 M salt for washing conditions. Generally, low stringency is from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C)% (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The present invention is exemplified herein in relation to the defensin-like molecules from *N. alata*. However, this is done with the understanding that the present invention extends to any novel floral-derived, defensin-like molecule from any plant provided the molecule has activity against plant pests and in particular insects. The present invention extends to derivatives of defensin-like molecules including heterologous molecules as well as the use of known defensins as anti-insect molecules.

Reference to a "defensin-like molecule" is made to highlight the fact that the present invention extends to homologues of defensin molecules.

The present invention further provides genetic constructs for use in expressing defensin-like molecule-encoding nucleotide sequences in plants for the purposes of protecting the plant from plant pests.

Accordingly, another aspect of the present invention provides a genetic construct comprising a promoter or functional equivalent thereof operably linked to a nucleotide sequence encoding a floral-derived, defensin-like molecule having a mature domain comprising the amino acid sequence:

$$a_1a_2C_Ia_3a_4a_5a_6a_7a_8a_9a_{10}a_{11}a_{12}C_{II}a_{13}a_{14}a_{15}a_{16}a_{17}$$
$$C_{III}a_{18}a_{19}a_{20}C_{IV}a_{21}a_{22}a_{23}a_{24}a_{25}a_{26}a_{27}a_{28}a_{29}C_Va_{30}$$
$$a_{31}a_{32}a_{33}a_{34}a_{35}C_{VI}a_{36}C_{VII}a_{37}a_{38}a_{39}C_{VIII}$$
(SEQ ID NO:62)

wherein "a" may be the same or different and represents any amino acid residue, the numerical subscript on each "a" represents its position in the amino acid sequence and "C" represents a cysteine residue at a position indicated by its Roman numeral and wherein said mature domain exhibits inhibitory activity against plant pests such as insect pests with the proviso that the defensin-like molecule is not FST or TPP3.

In a preferred embodiment, the amino acid sequence of the mature domain comprises the amino acid sequence [SEQ ID NO:58]:

$$X_{30}X_{31}CX_{32}X_{33}X_{34}SX_{35}X_{36}FX_{37}GX_{38}CX_{39}X_{40}X_{41}X_{42}X_{43}CX_{44}$$
$$X_{45}X_{46}CX_{47}X_{48}EX_{49}FX_{50}X_{51}GX_{52}CX_{53}X_{54}X_{55}X_{56}X_{57}X_{58}$$
$$CX_{59}CTX_{60}X_{61}C$$

wherein
$X_{30}$=R or Q
$X_{31}$=E, I or T
$X_{32}$=or E
$X_{33}$=T, A or S
$X_{34}$=E, P or Q
$X_{35}$=N, Q or H
$X_{36}$=T or R
$X_{37}$=P, K or H
$X_{38}$=I, L, P or T
$X_{39}$=I, F, S or V
$X_{40}$=T, M, R or S
$X_{41}$=K, D, E or A
$X_{42}$=P or S
$X_{43}$=P, S or N
$X_{44}$=R or A
$X_{45}$=K, T, S or N
$X_{46}$=A, Y or V
$X_{47}$=I, L, Q or H
$X_{48}$=S, K, T or N
$X_{49}$=K or G
$X_{50}$=T, S, I, or V
$X_{51}$=D or G
$X_{52}$=H, R, or N
$X_{53}$=S, P or R
$X_{54}$=K, W, A or G
$X_{55}$=I, L or F
$X_{56}$=L, Q, P or R
$X_{57}$=R or P
$X_{58}$=R or K
$X_{59}$=L or F
$X_{60}$=K, S or R
$X_{61}$=P, N or H The mature domain-encoding sequence may be operably linked to a signal domain comprising the amino acid sequence [SEQ ID NO:59]:

$$MX_1X_2SX_3X_4X_5X_6X_7X_8X_9X_{10}X_{11}X_{12}X_{13}X_{14}X_{15}X_{16}X_{17}X_{18}X_{19}$$
$$X_{20}X_{21}X_{22}X_{23}X_{24}X_{25}X_{26}X_{27}X_{28}AX_{29}$$

wherein
$X_1$=A, G or K
$X_2$=R, N, or L
$X_3$=L, I or M
$X_4$=C, F or R
$X_5$=F or L
$X_6$=M, F or I
$X_7$=A or S
$X_8$=F, T or A
$X_9$=A, L, V or F
$X_{10}$=I, V, L or F
$X_{11}$=L or I
$X_{12}$=A, I or M
$X_{13}$=M, A or F
$X_{14}$=M or L
$X_{15}$=L or I
$X_{16}$=F or V
$X_{17}$=V, T or L
$X_{18}$=A, T or S $X_{19}$=Y or T
$X_{20}$=E or G
$X_{21}$=V or M
$X_{22}$=no amino acid or G
$X_{23}$=no amino acid or P
$X_{24}$=no amino acid, M or V
$X_{25}$=no amino acid or T
$X_{26}$=no amino acid or S
$X_{27}$=no amino acid, A or V
$X_{28}$=Q or E
$X_{29}$=no amino acid or Q In some cases, the mature domain-encoding sequence may be operably linked to an acidic C-terminal domain comprising the sequence [SEQ ID NO:60]:

$$X_{62}X_{63}X_{64}X_{65}X_{66}X_{67}X_{68}X_{69}X_{70}X_{71}X_{72}X_{73}X_{74}X_{75}X_{76}X_{77}X_{78}X_{79}X_{80}X_{81}X_{82}X_{83}X_{84}X_{85}X_{86}X_{87}X_{88}X_{89}X_{90}X_{91}X_{92}X_{93}X_{94}$$

wherein
$X_{62}$=no amino acid or V
$X_{63}$=no amino acid or F
$X_{64}$=no amino acid or D
$X_{65}$=no amino acid or E or K
$X_{66}$=no amino acid or K or I
$X_{67}$=no amino acid or M or S
$X_{68}$=no amino acid or T, I or S
$X_{69}$=no amino acid or K or E
$X_{70}$=no amino acid or T or V
$X_{71}$=no amino acid or G or K
$X_{72}$=no amino acid or A
$X_{73}$=no amino acid or E
$X_{74}$=no amino acid or I or T
$X_{75}$=no amino acid or L
$X_{76}$=no amino acid or A, V or G
$X_{77}$=no amino acid or E
$X_{78}$=no amino acid or E
$X_{79}$=no amino acid or A
$X_{80}$=no amino acid or K
$X_{81}$=no amino acid or T
$X_{82}$=no amino acid or L
$X_{83}$=no amino acid or A or S
$X_{84}$=no amino acid or A or E
$X_{85}$=no amino acid or A or V
$X_{86}$=no amino acid or L or V
$X_{87}$=no amino acid or L
$X_{88}$=no amino acid or E
$X_{89}$=no amino acid or E
$X_{90}$=no amino acid or E
$X_{91}$=no amino acid or I
$X_{92}$=no amino acid or M
$X_{93}$=no amino acid or D or M
$X_{94}$=no amino acid or N or E In yet another embodiment, the defensin-like molecule comprises the sequence [SEQ ID NO:61]:

$$MX_1X_2SX_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}X_{25}X_{26}X_2X_{28}X_{29}X_{30}X_{31}CX_{32}X_{33}X_{34}SX_{35}X_{36}FX_{37}GX_{38}CX_{39}X_{40}X_{41}X_{42}X_{43}CX_{44}X_{45}X_{46}C X_{47}X_{48}X_{49}FX_{50}X_{51}GX_{52}CX_{53}X_{54}X_{55}X_{56}X_{57}X_{58}X_{59}CTX_{60}X_{61}CX_{62}X_{63}X_{64}X_{65}X_{66}X_{67}X_{68}X_{69}X_{70}X_{71}X_{72}X_{73}X_{74}X_{75}X_{76}X_{77}X_{78}X_{79}X_{80}X_{82}X_{83}X_{84}X_{85}X_{86}X_{87}X_{88}X_{89}X_{90}X_{91}X_{92}X_{93}X_{94}$$

wherein
$X_1$=A, G or K
$X_2$=R, N, or L
$X_3$=L, I or M
$X_4$=C, F or R
$X_5$=F or L
$X_6$=M, F or I
$X_7$=A or S
$X_8$=F, T or A
$X_9$=A, L, V or F
$X_{10}$=I, V, L or F
$X_{11}$=L or I
$X_{12}$=A, I or M
$X_{13}$=M, A or F
$X_{14}$=M or L
$X_{15}$=L or I
$X_{16}$=F or V
$X_{17}$=V, T or L
$X_{18}$=A, T or S
$X_{19}$=Y or T
$X_{20}$=E or G
$X_{21}$=V or M
$X_{22}$=no amino acid or G
$X_{23}$=no amino acid or P
$X_{24}$=no amino acid, M or V
$X_{25}$=no amino acid or T
$X_{26}$=no amino acid, I or S
$X_{27}$=no amino acid or A or V
$X_{28}$=Q or E
$X_{29}$=no amino acid or Q
$X_{30}$=R or Q
$X_{31}$=E, I or T
$X_{32}$=K or E
$X_{33}$=T, A or S
$X_{34}$=E, P or Q
$X_{35}$=N, Q or H
$X_{36}$=T or R
$X_{37}$=P, K or H
$X_{38}$=I, L, P or T
$X_{39}$=I, F, S or V
$X_{40}$=T, M, R or S
$X_{41}$=K, D, E or A
$X_{42}$=P or S
$X_{43}$=P, S or N
$X_{44}$=R or A
$X_{45}$=K, T, S or N
$X_{46}$=A, Y or V
$X_{47}$=I, L, Q or H
$X_{48}$=S, K, T or N
$X_{49}$=K or G
$X_{50}$=T, S, I, or V
$X_{51}$=D or G
$X_{52}$=H, R, or N
$X_{53}$=S, P or R
$X_{54}$=K, W, A or G
$X_{55}$=I, L or F
$X_{56}$=L, Q, P or R
$X_{57}$=R or P
$X_{58}$=R or K
$X_{59}$=L or F
$X_{60}$=K, S or R
$X_{61}$=P, N or H
$X_{62}$=no amino acid or V
$X_{63}$=no amino acid or F
$X_{64}$=no amino acid or D
$X_{65}$=no amino acid or E or K
$X_{66}$=no amino acid or K or I
$X_{67}$=no amino acid or M or S
$X_{68}$=no amino acid or T, I or S
$X_{69}$=no amino acid or K or E
$X_{70}$=no amino acid or T or V
$X_{71}$=no amino acid or G or K
$X_{72}$=no amino acid or A
$X_{73}$=no amino acid or E
$X_{74}$=no amino acid or I or T $X_{75}$=no amino acid or L
$X_{76}$=no amino acid or A, V or G
$X_{77}$=no amino acid or E
$X_{78}$=no amino acid or E
$X_{79}$=no amino acid or A
$X_{80}$=no amino acid or K
$X_{81}$=no amino acid or T
$X_{82}$=no amino acid or L
$X_{83}$=no amino acid or A or S
$X_{84}$=no amino acid or A or E
$X_{85}$=no amino acid or A or V
$X_{86}$=no amino acid or L OR v
$X_{87}$=no amino acid or L
$X_{88}$=no amino acid or E
$X_{89}$=no amino acid or E
$X_{90}$=no amino acid or E
$X_{91}$=no amino acid or I
$X_{92}$=no amino acid or M
$X_{93}$=no amino acid or D or M
$X_{94}$=no amino acid or N or E In a preferred embodiment, the genetic construct comprises a nucleotide sequence encoding an amino acid sequence selected from SEQ ID NO:8, SEQ ID NO:14, SEQ ID NO:16 and SEQ ID NO:18.

In a particularly preferred embodiment, the genetic construct comprises a nucleotide sequence selected from SEQ ID NO:7, SEQ ID NO:13, SEQ ID NO:15 and SEQ ID NO:17 or a nucleotide sequence having at least 70% similarity to one or more of SEQ ID NO:8, SEQ ID NO:14, SEQ ID NO:16 and SEQ ID NO:18 or a nucleotide sequence capable of hybridizing to SEQ ID NO:7, SEQ ID NO:13, SEQ ID NO:15 and SEQ ID NO:17 or a complementary form thereof.

Most preferably, the amino acid sequence corresponds to the mature domain and comprises the amino acid sequence set forth in SEQ ID NO:8.

Reference to SEQ ID NO:8, SEQ ID NO:14, SEQ ID NO:16 and SEQ ID NO:18 includes reference to novel variants having at least about 70% similarity to any one of SEQ ID NO:8, SEQ ID NO:14, SEQ ID NO:16 and SEQ ID NO:18. These sequences may also be used to generate multimeric or heterologous molecules.

In accordance with this aspect of the present invention, the construct is for use in generating transgenic plants with increased or enhanced resistance to plant pests (e.g. insect), attack or infestation. Preferably, the construct is used solely for this purpose. The construct may, however, be used for generating recombinant defensin-like molecules in microorganisms such as bacteria. The present invention extends to generic constructs encoding any defensin or defensin-like molecule for use in combating insect infestation. For example, such constructs may be used to generate transgenic plants resistant to insects.

Accordingly, the present invention provides a genetic construct for use in generating insect-resistant transgenic plants, said transgenic plants producing a defensin or defensin-like molecule selected from SEQ ID NO:8, SEQ ID NO:14, SEQ ID NO:16 and SEQ ID NO:18 as well as SEQ ID NO:20 to SEQ ID NO:49 or an amino acid sequence having at least 70% similarity to any one of SEQ ID NO:8, SEQ ID NO:14, SEQ ID NO:16 and SEQ ID NO:18.

As stated above, a plant includes either a monocotyledonous plant or dicotyledonous plant. Particularly, useful plants are food crops such as wheat, rice, barley, soybean and sugarcane. Particularly useful non-food common crops include cotton. Flower and ornamental crops include rose, carnation, petunia, lisianthus, lily, iris, tulip, freesia, delphinium, limonium and pelargonium.

The present invention further contemplates a method for generating a plant with increased or enhanced resistance to a plant pest, said method comprising introducing into the genome of a plant cell or genome of a group of plant cells a genetic construct comprising a promoter or functional equivalent thereof operably linked to a nucleotide sequence encoding a floral-derived, defensin-like molecule having a mature domain comprising the amino acid sequence:

(SEQ ID NO:62)

$a_1a_2C_Ia_3a_4a_5a_6a_7a_8a_9a_{10}a_{11}a_{12}C_{II}a_{13}a_{14}a_{15}a_{16}a_{17}$ $C_{III}a_{18}a_{19}a_{20}C_{IV}a_{21}a_{22}a_{23}a_{24}a_{25}a_{26}a_{27}a_{28}a_{29}C_Va_{30}$ $a_{31}a_{32}a_{33}a_{34}a_{35}C_{VI}a_{36}C_{VII}a_{37}a_{38}a_{39}C_{VIII}$ wherein "a" may be the same or different and represents any amino acid residue, the numerical subscript on each "a" represents its position in the amino acid sequence and "C" represents a cysteine residue at a position indicated by its Roman numeral and wherein said mature domain exhibits inhibitory activity against plant pests such as insect pests and regenerating a plant from said cell or group of cells. In one aspect, this embodiment does not extend to defensin-like molecules FST and TPP3.

The preferred plant pest is an insect.

Preferably, the defensin-like molecule comprises a mature domain having the amino acid sequence [SEQ ID NO:58]:

$X_{30}X_{31}CX_{32}X_{33}X_{34}SX_{35}X_{36}FX_{37}GX_{38}CX_{39}X_{40}X_{41}X_{42}X_{43}CX_{44}$
$X_{45}X_{46}CX_{47}X_{48}EX_{49}FX_{50}X_{51}GX_{52}CX_{53}X_{54}X_{55}X_{56}X_{57}X_{58}$
$CX_{59}CTX_{60}X_{61}C$ wherein
$X_{30}$=R or Q
$X_{31}$=E, I or T
$X_{32}$=K or E
$X_{33}$=T, A or S
$X_{34}$=E, P or Q
$X_{35}$=N, Q or H
$X_{36}$=T or R
$X_{37}$=P, K or H
$X_{38}$=I, L, P or T
$X_{39}$=I, F, S or V
$X_{40}$=T, M, R or S
$X_{41}$=K, D, E or A
$X_{42}$=P or S
$X_{43}$=P, S or N
$X_{44}$=R or A
$X_{45}$=K, T, S or N
$X_{46}$=A, Y or V
$X_{47}$=I, L, Q or H
$X_{48}$=S, K, T or N
$X_{49}$=K or G
$X_{50}$=T, S, I, or V
$X_{51}$=D or G
$X_{52}$=H, R, or N
$X_{53}$=S, P or R
$X_{54}$=K, W, A or G
$X_{55}$=I, L or F
$X_{56}$=L, Q, P or R
$X_{57}$=R or P
$X_{58}$=R or K
$X_{59}$=L or F
$X_{60}$=K, S or R
$X_{61}$=P, N or H More preferably, the mature domain is selected from the amino acid sequences set forth in SEQ ID NO:2, SEQ ID NO:3, SEQ ID NO:4, SEQ ID NO:5, SEQ ID NO:6 and SEQ ID NO:8.

Most preferably, the mature domain comprises an amino acid sequence set forth in SEQ ID NO:8.

Yet another aspect of the present invention provides a method for generating a plant with increased or enhanced resistance to an insect, said method comprising introducing into the genome of a plant cell or genome of a group of plant cells a genetic construct comprising a promoter or functional equivalent thereof operably linked to a nucleotide sequence encoding a defensin-like molecule having a mature domain comprising the amino acid sequence:

$$a_1a_2C_Ia_3a_4a_5a_6a_7a_8a_9a_{10}a_{11}a_{12}C_{II}a_{13}a_{14}a_{15}a_{16}a_{17}$$
$$C_{III}a_{18}a_{19}a_{20}C_{IV}a_{21}a_{22}a_{23}a_{24}a_{25}a_{26}a_{27}a_{28}a_{29}C_{V}a_{30}$$
$$a_{31}a_{32}a_{33}a_{34}a_{35}C_{VI}a_{36}C_{VII}a_{37}a_{38}a_{39}CV_{III}$$

(SEQ ID NO:62)

wherein "a" may be the same or different and represents any amino acid residue, the numerical subscript on each "a" represents its position in the amino acid sequence and "C" represents a cysteine residue at a position indicated by its Roman numeral and wherein said mature domain exhibits inhibitory activity against plant pests such as insect pests and regenerating a plant from said cell or group of cells.

Preferred defensins are selected from SEQ ID NO:8, SEQ ID NO:18 and SEQ ID NO:20 to SEQ ID NO:49.

The mature domains referred to above include fragments and derivatives of these domains.

The term "fragment" as used herein means a portion or a part of the mature domain parent which preferably retains the activity of the parent mature domain. The term "fragment" includes deletions, mutants and small peptides, for example, of at least 5, preferably at least about 10 and more preferably at least about 20 contiguous amino acids, which comprise the above anti-plant pest activity. Peptides of this type may be obtained through the application of standard recombinant nucleic acid techniques or synthesized using conventional liquid or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of an amino acid sequence of the invention with proteinases such as endoLys-C, endoArg-C, endoGlu-C and *Staphylococcus* V8-protease. The digested fragments can be purified, for example, by high performance liquid chromatographic (HPLC) techniques.

By "derivative" is meant a polypeptide that has been derived from the basic sequence by modification, for example, by conjugation or complexing with other chemical moieties or by post-translational modification techniques as would be understood in the art. The term "derivative" also includes within its scope alterations that have been made to a parent sequence including additions or deletions that provide for functionally-equivalent molecules. Accordingly, the term "derivative" encompasses molecules that affect a plant's phenotype in the same way as does the parent amino acid sequence from which it was generated. Also encompassed are polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted or replaced with different amino acids.

The terms "protein", "polypeptide", "peptide" and "an amino acid sequence" are used interchangeably herein to refer to a polymer of amino acid residues and to variants and synthetic analogues thereof. Thus, these terms apply to amino acid polymers in which one or more amino acid residues is a synthetic non-naturally occurring amino acid, such as a chemical analogue of a corresponding naturally occurring amino acid as well as to naturally occurring amino acid polymers.

The terms "variant" and "homologue" refer to nucleotide sequences displaying substantial sequence identity with reference nucleotide sequences or polynucleotides that hybridize with a reference sequence under stringency conditions that are herein defined. The terms "nucleic acid molecule", "nucleotide sequence", "polynucleotide" and "nucleic acid molecule" may be used herein interchangeably and encompass polynucleotides in which one or more nucleotides have been added or deleted or replaced with different nucleotides. In this regard, it is well understood in the art that certain alterations inclusive of mutations, additions, deletions and substitutions can be made to a reference nucleotide sequence whereby the altered polynucleotide retains the biological function or activity of the reference polynucleotide. Such variant polypeptide sequences may encode polypeptides comprising some differences in their amino acid composition but nevertheless encoding a protein having the same or similar activity. The resulting variant polypeptide sequences are encompassed herein. The term "variant" also includes naturally occurring nucleotide allelic variants.

The term "expression" is used in its broadest sense and includes transient, semi-permanent and stable expression, as well as inducible, tissue-specific, constitutive and/or developmentally-regulated expression. Stable, tissue-specific expression is preferred.

To effect expression of the nucleotide sequence of the present invention, it may conveniently be incorporated into a chimeric genetic construct comprising inter alia one or more of the following: a promoter sequence, a 5' non-coding region, a cis-regulatory region such as a functional binding site for transcriptional regulatory protein or translational regulatory protein, an upstream activator sequence, an enhancer element, a silencer element, a TATA box motif, a CCAAT box motif, an upstream open reading frame, transcriptional start site, translational start site, and/or nucleotide sequence which encodes a leader sequence, termination codon, translational stop site and a 3' non-translated region. Preferably, the chimeric genetic construct is designed for transformation of plants as hereinafter described.

The term "5' non-coding region" is used herein in its broadest context to include all nucleotide sequences which are derived from the upstream region of an expressible gene, other than those sequences which encode amino acid residues which comprise the polypeptide product of said gene, wherein 5' non-coding region confers or activates or otherwise facilitates, at least in part, expression of the gene.

The term "gene" is used in its broadest context to include both a genomic DNA region corresponding to the gene as well as a cDNA sequence corresponding to exons or a recombinant molecule engineered to encode a functional form of a product.

As used herein, the term "cis-acting sequence" or "cis-regulatory region" or similar term shall be taken to mean any sequence of nucleotides which is derived from an expressible genetic sequence wherein the expression of the first genetic sequence is regulated, at least in part, by said sequence of nucleotides. Those skilled in the art will be aware that a cis-regulatory region may be capable of activating, silencing, enhancing, repressing or otherwise altering the level of expression and/or cell-type-specificity and/or developmental specificity of any structural gene sequence.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of a structural gene or other nucleic acid molecule, in a plant cell. Preferred promoters according to the invention may contain additional copies of one or more specific regulatory elements to further enhance expression in a cell, and/or to alter the timing of expression of a structural gene to which it is operably connected.

The term "operably connected" or "operably linked" in the present context means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting, i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting, i.e. the genes from which it is derived.

Promoter sequences contemplated by the present invention may be native to the host plant to be transformed or may be derived from an alternative source, where the region is functional in the host plant. Other sources include the *Agrobacterium* T-DNA genes, such as the promoters for the biosynthesis of nopaline, octapine, mannopine, or other opine promoters; promoters from plants, such as the ubiquitin promoter; tissue specific promoters (see, e.g. U.S. Pat. No. 5,459,252 to Conkling et al.; WO 91/13992 to Advanced Technologies); promoters from viruses (including host specific viruses), or partially or wholly synthetic promoters. Numerous promoters that are functional in mono- and dicotyledonous plants are well known in the art (see, for example, Greve, *J. Mol. Appl. Genet.* 1: 499-511, 1983; Salomon et al., *EMBO J.* 3: 1984; Garfinkel et al., *Cell* 27: 143-513, 1983; Barker et al., *Plant Mol. Biol.* 2: 235-350, 1983) including various promoters isolated from plants (such as the Ubi promoter from the maize ubi-1 gene) (see, e.g. U.S. Pat. No. 4,962,028) and viruses (such as the cauliflower mosaic virus promoter, CaMV 35S).

The promoter sequences may include regions which regulate transcription, where the regulation involves, for example, chemical or physical repression or induction (e.g. regulation based on metabolites, light, or other physicochemical factors; see, e.g. WO 93/06710 disclosing a nematode responsive promoter) or regulation based on cell differentiation (such as associated with leaves, roots, seed, or the like in plants; see, e.g. U.S. Pat. No. 5,459,252 disclosing a root-specific promoter). Thus, the promoter region, or the regulatory portion of such region, is obtained from an appropriate gene that is so regulated. For example, the 1,5-ribulose bisphosphate carboxylase gene is light-induced and may be used for transcriptional initiation. Other genes are known which are induced by stress, temperature, wounding, pathogen effects, etc.

The chimeric genetic construct of the present invention may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon.

The 3' non-translated regulatory DNA sequence preferably includes from about 50 to 1,000 nucleotide base pairs and may contain plant transcriptional and translational termination sequences in addition to a polyadenylation signal and any other regulatory signals capable of effecting mRNA processing or gene expression. Examples of suitable 3' non-translated sequences are the 3' transcribed non-translated regions containing a polyadenylation signal from the nopaline synthase (nos) gene of *Agrobacterium tumefaciens* (Bevan et al., *Nucl. Acid Res.* 11: 369, 1983) and the terminator for the T7 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the pea E9 small subunit of the ribulose-1,5-bisphosphate carboxylase (ss-RUBISCO) gene, although other 3' elements known to those of skill in the art can also be employed. Alternatively, 3' non-translated regulatory sequences can be obtained de novo as, for example, described by An (*Methods in Enzymology* 153: 292, 1987), which is incorporated herein by reference.

A chimeric genetic construct can also be introduced into a vector, such as a plasmid. Plasmid vectors include additional DNA sequences that provide for easy selection, amplification and transformation of the expression cassette in prokaryotic and eukaryotic cells, e.g. pUC-derived vectors, pSK-derived vectors, pGEM-derived vectors, pSP-derived vectors, or pBS-derived vectors. Additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the chimeric genetic construct, and sequences that enhance transformation of prokaryotic and eukaryotic cells.

The vector preferably contains an element(s) that permits either stable integration of the vector or a chimeric genetic construct contained therein into the host cell genome, or autonomous replication of the vector in the cell independent of the genome of the cell. The vector, or a construct contained therein, may be integrated into the host cell genome when introduced into a host cell. For integration, the vector may rely on a foreign or endogenous DNA sequence present therein or any other element of the vector for stable integration of the vector into the genome by homologous recombination. Alternatively, the vector may contain additional nucleic acid sequences for directing integration by homologous recombination into the genome of the host cell. The additional nucleic acid sequences enable the vector or a construct contained therein to be integrated into the host cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

For cloning and sub-cloning purposes, the vector may further comprise an origin of replication enabling the vector to replicate autonomously in a host cell such as a bacterial cell. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. The origin of replication may be one having a mutation to make its function temperature-sensitive in a *Bacillus* cell (see, e.g. Ehrlich, *Proc. Natl. Acad. Sci. USA* 75: 1433, 1978).

To facilitate identification of transformed cells, the vector desirably comprises a further genetic construct comprising a selectable or screenable marker gene. The actual choice of a marker is not crucial as long as it is functional (i.e. selective) in combination with the plant cells of choice. The marker gene and the nucleotide sequence of interest do not have to be linked, since co-transformation of unlinked genes as, for example, described in U.S. Pat. No. 4,399,216 is also an efficient process in plant transformation.

Included within the terms selectable or screenable marker genes are genes that encode a "secretable marker" whose secretion can be detected as a means of identifying or selecting for transformed cells. Examples include markers that encode a secretable antigen that can be identified by antibody interaction, or secretable enzymes that can be detected by their catalytic activity. Secretable proteins include, but are not restricted to, proteins that are inserted or trapped in the cell wall (e.g. proteins that include a leader sequence such as that found in the expression unit of extensin or tobacco PR-S); small, diffusible proteins detectable, for example, by ELISA; and small active enzymes detectable in extracellular solution such as, for example, α-amylase, β-lactamase, phosphinothricin acetyltransferase).

Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (neo) gene conferring resistance to kanamycin, paromomycin, G418 and the like as, for example, described by Potrykus et al. (*Mol. Gen. Genet,* 199: 183, 1985); a glutathione-S-transferase gene from rat liver conferring resistance to glutathione derived herbicides as, for example, described in EP-A 256 223; a glutamine synthetase gene conferring, upon overexpression, resistance to glutamine synthetase inhibitors such as phosphinothricin as, for example, described WO 87/05327, an acetyl transferase gene from *Streptomyces viridochromogenes* conferring resistance to the selective agent phosphinothricin as, for example, described in EP-A 275 957, a gene encoding a 5-enolshikimate-3-phosphate synthase (EPSPS) conferring tolerance to N-phosphonomethylglycine as, for example, described by Hinchee et al. (*Biotech.* 6: 915, 1988), a bar gene conferring resistance against bialaphos as, for example, described in WO 91/02071; a nitrilase gene such as bxn from *Klebsiella ozaenae* which confers resistance to bromoxynil (Stalker et al., *Science* 242: 419, 1988); a dihydrofolate reductase (DHFR) gene conferring resistance to methotrexate (Thillet et al., *J. Biol. Chem.* 263: 12500, 1988); a mutant acetolactate synthase gene (ALS), which confers resistance to imidazolinone, sulfonylurea or other ALS-inhibiting chemicals (EP-A-154 204); a mutated anthranilate synthase gene that confers resistance to 5-methyl tryptophan; or a dalapon dehalogenase gene that confers herbicide resistance.

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., *Biochem. Biophys. Res. Comm.* 126: 1259, 1985), which may be employed in calcium-sensitive bioluminescence detection; a green fluorescent protein gene (Niedz et al., *Plant Cell Reports* 14: 403, 1995); a luciferase (luc) gene (Ow et al., *Science* 234: 856, 1986), which allows for bioluminescence detection; a β-lactamase gene (Sutcliffe, *Proc. Natl. Acad. Sci. USA* 75: 3737, 1978), which encodes an enzyme for which various chromogenic substrates are known (e.g. PADAC, a chromogenic cephalosporin); an R-locus gene, encoding a product that regulates the production of anthocyanin pigments (red colour) in plant tissues (Dellaporta et al., *Chromosome Structure and Function*, pp. 263-282, 1988); an α-amylase gene (Ikuta et al., *Biotech.* 8: 241, 1990); a yrosinase gene (Katz et al., *J. Gen. Microbiol.* 129: 2703, 1983) which encodes an enzyme capable of oxidizing tyrosine to dopa and dopaquinone which in turn condenses to form the easily detectable compound melanin; or a xylE gene (Zukowsky et al., *Proc. Natl. Acad. Sci. USA* 80: 1101, 1983), which encodes a catechol dioxygenase that can convert chromogenic catechols.

The selectable marker gene construct may also comprise any one or more of 5' and 3' non-coding regions, cis-regulatory regions, enhancers, activators and the like, as hereinbefore described.

A further aspect of the present invention provides a transfected or transformed cell, tissue or organ from a plant or a transformed microbial cell, said cell, tissue or organ comprising a nucleic acid molecule comprising a sequence of nucleotides encoding or complementary to a sequence encoding a polypeptide comprising, in its precursor form, an N-terminal signal domain, a mature domain and an acidic C-terminal domain wherein said polypeptide is produced during flower development and its mature domain has activity against one or more plant pests.

Preferably, the nucleic acid molecule comprises a sequence of nucleotides encoding or complementary to a sequence encoding a polypeptide comprising, in its precursor form, an N-terminal signal domain, a mature domain and an acidic C-terminal domain wherein said polypeptide is produced during flower development and its mature domain comprises the structure:

(SEQ ID NO:62)

$a_1a_2C_Ia_3a_4a_5a_6a_7a_8a_9a_{10}a_{11}a_{12}C_{II}a_{13}a_{14}a_{15}a_{16}a_{17}$ $C_{III}a_{18}a_{19}a_{20}C_{IV}a_{21}a_{22}a_{23}a_{24}a_{25}a_{26}a_{27}a_{28}a_{29}C_Va_{30}$ $a_{31}a_{32}a_{33}a_{34}a_{35}C_{VI}a_{36}C_{VII}a_{37}a_{38}a_{39}CV_{III}$ wherein "a" may be the same or different and represents any amino acid residue, the numerical subscript on each "a" represents its position in the amino acid sequence and "C" represents a cysteine residue at a position indicated by its Roman numeral and wherein the mature domain has activity against one or more plant pests.

The vectors and chimeric genetic construct(s) of the present invention may be introduced into a cell by various techniques known to those skilled in the art. The technique used may vary depending on the known successful techniques for that particular organism.

Techniques for introducing vectors, chimeric genetic constructs and the like into cells include, but are not limited to, transformation using $CaCl_2$ and variations thereof, direct DNA uptake into protoplasts, PEG-mediated uptake to protoplasts, microparticle bombardment, electroporation, microinjection of DNA, microparticle bombardment of tissue explants or cells, vacuum-infiltration of tissue with nucleic acid, and T-DNA-mediated transfer from *Agrobacterium* to the plant tissue.

For microparticle bombardment of cells, a microparticle is propelled into a cell to produce a transformed cell. Any suitable ballistic cell transformation methodology and apparatus can be used in performing the present invention. Exemplary procedures are disclosed in Sanford and Wolf (U.S. Pat. Nos. 4,945,050, 5,036,006, 5,100,792, 5,371,015). When using ballistic transformation procedures, the genetic construct may incorporate a plasmid capable of replicating in the cell to be transformed.

Examples of microparticles suitable for use in such systems include 0.1 to 10 μm and more particularly 10.5 to 5 μm tungsten or gold spheres. The DNA construct may be deposited on the microparticle by any suitable technique, such as by precipitation.

Plant tissue capable of subsequent clonal propagation, whether by organogenesis or embryogenesis, may be transformed with a chimeric genetic construct of the present invention and a whole plant generated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g. apical meristem, axillary buds, and root meristems), and induced meristem tissue (e.g. cotyledon meristem and hypocotyl meristem).

The regenerated transformed plants may be propagated by a variety of means, such as by clonal propagation or classical breeding techniques. For example, a first generation (or T1) transformed plant may be selfed to give a homozygous second generation (or T2) transformant and the T2 plants further propagated through classical breeding techniques.

Accordingly, this aspect of the present invention, insofar as it relates to plants, further extends to progeny of the plants engineered to express the nucleic acid molecule encoding the defensin-like molecule or a variant or homologue thereof as well as vegetative, propagative and reproductive parts of the plants, such as flowers (including cut or severed flowers), parts of plants, fibrous material from plants (for example, cotton) and reproductive portions including cuttings, pollen, seeds and callus.

Another aspect of the present invention provides a genetically modified plant cell or multicellular plant or progeny thereof or parts of a genetically modified plant capable of producing a heterologous defensin-like molecule as herein described wherein said transgenic plant is resistant or has reduced sensitivity to plant pests such as insects.

More particularly, the present invention provides a genetically modified plant cell or multi-cellular plant or progeny or parts thereof comprising the amino acid sequence set forth in SEQ ID NO:8 or a fragment or derivative.

The term "genetically modified" is used in its broadest sense and includes introducing gene(s) into cells, mutating gene(s) in cells and altering or modulating the regulation of gene(s) in cells.

The genetic construct may be a single molecule or multiple molecules such as a set of molecules such that a combination may comprise nucleotide sequences capable of encoding other anti-plant pathogen molecules such as but not limited to a proteinase inhibitor or precursor thereof. Proteinase inhibitors such as serine proteinase inhibitors frequently accumulate in storage organs and in leaves in response to wounding. The inhibitory activities of the proteins are directed against a wide range of proteinases of microbial and animal origin.

Accordingly, another aspect of the present invention comprises one or more genetic constructs alone or in combination comprising a first promoter operably linked to a first nucleotide sequence wherein said first nucleotide sequence encodes a defensin-like molecule or part therof capable of inhibiting a plant pest such as an insect, said construct further comprising a second promoter operably linked to a second nucleotide sequence wherein said second nucleotide sequence encodes a proteinase inhibitor or precursor thereof.

In one embodiment, the defensin-like molecule and/or its encoding DNA sequence is selected from SEQ ID NO:7 to SEQ ID NO:18. In another embodiment, the defensin-like molecule and/or its encoding DNA sequence is selected from SEQ ID NO:7 to SEQ ID NO:18 or SEQ ID NO:20 to SEQ ID NO:24. The defensin-like molecule and/or its encoding DNA sequence defined by SEQ ID NO:7 or SEQ ID NO:8 is particularly preferred. In yet another embodiment, the defensin-like molecule and/or its encoding DNA sequence is selected from SEQ ID NO:7 or SEQ ID NO:8, SEQ ID NO:17 or SEQ ID NO:18 or SEQ ID NO:20 to SEQ ID NO:55.

In another embodiment, the proteinase inhibitor is a serine proteinase inhibitor of type I or type II. A particularly useful proteinase inhibitor comprises the amino acid sequence encoding the nucleotide sequence set forth in SEQ ID NO:57 and SEQ ID NO:56, respectively. This molecule is also described in International Patent Application No. PCT/AU93/00659 (WO 94/13810).

The present invention extends to plants and plant parts including reproductive parts of plants which carry all or part of a genetic construct which confers on the plant or plant parts resistance or reduced sensitivity to plant pests including insects and optionally a second genetic construct as described above.

The present invention further contemplates a composition comprising a defensin or defensin-like molecule alone or in combination with another agent such as a proteinase inhibitor. The composition is particularly useful for topical application to plants such as cotton plants, to assist in controlling insect infestation.

The present invention further contemplates a promoter associated with the genomic form of the nucleotide sequence set forth in SEQ ID NO:7. According to this aspect of the present invention, there is provided an isolated nucleic acid molecule having promoter activity and corresponding to the genomic region in a plant genome which is operably linked to a nucleotide sequence corresponding to all or part of SEQ ID NO:7 or a nucleotide sequence having 70% similarity thereof or a nucleotide sequence capable of hybridizing to SEQ ID NO:7 or its complementary form.

The present invention is further described by the following non-limiting Examples.

EXAMPLE 1

Preparation of Plant Material

*Nicotiana alata* (Link et Otto) plants of mixed self-incompatibility genotype were maintained under glasshouse conditions as described by Anderson et al. (*Plant Cell* 1: 483-491, 1989). Flowers and floral buds were harvested and within two hours, pistils, ovaries and anthers were removed with forceps and a scalpel blade, while petals were separated by hand. Pollen grains from dehisced anthers and whole flowers at various stages of development were also collected. The tissues were frozen in liquid nitrogen and stored at −70° C. until use.

EXAMPLE 2

Cloning of cDNA from *N. alata*

(a) Isolation of RNA

Total RNA was prepared by grinding 70 pistils (1.3 g) from *N. alata* flowers at the petal coloration stage of development to a fine powder with a sterile mortar and pestle in the presence of liquid nitrogen. The RNA was extracted with TRIzol (trademark) Reagent (Gibco BRL) according to the manufacturer's instructions (see Gibco BRL form #3796, TRIzol (trademark) Reagent Total RNA isolation reagent).

(b) cDNA Synthesis and Amplification of Floral Defensin Sequence by PCR

First strand cDNA was prepared from total pistil RNA using the Superscript Preamplification System (Gibco BRL). Oligonucleotide primers used for PCR were specific to the DNA sequence published for the Flower Specific Thionin (FST, Gu et al. [1992; supra] from *N. tabacum*.

[SEQ ID NO:1]
Primer FST1: 5' GGAATTCCATATGGCTCGCTCCTTGTGC 3'

[SEQ ID NO:2]
Primer FST2: 5' GCGGATCCTCAGTTATCCATTATCTCTTC 3'

Primer FST1 and primer FST2 matched the sequence of FST between nucleotides 49-66, and 346-363 respectively. A cDNA clone encoding the *N. alata* floral defensin precursor (NaPdf1) was obtained by PCR amplification using the single-stranded cDNA as a template. The NaPdf1 product was cloned into the pBluescript SK+ II (Stratagene) vector (pBS-NaPdf1) for sequencing. The product is 318 bp in length and encodes the complete coding sequence without the 5' and 3' untranslated regions.

The NaPdf1 PCR product was subsequently used to screen a previously constructed *N. alata* pistil cDNA library (Schultz et al., *Plant Mol Biol* 35: 833-845, 1997). The membranes were probed with NaPdf1 cDNA labelled with [$\alpha^{32}$P]dCTP using random nonamer priming (Megaprime (trademark) DNA labelling kit, Amersham Life Technologies). Unincorporated [$\alpha^{32}$P]dCTP was removed using a Bio-Rad Bio-Spin column 30 as described in the manufacturer's instructions. The blot was hybridized with the probe in a solution of 50% v/v formamide, 5×SSPE, 5× Denhardt's solution and 200 μg/ml herring sperm DNA at 42° C. for 16 h before unbound probe was removed by washing twice with 2×SSPE and 0.1% w/v SDS at room temperature for 10 min. Hybridized probe was visualized by exposing the blot to x-ray film. Positive clones from the screen were excised and sequenced.

EXAMPLE 3

NaPdf1 Gene Expression (a) RNA Gel Blot Analysis

Figure 2:
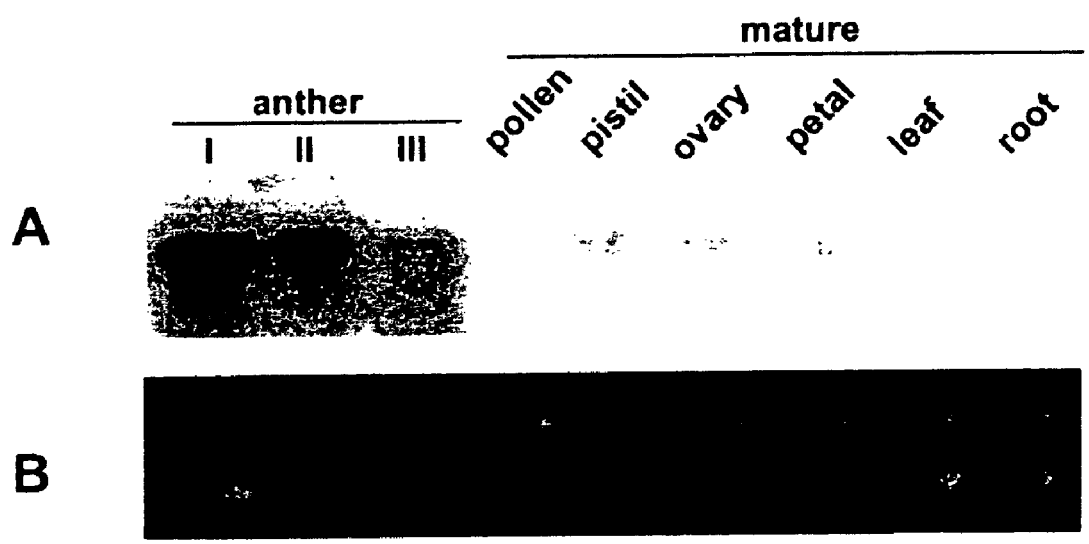
FIG. 2 is a diagrammatic representation of an RNA gel blot analysis of NaPdf1 expression in various tissues of *Nicotiana alata*. Total RNA was isolated from anthers at stages I (5-10 mm buds), II (20-30 mm buds) and III (50-70 mm buds) of development, from pollen grains, and from mature pistil, ovary, petal, leaf and root tissues of *N. alata* (self-incompatibility genotype, $S_2S_2$), as shown in panel A. Panel B shows the same RNA samples following staining with ethidium bromide.

Total RNA was isolated from anthers at stages I (5-10 mm buds), II (20-30 mm buds) and III (50-70 mm buds) of development, from pollen grains and from mature pistil, ovary, petal, leaf and root tissues of *N. alata* (self-incompatibility genotype, $S_2S_2$). The RNA samples (12.5 μg) were fractionated on a denaturing 1% w/v agarose-formaldehyde gel and transferred to Hybond-N (Amersham Life Sciences) membrane. Production of a radio-labelled NaPdf1 cDNA probe and hybridization conditions were as described for the screening of the cDNA library, in Example 2(b), above. Stringency washes were in 0.2×SSPE, 0.1% SDS at 45° C. and 55° C. for 30 min, respectively. Results are shown in FIG. 2. Hybridized probe was visualized by exposing the blot to a storage phosphor screen for 24 h. The results were read in a Molecular Dynamics 400B phosphorimager, using the ImageQuant software.

(b) In Situ Hybridization

In situ hybridization was performed essentially as described by Drews et al. (*Cell* 65: 991-1002, 1991) and Cox and Goldberg (In: *Analysis of plant genes expression* In *Plant Molecular Biology: A Practical Approach*. C. H. Shaw (ed), pp. 1-34, IRL Press, Oxford, United Kingdom, 1988). $^{35}$S-labelled sense and antisense RNA probes were produced by linearising the pBS-NaPdf1 DNA with EcoRI and BamHI and transcribing with T7 and T3 RNA polymerases respectively (Ausubel et al. [1994; supra]; Drews et al. [1991; supra]) Ten mm flower buds were excised from the plant and fixed in 50% v/v ethanol, 5% v/v acetic acid and 3.7% v/v formaldehyde. The fixed tissues were dehydrated and embedded in paraffin (Sigma). The tissues were then sliced into 10 μm sections and attached to Superfrost*/plus slides (Menzel-Glaser, Germany). The sections were treated with xylene followed by hydration, proteinase K treatment, acetylation and dehydration. The $^{35}$S-labelled sense and antisense riboprobes were hydrolyzed to about 100 nucleotides in length and hybridized to the sections at 42° C. for 17 h. The sections were then treated with ribonuclease A and washed, before the slides were coated with film emulsion. The sections were developed after a 1 week exposure.

Figure 3:
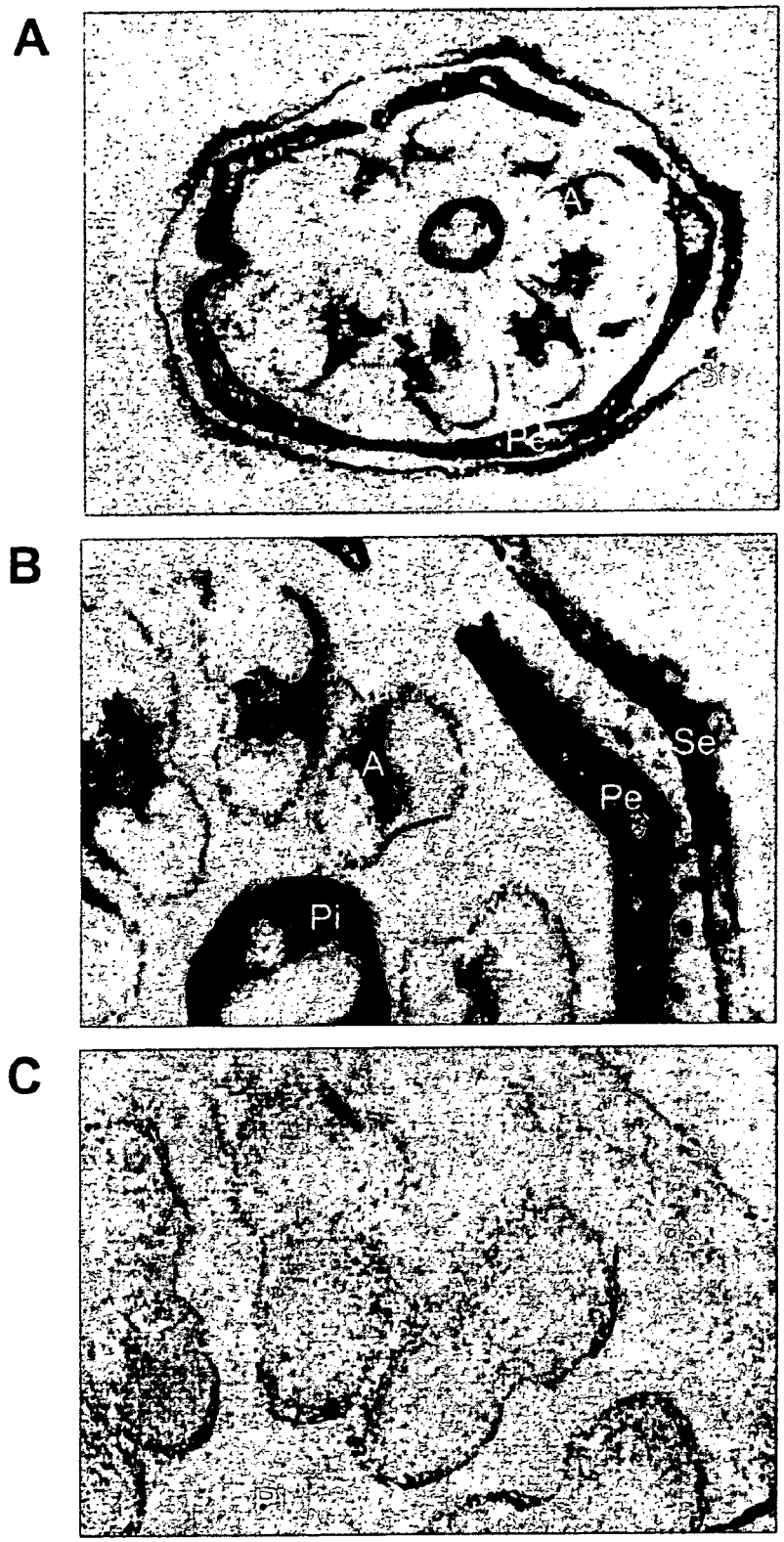
FIG. 3 is a representation of an autoradiograph showing in situ localization of NaPdf1 RNA. (A) A transverse section of a 1 cm long flower bud, after hybridization with a $^{35}$S-labelled NaPdf1 anti-sense RNA probe. Heavy labelling of the epidermal cells of the petal (Pe) and sepal (Se), the cortical cells of the pistil (Pi) and the connective tissue of the anther (A) can be detected. (B) The same section as in A, under higher magnification. (C) A similar section as in B, after hybridization with a $^{35}$S-labelled NaPdf1 sense RNA probe. No labelling is seen in any of the cells of the pistil (Pi), anther (A), petal (Pe) or sepal (Se).

Results indicated that NaPdf1 transcript accumulated in the connective tissue of the anthers, the cortical cells of the style and in the epidermal cells of the petals and sepals (refer to FIG. 3). This accumulation pattern is consistent with the encoded protein playing a role in the defense of the reproductive organs.

EXAMPLE 4

Figure 8:
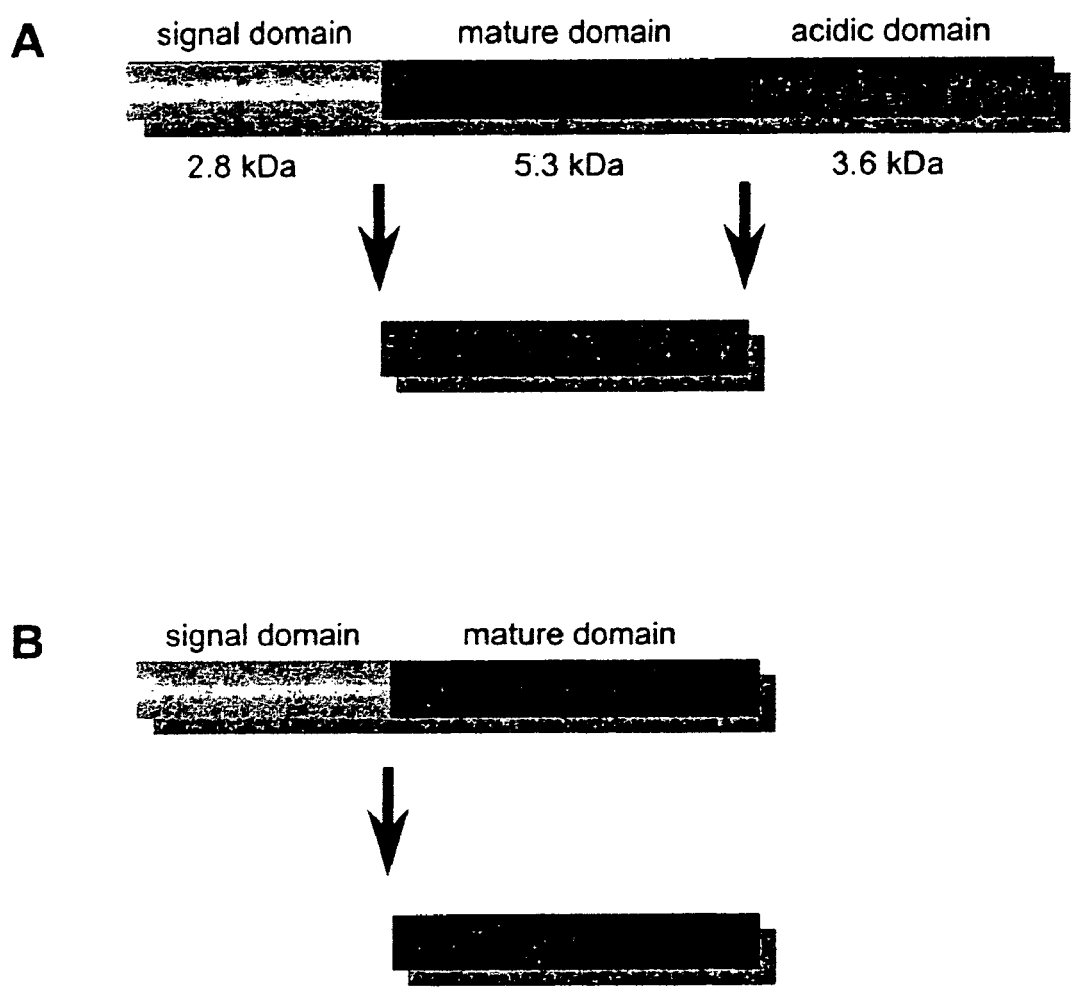
FIG. 8 is a schematic representation of the precursor proteins predicted from cDNA clones that encode floral and seed defensins. (A) Some floral defensins are produced as precursor proteins with three distinct domains: an ER signal sequence (left section of the diagram), a central basic domain (middle of the diagram) and a C-terminal domain rich in acidic amino acids (right section of the diagram). The predicted sizes of each of these domains for the *N. alata* defensin are shown below the diagram. The mature floral defensin is released after proteolytic cleavage (arrowed). (B) cDNAs for seed derived defensins encode proteins with an ER signal sequence and a basic defensin domain, but no C-terminal acidic domain.

Protein Expression for Antibody Production (a) Molecular Cloning and Bacterial Protein Expression The pBS-NaPdf1 (see Example 2(b)) was used to PCR amplify a DNA fragment encoding the proprotein domains (NaproPdf1, precursor minus the N-terminal ER signal domain). For a schematic representation of the structure, see FIG. 8. The NaproPdf1 DNA fragment was obtained using oligonucleotide primers PDF1 and PDF2 which incorporated a BamHI and SacI restriction site for subsequent cloning, respectively.

[SEQ ID NO:3]
Primer PDF1: 5' CCGGATCCAGAGAATGCAAAACAG 3'

[SEQ ID NO:4]
Primer PDF2: 5' GGGAGCTCTTAGTTATCCATTATCTC 3'

The NaproPdf1 DNA fragment was cloned directly from PCR into the pGEM-T vector (Promega) according to the manufacturer's instructions and subcloned into the pQE30 (Qiagen) vector for protein expression in E. coli strain M15 bacteria (Qiagen).

The NaproPdf1 protein was expressed in bacteria, as a fusion with an N-terminal hexahistidine tag. Transformed E. coli cells were grown in LB broth containing ampicillin (100 μg/ml) and kanamycin (12.5 μg/ml) to an absorbance reading of ~0.8 at 595 nm before induction with isopropyl β-D-thiogalactopyranoside (IPTG, 1 mM) for 6 h. Cells were pelleted by centrifugation and resuspended in lysis buffer (10 mM Tris-HCl pH 8.0, 100 mM sodium phosphate buffer pH 8.0, 8 M urea; 30 ml of lysis buffer/liter of culture) before incubation for 30 min on ice. The lysate was then passed through an 18-gauge needle before the supernatant was collected by centrifugation (25,000 g, 15 min, 4° C.). The hexa-histidine-tagged proteins (6H.NaproPdf1) were purified from lysed bacterial cells using the denaturing protein purification protocol outlined in the Clontech TALON (trademark) Metal Affinity Resin User Manual (PT1320-1). Bound proteins were eluted from the resin in 100 mM EDTA, pH 8.0. The eluted proteins were lyophilized. Protein extracts corresponding to various steps in the purification procedure were analyzed by SDS-PAGE (15% w/v polyacrylamide) and visualized by staining with Coomassie Blue (see FIG. 4A). A sample of the metal affinity purified 6H.NaproPdf1 protein was applied to an Aquapore RP300 reverse-phase C8 analytical column (4.6×100 mm, Brownlee) using a Waters model 510 pump and a Waters model 481UV detector. Protein was eluted with a gradient of 0-100% buffer B (60% v/v acetonitrile in 0.089% v/v trifluoroacetic acid), over 30 min. The protein eluted in a single peak (FIG. 4B) and N-terminal sequence and mass spectrometry confirmed that it was 6H.NaproPdf1.

(b) Production of a Polyclonal Antiserum

The bacterially-expressed 6H.NaproPdf1 protein (1.3 mg) was conjugated to keyhole limpet hemocyanin (KLH, 0.3 mg, Sigma) with glutaraldehyde as described by Harlow and Lane (*Antibodies: A Laboratory Manual*. Cold Springs Harbor Laboratory Press, Cold Springs Harbor, N.Y., 1988), prior to injection into a rabbit. The conjugated protein was then dialyzed against PBS overnight. The protein conjugate (100 μg, in 1 mL PBS) was mixed with an equal volume of Freund's complete adjuvant (Sigma). The primary immunization consisted of 4×400 μL subcutaneous injections. Booster immunizations were administered 5 and 9 weeks later and contained the protein conjugate (100 μg, in 1 mL PBS) mixed with Freund's incomplete adjuvant (Sigma). Pre-immune serum was collected prior to injection while immune serum was collected 9 days after the second immunization.

(c) Protein A Purification of IgGs from Whole Sera

The IgG fraction in the pre-immune serum and immune serum were purified using a Protein-A Sepharose CL-4B column (2.5 mL, Pharmacia) according to the manufacturer's instructions. The pre-immune serum (2 mL) was diluted in an equal volume of 0.1 M Tris-HCl (pH 7.5) and loaded onto the column which had been equilibrated in 0.1 M Tris-HCl (pH 7.5). The eluent was collected and re-applied three times. The column was washed with 80 mL of 0.1 M Tris-HCl (pH 7.5), followed by 80 mL of 0.01 M Tris-HCl (pH 7.5) to remove any unbound material. The IgGs were eluted with 100 mM glycine (pH 2.5) and 500 μL fractions were collected into microfuge tubes containing 50 μL of 1 M Tris-HCl (pH 8.8). Fractions containing the IgGs were pooled and dialysed extensively with PBS at 4° C. The Protein-A Sepharose column was regenerated by washing with 0.1 M Tris-HCl (pH 7.5). When the pH reached 7.5, the immune serum (3 mL, second bleed) was applied and purified as described for the pre-immune serum.

(d) SDS-Polyacrylamide Gel Electrophoresis

Figure 5:
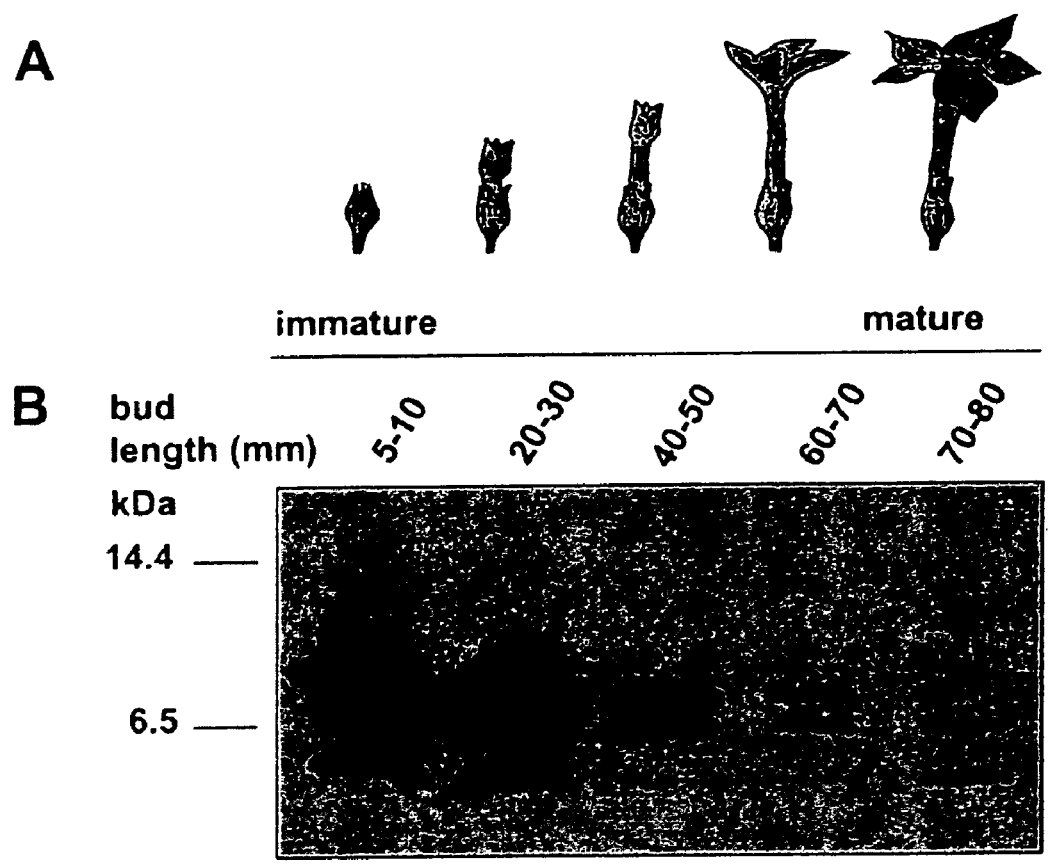
FIG. 5 is a representation showing immunoblot analysis of plant extracts with the antibodies raised to the bacterially expressed pro-defensin (6H.NaproPdf1) encoded by the NaPdf1 cDNA clone. (A) A diagrammatic representation of the five stages of developing. *N. alata* flowers. (B) A representation of an immunoblot of buffer soluble proteins (60 μg) from flowers at the stages of development shown in (A). Proteins were separated on a 15% w/v SDS-polyacrylamide gel prior to transfer to nitrocellulose (0.22 μm) and immunoblotting with antibodies (1:2500) raised against bacterially expressed 6H.NaproPdf1 (see FIG. 4). The antibodies bound specifically to three proteins. The smallest is the predicted size of mature defensin (~5 kDa) while the two larger species are probably the precursor and a processing intermediate. For details, see Examples 4 and 5.

Buffer (50 mM Tris-HCl pH 8.0, 10 mM EDTA, 0.5 M NaCl) soluble protein samples (60 μg), from the stages of N. alata flower development shown in FIG. 5(A), were subjected to SDS-polyacrylamide gel electrophoresis (SDS-PAGE, with 4% w/v stacking and 15% resolving w/v polyacrylamide gels) (Laemmli, *Nature* 227: 680-685, 1970) using a Mini Protean II Electrophoresis apparatus (Bio-Rad). The proteins were visualized by coomassie blue staining and compared to Broad Range molecular weight markers (6.5-200 kDa) from Bio-Rad.

(e) Immunoblot Analysis

Proteins separated by SDS-PAGE were transferred to a nitrocellulose membrane (Micron Separations Inc., 0.22 μm pore size) using a Mini-Protean II Trans-Blot apparatus (Bio-Rad) in transfer buffer (48 mM Tris (hydroxymethyl) aminomethane, 192 mM glycine, 20% v/v methanol). After transfer at 100 V for 1 h, the membrane was fixed in isopropanol for 1 min followed by a 5 min wash in TBS (20 mM Tris-HCl, 150 mM NaCl, pH 8.0). Molecular weight markers were visualized by amido black staining (1:50 dilution of 0.1% w/v amido black in 40% v/v methanol and 10% v/v acetic acid).

The membrane was blocked for 1 h in 5% w/v skim milk followed by incubation with anti-6H.NaproPdf1 antibodies for 1.5 h (1:2500 dilution in TBS). The membrane was washed 3×10 min in TBST (0.1% v/v Tween 20 in TBS) before incubation with donkey anti-rabbit IgG conjugated to horseradish peroxidase for 1.5 h (Amersham Pharmacia Biotech; 1:5000 dilution in TBS). Three further 10 min washes were performed before the immunoblot was treated with Enhanced Chemi-Luminescence (ECL) detection reagents (Amersham Pharmacia Biotech) according to the manufacturer's instructions. Immunoblots were exposed to ECL Hyperfilm (Amersham Pharmacia Biotech). Three proteins reacted specifically with the antibodies and the levels of protein were most abundant during the early stages of development (refer to FIG. 5B).

The lower molecular weight species was confirmed as the mature defensin by mass spectrometry (5.3 kDa) and N-terminal amino acid sequencing; refer to Example 5(c), below.

EXAMPLE 5

Purification from Floral Buds (a) Protein Extraction

Mature NaPdf1 protein was extracted from flowers using a modification of a procedure for extraction of thionins from barley flour (Ozaki et al., *J. Biochem.* 87: 549-555, 1980). Whole *N. alata* flowers up to the petal coloration stage of flower development (5-50 mm, 650 g wet weight) were ground to a fine powder with liquid nitrogen using a mortar and pestle and processed further in an Ultra-Turrax homogenizer (Janke & Kunkel, Germany) in 50 mM sulfuric acid (3 mL/g weight). After stirring for 1 h at 4° C., insoluble material was removed by filtration through Miracloth (Calbiochem) followed by centrifugation (25,000×g, 15 min, 4° C.). The slurry was adjusted to pH 7.8 by the slow addition of 10 M NaOH and stirred for 1 h at 4° C. before removal of precipitated material by centrifugation (25,000×g, 15 min, 4° C.). Solid ammonium sulfate was added to 80% (w/v) saturation and the mixture was stirred for 4 h or overnight at 4° C. to precipitate the defensin protein. The precipitate was collected by centrifugation and was dissolved in 50 mL of gel filtration buffer (150 mM KCl, 10 mM Tris-HCl, pH 8.0) prior to heating at 90° C. for 10 min. Following centrifugation, the supernatant was loaded onto a Sephadex G-50 gel filtration column (85×2.54 cm, Pharmacia). Fractions (50 mL) were collected and analyzed by immunoblotting with anti-6H.NaproPdf1 antibodies. Fractions containing NaPdf1 were pooled, concentrated by rotary evaporation at 45° C. and filtered through a 0.22 µm syringe filter (Millipore) before further purification by RP-HPLC.

(b) Reverse-Phase High Performance Liquid Chromatography

Figure 6:
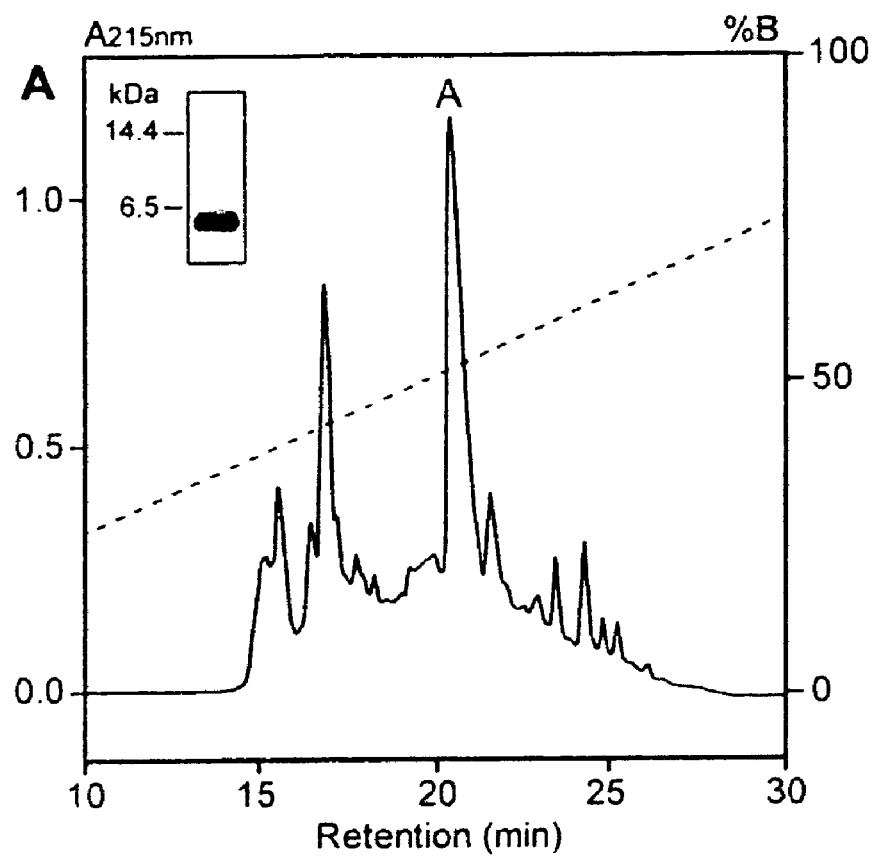
FIG. 6 shows the purification of mature *N. alata* defensin from flower buds. (A) Reverse-phase HPLC on an Aquapore RP-300 C8 column (4.6 mm×100 mm, Brownlee). Proteins were extracted from flower buds and partially purified by gel filtration chromatography (see Example 5) before RP-HPLC. Proteins were applied in 0.1% v/v TFA and eluted with 60% v/v acetonitrile in 0.089% v/v TFA (buffer B) according to the gradient 0-100% buffer B over 40 min at a flow rate of 1 mL/min. Eluted proteins were detected by absorbance at 215 nm. (Inset) Protein in Peak A separated by 15% w/v SDS-PAGE and immunoblotted with anti-6H.NaproPdf1 antibodies (Example 4). (B) N-terminal sequencing and mass spectrometry confirmed the identity of Peak A as the mature defensin domain encoded by the NaPdf1 cDNA clone. "x" corresponds to an unassigned amino acid that is probably a cysteine as predicted from the cDNA sequence
Figure 7:
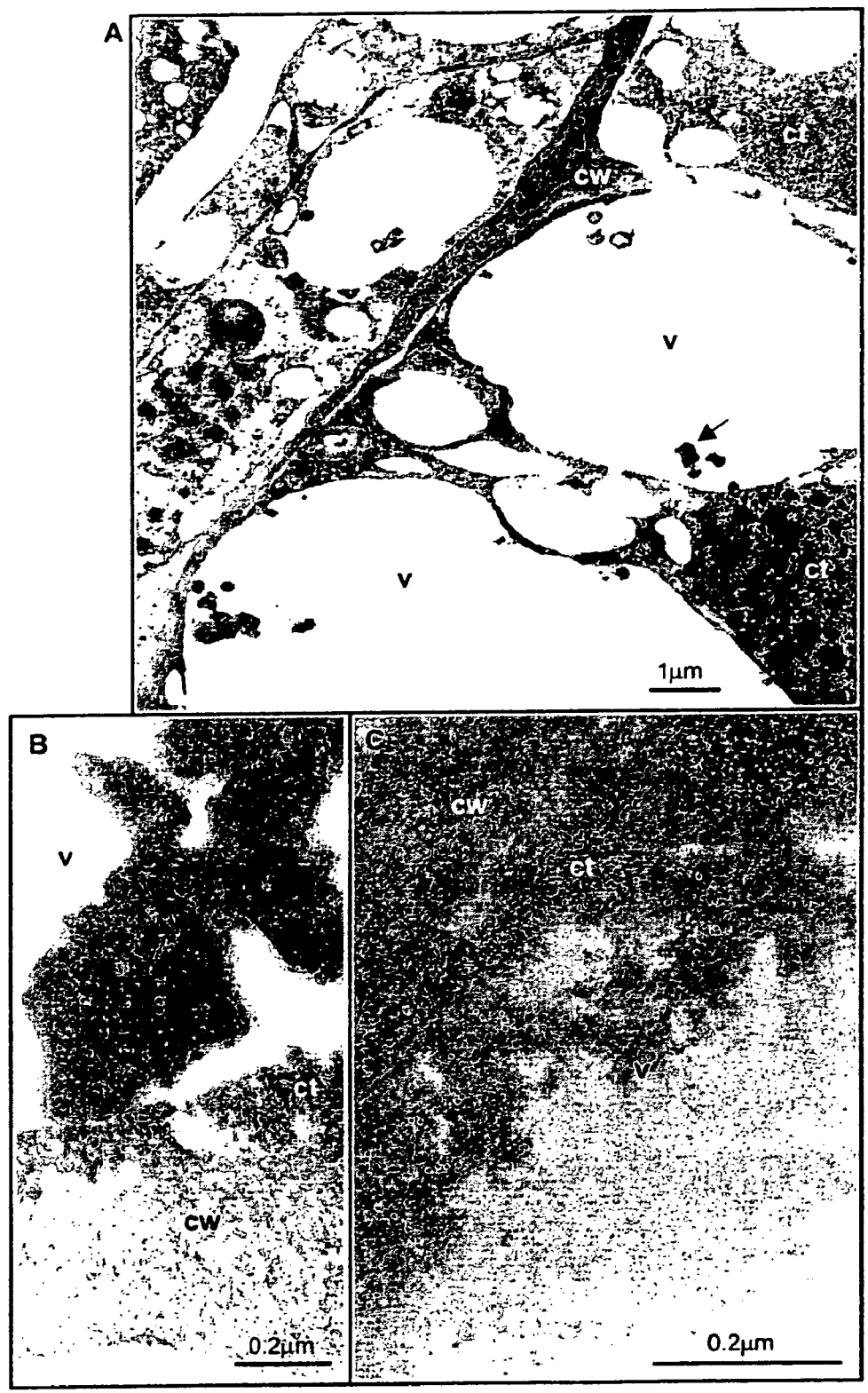
FIG. 7 is a series of electron micrographs showing the location of the *N. alata* defensin in anthers and ovaries from 10 mm flower buds. (A) Overview of the anther showing the cells of the connective tissue with electron dense deposits (arrowed) in the vacuole. (B) Immunogold localization of the defensin in the cells of the connective tissue of the anther. The antibody bound to the electron dense deposits in the vacuole (v) and did not bind to the cytoplasm (ct) or the cell wall (cw). (C) Immunogold localization of the defensin in the cortical cells of the ovary. The antibody bound specifically to electron dense deposits in the vacuole and no binding was observed in the cytoplasm or cell walls.

RP-HPLC was performed on a Beckman System Gold HPLC coupled to a Beckmann 166 detector. Analytical RP-HPLC was conducted on an Aquapore RP300 reverse-phase C8 column (4.6×100 mm, Brownlee) while preparative runs were performed using a Vydac C8 reverse-phase column (22×250 mm). The protein was eluted with a linear gradient of 0-100% buffer B (60% v/v acetonitrile in 0.089% v/v trifluoroacetic acid) at a flow-rate of 1 mL/min or 10 mL/min over 40 min, respectively. Results from the analytical column are shown in FIG. 6A. The identity of the major peak was confirmed by N-terminal sequencing and mass spectrometry, as described below.

(c) Electrospray Ionisation Mass Spectrometry

Prior to electrospray ionization mass spectrometry (ESI-MS), protein fractions from RP-HPLC were concentrated under vacuum in a freeze drier and reconstituted in milli-Q water. ESI-MS was carried out using 1-100 pmol protein in 2-4 µL of 50% v/v acetonitrile containing 0.1% w/v formic acid. Samples were infused at a flow rate of 0.2 µL/min into a Perkin-Elmer Sciex API-300 triple quadruple fitted with a micro-ionspray ion source. The mass scale was calibrated using singly-charged poly(propylene glycol) ions to a mass accuracy equivalent to ±1%. Mass spectra were recorded in the first quadruple (Q1) scan mode over the mass range m/z 200 to 3000 daltons per charge using a constant peak width (full width at half peak maximum) of 0.6 daltons per unit charge. Perkin-Elmer Sciex Bio-Multiview software was employed for signal averaging of 30-100 scans, manual mass determination and transformation of mass-to-charge ratio spectra to a true mass scale. Uncertainties were calculated at 95% confidence limits using small sample statistics and include calibration uncertainty.

Results indicated that the protein in Peak A in FIG. 6A, and the lower molecular weight species shown in FIG. 5B (~5 kDa), corresponded to the mature defensin domain encoded by the NaPdf1 cDNA clone (see FIG. 6B).

(d) Amino Acid Sequencing

Amino acid sequencing by Edman degradation was carried out on an Applied Biosystems 470A gas-phase peptide sequenator coupled to an Applied Biosystems 130A separation system for automatic on-line PTH amino acid analysis. The eight amino acids of N-terminal sequence obtained from the protein in Peak A matched the sequence predicted from the NaPdf1 cDNA clone (see FIG. 6B).

EXAMPLE 6

Immunogold Localization

Fixation and Immunogold Labelling for Electron Microscopy

Anthers and ovaries were removed from *N. alata* flowers at the immature bud stage (10 mm) and were fixed for 2 h at room temperature and then overnight at 4° C. in 4% (w/v) formaldehyde and 0.5% (w/v) glutaraldehyde in 60 mM PIPES/KOH, pH 7.2. After fixation, the tissues were washed in 60 mM PIPES/KOH, pH 7.2 and dehydrated for 3 h at room temperature in acidified dimethoxypropane (concentrated hydrochloric acid:dimethoxypropane, 1:2000 [v/v]). The dehydrated segments were embedded in LR Gold containing Benzil (London Resin Co. Ltd.) by polymerization under a Phillips TUV 15-W UV lamp at a distance of 10 cm for 12 h at 25° C. Immunogold labelling of ultrathin sections was performed as described in Anderson et al. (*Planta* 171: 438-442, 1987). The protein A purified anti-6H.NaproPdf1 antibodies were incubated with anther and ovary sections at a final concentration of 64 µg IgG/mL and 21 µg IgG/mL, respectively. Specificity of labeling was tested by replacing the primary antibody with antibodies purified from pre-immune serum at the same concentration. For visualization of ultrastructure, the sections were stained for 15 min in 3% (w/v) aqueous uranyl acetate and 2 min with Sato triple lead stain (Sato, *J. Electron Microsc.* 17: 158-159, 1968) before being viewed on a Joel 1200 electron microscope.

EXAMPLE 7

Sequences and Sequence Comparisons

The nucleotide and predicted amino acid sequences of *N. alata* defensin are set forth in FIG. 1. The gene that the cDNA clone represents is designated NaPdf1 (*N. alata* plant defensin 1). The DNA sequence shown is a composite sequence from an overlapping cDNA clone and a primer extension product as follows: 1-49, primer extension product clone; 50-541, cDNA clone NaPdf1. The protein predicted by this composite cDNA sequence is shown below the nucleotide sequence. The cDNA clone contains a single open reading frame of 318 nucleotides, encoding for 105 amino acids. The PCR amplified sequence in the original pBS-NaPdf1 clone (see Example 2) corresponds to nucleotides 1-318 in the NaPdf1 clone shown in FIG. 1.

In FIG. 9, the 105-amino acid sequence of NaPdf1 (SEQ ID NO:18) is shown aligned with the predicted amino acid sequences encoded by five other flower-derived cDNA clones. The sequences, in order, are as follows: flower specific thionin (FST), sourced from Gu et al. [1992; supra] (SEQ ID NO: 20), derived from tobacco flowers; TPP3, sourced from Milligan and Gasser [1995; supra] (SEQ ID NO: 21), derived from tomato pistil; NTS13, sourced from Li and Gray [1999; supra] (SEQ ID NO: 22), derived from tobacco styles; PPT, sourced from Karunanandaa et al. [1994; supra] (SEQ ID NO: 23), derived from petunia pistil, and ATPIIIa, sourced from Yu et al. [1999; supra], Direct Submission, Accession No. S30578 (SEQ ID NO: 24), derived from *Arabidopsis*.

The 47 amino acids constituting the mature central domain of the NaPdf1 protein (SEQ ID NO:8) were also aligned with the corresponding amino acid sequences of the mature domains of other members of the plant defensin family (SEQ ID NO:25 to SEQ ID NO:49). Alignment was carried out using the computerized algorithm of ClustalW. The results are set forth in FIG. 10. For details of the relevant references from which each sequence was obtained, and for their individual sequence identifiers, refer to the figure legend.

EXAMPLE 8

Fungal Growth Inhibition Assays

The 96-well microtitre plate assay of Broekaert et al. (*EMS Microbiology Letters* 69: 55-60, 1990) was used to test the effect of the purified NaPdf1 protein on the growth of *Botrytis cinerea* (isolated from rosemary, Brunswick, Victoria), *Fusarium oxysporum* (f. sp. *dianthi*, Race 2; isolated from carnation by Florigene Limited, Collingwood, Victoria) and *Fusarium oxysporum* (f. sp. *vasinfectum*, isolate VCG 01111 from cotton; provided by the Department of Primary Industries, Queensland). Fungal spores were isolated from sporulating cultures growing on half strength potato dextrose agar (PDA, Difco) or gamma-irradiated carnation leaves in water agar by the addition of sterile water and the use of a spreader. The suspension was filtered through two layers of autoclaved muslin and the spore concentration in the filtrate determined using a haemocytometer. The spores were used directly or after storage in sterile 20% v/v glycerol solution at −20° C.

Antifungal assays were performed in 96-well flat-bottomed microtitre plates (Greiner) under aseptic conditions. The spore concentration was adjusted to about $2 \times 10^4$ spores/mL in PDB and 80 μL of this suspension was added to each well to which 20 μL of filter sterilised (0.22 μm syringe filter, Millipore) test protein (10, 50 or 100 μg/mL) or water was added. The purity and concentration of each protein was confirmed before use by RP-HPLC analysis. Sterile water and ovalbumin (Sigma) were added to other wells as negative controls, and a mixture of the antifungal proteins α- and β-purothionin (Sigma) was used as a positive control. The plates were shaken on an orbital shaker for a few seconds to mix the spores and the test proteins. The plates were allowed to stand for 30 min to allow the spores to sediment before the optical density of the plates were determined using a Spectra Max Pro 250 microplate reader (Molecular Devices) at 595 nm absorbance. The plates were incubated in the dark at 22° C. and measurements were taken over the course of 100 h. An increase in absorbance relative to the initial reading was correlated with the growth of fungal hyphae and this was plotted against time. All assays were performed in quadruplicate.

Growth inhibition curves, set out in FIGS. 11 and 12A-12C, show the effect of purified NaPdf1 defensin protein against *B. cinerea* (FIG. 11), *F. oxysporum* (f. sp. *dianthi*, FIG. 12A) and *F. oxysporum* (f sp. *vasinfectum*, FIGS. 12B and 12C), respectively. The results clearly indicate the effectiveness of 20 μg/mL of NaPdf1 against all three fungal pathogens.

EXAMPLE 9

Production of Transgenic Tobacco Plants (a) Construction of the Binary Plasmid Primers FLOR1 and FLOR2, as shown below, were used to amplify the full DNA coding sequence of NaPdf1 by conventional PCR, in order to incorporate a 5' EcoRI and a 3' XbaI restriction enzyme site for subsequent cloning steps.

Primer FLOR1 (EcoRI-spacer-ATG-seq, 31 mer):

[SEQ ID NO:5]
5' GGAATTCTAAACAATGGCTCGCTCCTTGTGC 3'

Primer FLOR2 (XbaI-stop-seq, 29 mer):

5' GCTCTAGATCAGITATCCATTATCTCTTC 3' [SEQ ID NO:6]

The resultant PCR product was directly sub-cloned into a TA vector (pCR2.1-TOPO, Invitrogen) and the sequence was verified by nucleotide sequencing. The NaPdf1 DNA was excised from the TA vector with EcoRI and XbaI restriction enzymes, gel purified and subcloned into the pFB98/06 vector (obtained from Florigene Limited, Collingwood, Australia), previously treated with compatible restriction enzymes to create p35-PDF1. This construct (p35-PDF1) contains the defensin cDNA flanked by the 35S cauliflower mosaic virus promoter (CaMV35S) and terminator sequences. Construct p35-PDF1 was further digested with SphI restriction enzyme, to remove the promoter-gene-terminator cassette, and gel purified. The 3' overhangs produced by SphI were blunt ended with T4 DNA polymerase and gel purified. At this stage, the cassette was inserted into a binary vector, pGCP1988 (Florigene) or pBIN19 (Bevan et al. [1983; supra]), which had previously been treated with the blunt end cutter SmaI restriction enzyme. The resultant constructs were designated (i) pFL1 (contained in pCGP1988), which has a glean (surB) selectable marker gene under the control of the CaMV35S promoter/terminator, and (ii) pHEX3 (contained in pBIN19) which has a kanamycin (nptII) selectable marker gene under the control of the nos promoter/terminator. Constructs pFL1 and pHEX3 have the defensin gene cassette in the convergent and tandem orientation relative to their selectable marker genes, respectively. Schematics of constructs pFL1 and pHEX3 are shown in FIG. 13.

(b) Transformation of *Agrobacterium tumefaciens* LBA4404

Electro-competent *Agrobacterium tumefaciens* (LBA4404) were prepared and transformed with either pFL1 or pHEX3 by conventional electroporation in a Gene Pulser (registered trademark)/*E. coli* cuvettes with a 0.2 cm electrode gap (Bio-Rad) and exposed to 1.8 kV, a capacitance of 25 μFD and a resistance of 600 ohms in a Gene Pulser (Bio-Rad). The electroporated cells were combined with 1 mL SOC medium and incubated with shaking at 28° C. for 3 h before 150 μL was withdrawn and plated out on LB agar supplemented with 20 μg/mL rifampicin for pFL1 transformants or 20 μg/mL rifampicin and 50 μg/mL kanamycin for pHEX3 transformants. The plates were incubated overnight at 28° C.

Transformants were selected by preparing plasmid DNA from randomly chosen colonies, performing diagnostic restriction digests and analysing for inserts by agarose gel electrophoresis.

(c) *Agrobacterium*-Mediated Transformation of Tobacco

Seeds of *N. tabacum* cultivar Wisconscin 38 (W38) were surface sterilized in 1% v/v sodium hypochlorite for 60 min followed by several washes in sterile water. The sterilized seeds were sown onto MS medium (MS; 0.44% w/v Murashige and Skoog medium (ICN Biomedicals) [*Plant Physiology* 15: 73-97, 1962], 3% w/v sucrose and 0.8% w/v Bacto agar, pH 5.8) and incubated in a temperature control cabinet for 5 weeks. *A. tumefaciens* (LBA4404) transformed with either the pFL1 or pHEX3 constructs were grown for 2-3 days in 10 ml LB medium supplemented with the antibiotics rifampicin (20 µg/ml) or kanamycin (50 µg/ml) and rifampicin at 28° C., respectively. The cells were collected by centrifugation (5 min, 3,500×g), resuspended in 20 ml MS and incubated with freshly cut leaf disks (1 cm² squares) briefly. The disks were blotted onto sterile 3MM paper before being transferred onto SIM agar (0.44% w/v Murashige and Skoog medium (ICN Biomedicals) [1962; supra], 3% w/v sucrose, 1.0 mg/L BAP, 0.5 mg/L indole acetic acid (IAA) and 0.8% w/v Bacto agar, pH 5.8) and incubated for 3 days at 25° C. in light. Control leaf disks were treated similarly with MS alone. Following co-cultivation, calli were transferred onto selective media to induce shoot formation. pFL1 transformed calli were transferred to SIM agar supplemented with 1.5 mg/L glean and 250 mg/L cefotaxamine while the pHEX3 transformed calli were selected with 100 mg/L kanamycin and 250 mg/L cefotaxamine. The regenerated shoots were dissected from the calli, briefly dipped in IBA (1 mg/mL) solution, and transferred onto root-inducing medium (RIM; 0.44% w/v Murashige and Skoog medium [1962; supra], 3% w/v sucrose, 150 mg/L timentin and 0.8% w/v Bacto agar), supplemented with either 1.5 mg/L glean or 100 mg/L kanamycin for pFLI or pHEX3, respectively and incubated as described previously. When adequate root growth was established, plantlets were potted into soil and grown under standard glasshouse conditions.

(d) Detection of NaPdf1 in Transgenic Tobacco Leaves

Leaves ($4^{th}$ or $5^{th}$ position) were cut at the petiole from glasshouse grown plants. The tissue was frozen in liquid nitrogen and ground to a fine powder with a mortar and pestle. The tissue was added to extraction buffer: 50 mM Tris-HCl pH 8.0, 10 mM EDTA and 0.5 M NaCl (1 mL/g of fresh wet weight). The mixture was allowed to stand on ice for 15 min before clarification by centrifugation at 13,500×g for 15 min, 4° C. Protein concentrations were estimated by the method of Bradford (1976), reagents were from Bio-Rad and BSA was used as a standard. Total soluble leaf proteins (100 µg) were separated by SDS-PAGE using either 15% w/v or preformed 4-12% w/v polyacrylamide gradient gels (Novex) as described in Example 4(d), above. Following electrophoresis, proteins were either stained using coomassie blue or transferred to nitrocellulose for immunodetection of NaPdf1 as described in Example 4(e), above. Comparative results are shown in FIGS. 14A and B.

EXAMPLE 10

Insect Feeding Trials (a) Source of Insects

*Helicoverpa punctigera* larvae came from a colony collected in Victoria, Australia and maintained in culture at La Trobe University, Melbourne and *H. armigera* were obtained from a colonies maintained at La Trobe University, Melbourne or the Australian Cotton Research Institute, at the Entomology Department of the Commonwealth Scientific and Industrial Research Organisation in Narrabri, NSW.

(b) Bioassays with Transgenic Tobacco Leaves

Three experiments were conducted with clonal material from transgenic plant, pFL1/W19 (transformed with the pFL1 construct) and transgenic plant, pHEX3.4 (transformed with the pHEX3 construct). An untransformed W38 plant was used as negative control.

In experiments 1 and 2, 31 and 40 newly hatched *Helicoverpa punctigera* larvae were selected for each treatment, respectively. The larvae were reared in individual plastic cups with lids (Solo (registered trademark) plastic portion cups, 28 mL) containing 1.5% w/v Bacto agar and were fed leaf segments that were replaced either every 2-3 days or when more than 75% had been consumed. The amount of leaf material was increased as the larvae reached $5^{th}$ instar. Young leaves from non-flowering plants were used in all bioassays. To avoid a wounding response, the leaves were freshly excised from the petiole with a clean scalpel blade and were divided into sections (2×2 cm) by careful dissection between the major veins to minimize any wound response in the leaf sections. The larvae were kept in a controlled temperature room of 24±1° C., under light. The weights of the larvae were measured every 2-3 days until day 23 and the mean weight calculated. In experiment 3, 40 *H. armigera* larvae were used under the same conditions described for the *H. punctigera* bioassays. Results are shown in FIGS. 15A-15D.

(c) Bioassays with Artificial Diet

To confirm that the insecticidal activity was due to the defensin and not to upregulation of other endogenous defence molecules, a feeding trial using artificial cotton leaf diet containing purified defensin from floral buds was performed. The 6 kDa cysteine rich proteinase inhibitors (NaPI) from *N. alata* (Atkinson et al., *Plant Cell* 5: 203-213, 1993) were used as positive control and casein was used as a negative control. Feeding trials were conducted as described in Heath et al. (*J. Insect Physiology* 43: 833-842, 1997 except that the artificial diet was based on cotton leaves (Table 2). Thirty milligram of defensin was purified from floral buds of *N. alata* and used in artificial diets at two concentrations. *H. armigera* larvae fed on defensin at 0.3% (w/v) were 40% smaller than controls (FIG. 16) while larvae fed on NaPI at the same concentration were about 60% smaller than controls.

EXAMPLE 11

Production of Transgenic Cotton Plants (a) *Agrobacterium*-Mediated Transformation of Cotton Seeds of *Gossypium hirsutum* cultivar Coker 315 were surface sterilized in 2% v/v sodium hypochlorite for 60 min followed by several washes in sterile water. The sterilized seed were sown onto half-strength MS medium (MS; 0.22% w/v Murashige and Skoog salt mixture (Gibco BRL) [1962; supra], 0.2% Gelrite (Phyto Technology Laboratories), pH 5.8) and incubated at 30° C. in the dark for 7 days. *A. tumefaciens* (LBA4404) transformed with the pHEX3 construct was grown overnight in 25 ml LB medium supplemented with the antibiotic kanamycin (50 µg/mL) at 28° C. The absorbance at 550 nm was measured and the cells were diluted to $2 \times 10^8$ cells per ml in MS liquid media (0.43% w/v Murashige and Skoog salts [1962; supra], pH 5.8). Cotton hypocotyls were cut into 1.5-2 cm pieces and mixed briefly (0.5-3 min) in the diluted *Agrobacterium* culture. The explants were blotted dry on sterile 3MM paper and transferred to medium 1 (0.43% w/v Murashige and Skoog salt mixture (GibcoBRL) [1962; supra], 0.1% v/v Gamborg's B5 vitamin solution (Sigma), 0.1 g/L myo-inositol, 0.9 g/L $MgCl_2$, (hexahydrate), 1.9 g/L potassium nitrate, 0.2% w/v Gelrite, 3% w/v glucose, pH 5.8) overlayed with sterile filter paper and incubated for 3 days at 26° C. under lights Following co-cultivation, explants were transferred to medium 2 (medium 1 plus 0.1 mg/L kinetin, 0.1 mg/L 2,4-D, 500 mg/L carbenicillin, 35 mg/L kanamycin) and maintained at 30° C. under low light. After 4 weeks explants were transferred to medium 3 (medium 1 plus 500 mg/L carbenicillin, 35 mg/L kanamycin) and maintained at 30° C. under low light. Explants and callus were sub-cultured every 4 weeks on medium 3 and maintained at 30° C. under low light. Embryos were excised from the tissue and germinated in medium 4 (1.2 mM $CaCl_2 2H_2O$, 5.0 mM $KNO_3$, 2.0 mM $MgSO_4 7H_2O$, 3.0 mM $NH_4NO_3$, 0.2 mM $KH_2PO_4$, 4 μM nicotinic acid, 4 μM pyridoxine HCl, 4 μM thiamine HCl, 30 μM $H_3BO_3$, 30 μM $MnSO_4H_2O$, 9 μM $ZnSO_4 7H_2O$, 1.5 μM KI, 0.9 μM $Na_2MoO_4 2H_2O$, 0.03 μM $CuSO_4 5H_2O$, 0.03 μM $COCl_2 6H_2O$, 0.5% w/v glucose, 0.3% w/v Gelrite, pH 5.5) and maintained at 30° C. under high light.

Germinated embryos were then transferred to Magenta boxes containing medium 5 (1.2 mM $CaCl_2 2H_2O$, 40.0 mM $KNO_3$, 2.0 mM $MgSO_4 7H_2O$, 15 mM $NH_4Cl$, 0.2 mM $KH_2PO_4$, 4 μM nicotinic acid, 4 μl M pyridoxine HCl, 4 μM thiamine HCl, 30 μM $H_3BO_3$, 30 μM $MnSO_4H_2O$, 9 μM $ZnSO_4 7H_2O$, 1.5 μM KI, 0.9 μM $Na_2MoO_4 2H_2O$, 0.03 μM $CuSO_4 5H_2O$, 0.03 μM $COCl_2 6H_2O$, 2.0% w/v sucrose, 0.2% w/v Gelrite, pH 5.5) and maintained at 30° C. under high light. Once a plant has formed a good root system and produced several new leaves it was transferred to soil in pots and acclimatised in a growth cabinet at 28° C. and then grown in a glasshouse at (27-29° C. day, 20-24° C. night).

(b) Detection of NaPdf1 in Transgenic Cotton

Leaves (first position, 3-4 cm in diameter) were excised from plants grown either in the growth cabinet or in the glasshouse. The tissue (100 mg) was frozen in liquid nitrogen and ground to a fine powder with a mortar and pestle. The powder was added to 2× sample buffer (300 μl, Novex NuPAGE LDS sample buffer, 10% v/v β-mercaptoethanol), vortexed for 30 sec, boiled for 5 min and then centrifuged at 14,000 rpm for 10 min and the supernatant retained. Total soluble leaf extracts were separated by SDS-PAGE on preformed 4-12% w/v polyacrylamide gradient gels (Novex, NuPAGE bis-tris, MES buffer) for 35 min at 200V in a Novex X Cell II mini-cell electrophoresis apparatus. Prestained molecular weight markers (Novex SeeBlue) were included as a standard. Proteins were transferred to nitrocellulose membrane (Micron Separations Inc. 0.22 micron pore size) for 60 min at 30V using the Novex X Cell II mini-cell electrophoresis apparatus in NuPAGE transfer buffer with 10% v/v methanol. After transfer, membranes were incubated for 1 min in isopropanol, followed by a 5 min wash in TBS.

The membrane was blocked for 1 h in 3% w/v BSA at RT followed by incubation with primary antibody overnight at RT (1:2500 dilution in TBS). The membrane was washed 5×10 min in TBST before incubation with goat anti-rabbit IgG conjugated to horseradish peroxidase for 60 min at RT (Pierce, 1:100,000 dilution in TBS). Five further 10 min TBST washes were performed before the membrane was incubated with the SuperSignal West Pico Chemiluminescent substrate (Pierce) according to the Manufacturer's instructions. Membranes were exposed to ECL Hyperfilm (Amersham Pharmacia Biotech). Results are shown in FIG. 14C.

EXAMPLE 12

Insect Feeding Trial with Transgenic Cotton

One experiment was conducted with two independently transformed T2 generation transgenic cotton lines. The plants were produced by selfing the primary transgenic lines CT35.9.4 and CT35.125.1 (both transformed with the pHEX3 construct) and consisted of a mixture of homozygous and hemizygous plants. Parent untransformed Coker 315 plants were used as a negative control.

Twenty newly hatched *H. armigera* larvae were selected. The larvae were reared in individual plastic cups with lids (Solo (registered trademark) plastic portion cups, 28 ml) containing 1.5% Bacto agar and were fed leaf segments that were replaced either every 2-3 days or when more than 75% had been consumed. Young leaves from non-flowering plants were used in the bioassay. The larvae were kept in a controlled temperature room at 25±1□C, under light. The number of dead larvae was recorded on days 4, 6 and 8. The weight of each surviving larvae was measured at day 8 and the mean weight calculated. Results are shown in FIG. 17.

EXAMPLE 13

Production of Insect-Resistant Plants (a) Molecular Cloning of Genes from a Range of Species Amino acid sequences of any one of the sequences set forth in FIG. 10 (SEQ ID NO:25 to SEQ ID NO:49) are used to design suitable oligonucleotide primers for use in screening cDNA or genomic DNA libraries, as appropriate. Using, for example PCR, corresponding full nucleotide coding sequences are cloned as, for example, described in Examples 4(a) and 9(a), above. Expression cassettes are then inserted into desired vectors such as, for example, pBIN19 or pCGP1988, use of which is described in Example 9(a).

(b) Transformation and Regeneration of Insect-Resistant Plants

Using standard techniques known and available to those skilled in the art, selected plant material of target plant species is transformed with one or more vectors comprising the expression cassettes carrying the anti-insect sequences from the corresponding species. Suitable transformation methods include, but are not limited to, the *Agrobacterium*-mediated transformation protocol set forth in Example 9(b), 9(c) and 9(d), modified as necessary for particular plant species. Other means of transformation of particular plant species are well known and include, for example, biolistic transformation procedures.

Following regeneration, plants are assayed for resistance to attack by common plant pests including insects.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

SEQUENCE LISTING

<160> NUMBER OF SEQ ID NOS: 62

<210> SEQ ID NO 1
<211> LENGTH: 28
<212> TYPE: DNA
<213> ORGANISM: Artificial sequence
<220> FEATURE:
<223> OTHER INFORMATION: Description of Artificial sequence: primer

<400> SEQUENCE: 1
ggaattccat atggctcgct ccttgtgc                               28

<210> SEQ ID NO 2
<211> LENGTH: 29
<212> TYPE: DNA
<213> ORGANISM: Artificial sequence
<220> FEATURE:
<223> OTHER INFORMATION: Description of Artificial sequence: primer

<400> SEQUENCE: 2
gcggatcctc agttatccat tatctcttc                              29

<210> SEQ ID NO 3
<211> LENGTH: 24
<212> TYPE: DNA
<213> ORGANISM: Artificial sequence
<220> FEATURE:
<223> OTHER INFORMATION: Description of Artificial sequence: primer

<400> SEQUENCE: 3
ccggatccag agaatgcaaa acag                                   24

<210> SEQ ID NO 4
<211> LENGTH: 26
<212> TYPE: DNA
<213> ORGANISM: Artificial sequence
<220> FEATURE:
<223> OTHER INFORMATION: Description of Artificial sequence: primer

<400> SEQUENCE: 4
gggagctctt agttatccat tatctc                                 26

<210> SEQ ID NO 5
<211> LENGTH: 31
<212> TYPE: DNA
<213> ORGANISM: Artificial sequence
<220> FEATURE:
<223> OTHER INFORMATION: Description of Artificial sequence: primer

<400> SEQUENCE: 5
ggaattctaa acaatggctc gctccttgtg c                           31

<210> SEQ ID NO 6
<211> LENGTH: 29
<212> TYPE: DNA
<213> ORGANISM: Artificial sequence
<220> FEATURE:
<223> OTHER INFORMATION: Description of Artificial sequence: primer

<400> SEQUENCE: 6
gctctagatc agttatccat tatctcttc                              29

<210> SEQ ID NO 7
<211> LENGTH: 141

```
<212> TYPE: DNA
<213> ORGANISM: Nicotiana alata
<220> FEATURE:
<221> NAME/KEY: CDS
<222> LOCATION: (1)..(141)

<400> SEQUENCE: 7 aga gaa tgc aaa aca gaa agc aac aca ttt cct gga ata tgc att acc      48
Arg Glu Cys Lys Thr Glu Ser Asn Thr Phe Pro Gly Ile Cys Ile Thr
1               5                   10                  15 aaa cca cca tgc aga aaa gct tgt atc agt gag aaa ttt act gat ggt      96
Lys Pro Pro Cys Arg Lys Ala Cys Ile Ser Glu Lys Phe Thr Asp Gly
                20                  25                  30 cat tgt agc aaa atc ctc aga agg tgc cta tgt act aag cca tgt         141
His Cys Ser Lys Ile Leu Arg Arg Cys Leu Cys Thr Lys Pro Cys
            35                  40                  45

<210> SEQ ID NO 8
<211> LENGTH: 47
<212> TYPE: PRT
<213> ORGANISM: Nicotiana alata

<400> SEQUENCE: 8

Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
                20                  25                  30

His Cys Ser Lys Ile Leu Arg Arg Cys Leu Cys Thr Lys Pro Cys
            35                  40                  45

<210> SEQ ID NO 9
<211> LENGTH: 75
<212> TYPE: DNA
<213> ORGANISM: Nicotiana alata
<220> FEATURE:
<221> NAME/KEY: CDS
<222> LOCATION: (1)..(75)

<400> SEQUENCE: 9 atg gct cgc tcc ttg tgc ttc atg gca ttt gct atc ttg gca agg atg      48
Met Ala Arg Ser Leu Cys Phe Met Ala Phe Ala Ile Leu Ala Arg Met
1               5                   10                  15 ctc ttt gtt gcc tat gag gtg caa gct                                  75
Leu Phe Val Ala Tyr Glu Val Gln Ala
                20                  25

<210> SEQ ID NO 10
<211> LENGTH: 25
<212> TYPE: PRT
<213> ORGANISM: Nicotiana alata

<400> SEQUENCE: 10

Met Ala Arg Ser Leu Cys Phe Met Ala Phe Ala Ile Leu Ala Arg Met
1               5                   10                  15

Leu Phe Val Ala Tyr Glu Val Gln Ala
                20                  25

<210> SEQ ID NO 11
<211> LENGTH: 99
<212> TYPE: DNA
<213> ORGANISM: Nicotiana alata
<220> FEATURE:
<221> NAME/KEY: CDS
<222> LOCATION: (1)..(99)
```

```
<400> SEQUENCE: 11 gtg ttt gat gag aag atg act aaa aca gga gct gaa att ttg gct gag        48
Val Phe Asp Glu Lys Met Thr Lys Thr Gly Ala Glu Ile Leu Ala Glu
1               5                   10                  15 gaa gca aaa act ttg gct gca gct ttg ctt gaa gaa gag ata atg gat        96
Glu Ala Lys Thr Leu Ala Ala Ala Leu Leu Glu Glu Glu Ile Met Asp
            20                  25                  30 aac                                                                    99
Asn

<210> SEQ ID NO 12
<211> LENGTH: 33
<212> TYPE: PRT
<213> ORGANISM: Nicotiana alata

<400> SEQUENCE: 12

Val Phe Asp Glu Lys Met Thr Lys Thr Gly Ala Glu Ile Leu Ala Glu
1               5                   10                  15

Glu Ala Lys Thr Leu Ala Ala Ala Leu Leu Glu Glu Glu Ile Met Asp
            20                  25                  30

Asn

<210> SEQ ID NO 13
<211> LENGTH: 216
<212> TYPE: DNA
<213> ORGANISM: Nicotiana alata
<220> FEATURE:
<221> NAME/KEY: CDS
<222> LOCATION: (1)..(216)

<400> SEQUENCE: 13 atg gct cgc tcc ttg tgc ttc atg gca ttt gct atc ttg gca agg atg        48
Met Ala Arg Ser Leu Cys Phe Met Ala Phe Ala Ile Leu Ala Arg Met
1               5                   10                  15 ctc ttt gtt gcc tat gag gtg caa gct aga gaa tgc aaa aca gaa agc        96
Leu Phe Val Ala Tyr Glu Val Gln Ala Arg Glu Cys Lys Thr Glu Ser
            20                  25                  30 aac aca ttt cct gga ata tgc att acc aaa cca cca tgc aga aaa gct       144
Asn Thr Phe Pro Gly Ile Cys Ile Thr Lys Pro Pro Cys Arg Lys Ala
        35                  40                  45 tgt atc agt gag aaa ttt act gat ggt cat tgt agc aaa atc ctc aga       192
Cys Ile Ser Glu Lys Phe Thr Asp Gly His Cys Ser Lys Ile Leu Arg
    50                  55                  60 agg tgc cta tgt act aag cca tgt                                       216
Arg Cys Leu Cys Thr Lys Pro Cys
65                  70

<210> SEQ ID NO 14
<211> LENGTH: 72
<212> TYPE: PRT
<213> ORGANISM: Nicotiana alata

<400> SEQUENCE: 14

Met Ala Arg Ser Leu Cys Phe Met Ala Phe Ala Ile Leu Ala Arg Met
1               5                   10                  15

Leu Phe Val Ala Tyr Glu Val Gln Ala Arg Glu Cys Lys Thr Glu Ser
            20                  25                  30

Asn Thr Phe Pro Gly Ile Cys Ile Thr Lys Pro Pro Cys Arg Lys Ala
        35                  40                  45

Cys Ile Ser Glu Lys Phe Thr Asp Gly His Cys Ser Lys Ile Leu Arg
    50                  55                  60
```

<210> SEQ ID NO 15
<211> LENGTH: 240
<212> TYPE: DNA
<213> ORGANISM: Nicotiana alata
<220> FEATURE:
<221> NAME/KEY: CDS
<222> LOCATION: (1)..(240)

<400> SEQUENCE: 15

```
aga gaa tgc aaa aca gaa agc aac aca ttt cct gga ata tgc att acc        48
Arg Glu Cys Lys Thr Glu Ser Asn Thr Phe Pro Gly Ile Cys Ile Thr
1               5                   10                  15 aaa cca cca tgc aga aaa gct tgt atc agt gag aaa ttt act gat ggt        96
Lys Pro Pro Cys Arg Lys Ala Cys Ile Ser Glu Lys Phe Thr Asp Gly
                20                  25                  30 cat tgt agc aaa atc ctc aga agg tgc cta tgt act aag cca tgt gtg      144
His Cys Ser Lys Ile Leu Arg Arg Cys Leu Cys Thr Lys Pro Cys Val
            35                  40                  45 ttt gat gag aag atg act aaa aca gga gct gaa att ttg gct gag gaa      192
Phe Asp Glu Lys Met Thr Lys Thr Gly Ala Glu Ile Leu Ala Glu Glu
        50                  55                  60 gca aaa act ttg gct gca gct ttg ctt gaa gaa gag ata atg gat aac      240
Ala Lys Thr Leu Ala Ala Ala Leu Leu Glu Glu Glu Ile Met Asp Asn
65                  70                  75                  80
```

<210> SEQ ID NO 16
<211> LENGTH: 80
<212> TYPE: PRT
<213> ORGANISM: Nicotiana alata

<400> SEQUENCE: 16

```
Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
                20                  25                  30

His Cys Ser Lys Ile Leu Arg Arg Cys Leu Cys Thr Lys Pro Cys Val
            35                  40                  45

Phe Asp Glu Lys Met Thr Lys Thr Gly Ala Glu Ile Leu Ala Glu Glu
        50                  55                  60

Ala Lys Thr Leu Ala Ala Ala Leu Leu Glu Glu Glu Ile Met Asp Asn
65                  70                  75                  80
```

<210> SEQ ID NO 17
<211> LENGTH: 541
<212> TYPE: DNA
<213> ORGANISM: Nicotiana alata
<220> FEATURE:
<221> NAME/KEY: CDS
<222> LOCATION: (1)..(318)

<400> SEQUENCE: 17

```
atg gct cgc tcc ttg tgc ttc atg gca ttt gct atc ttg gca agg atg        48
Met Ala Arg Ser Leu Cys Phe Met Ala Phe Ala Ile Leu Ala Arg Met
1               5                   10                  15 ctc ttt gtt gcc tat gag gtg caa gct aga gaa tgc aaa aca gaa agc        96
Leu Phe Val Ala Tyr Glu Val Gln Ala Arg Glu Cys Lys Thr Glu Ser
                20                  25                  30 aac aca ttt cct gga ata tgc att acc aaa cca cca tgc aga aaa gct      144
Asn Thr Phe Pro Gly Ile Cys Ile Thr Lys Pro Pro Cys Arg Lys Ala
```

```
                      35                  40                  45
tgt atc agt gag aaa ttt act gat ggt cat tgt agc aaa atc ctc aga      192
Cys Ile Ser Glu Lys Phe Thr Asp Gly His Cys Ser Lys Ile Leu Arg
        50                  55                  60 agg tgc cta tgt act aag cca tgt gtg ttt gat gag aag atg act aaa      240
Arg Cys Leu Cys Thr Lys Pro Cys Val Phe Asp Glu Lys Met Thr Lys
 65                  70                  75                  80 aca gga gct gaa att ttg gct gag gaa gca aaa act ttg gct gca gct      288
Thr Gly Ala Glu Ile Leu Ala Glu Glu Ala Lys Thr Leu Ala Ala Ala
                    85                  90                  95 ttg ctt gaa gaa gag ata atg gat aac taa ttagagatta gaagaaatta        338
Leu Leu Glu Glu Glu Ile Met Asp Asn
                100                 105 aggatgcagt atcacacata ataaagtttc tacctttctt aaaagtgtag ctaatgttgt    398
gttttaattg gcttttagta gccttttatt acactttaaa taagtgtggc acttcaatcc    458
tttgtgcaat cttgcactaa gtttatttgt gtacttttaa tgaaaatgac cttctatggt    518
ctttggttaa aaaaaaaaaa aaa                                             541

<210> SEQ ID NO 18
<211> LENGTH: 105
<212> TYPE: PRT
<213> ORGANISM: Nicotiana alata

<400> SEQUENCE: 18

Met Ala Arg Ser Leu Cys Phe Met Ala Phe Ala Ile Leu Ala Arg Met
 1               5                  10                  15

Leu Phe Val Ala Tyr Glu Val Gln Ala Arg Glu Cys Lys Thr Glu Ser
                20                  25                  30

Asn Thr Phe Pro Gly Ile Cys Ile Thr Lys Pro Cys Arg Lys Ala
            35                  40                  45

Cys Ile Ser Glu Lys Phe Thr Asp Gly His Cys Ser Lys Ile Leu Arg
        50                  55                  60

Arg Cys Leu Cys Thr Lys Pro Cys Val Phe Asp Glu Lys Met Thr Lys
 65                  70                  75                  80

Thr Gly Ala Glu Ile Leu Ala Glu Glu Ala Lys Thr Leu Ala Ala Ala
                    85                  90                  95

Leu Leu Glu Glu Glu Ile Met Asp Asn
                100                 105

<210> SEQ ID NO 19
<211> LENGTH: 223
<212> TYPE: DNA
<213> ORGANISM: Nicotiana alata

<400> SEQUENCE: 19
ttagagatta gaagaaatta aggatgcagt atcacacata ataaagtttc tacctttctt     60
aaaagtgtag ctaatgttgt gttttaattg gcttttagta gccttttatt acactttaaa    120
taagtgtggc acttcaatcc tttgtgcaat cttgcactaa gtttatttgt gtacttttaa    180
tgaaaatgac cttctatggt ctttggttaa aaaaaaaaaa aaa                      223

<210> SEQ ID NO 20
<211> LENGTH: 105
<212> TYPE: PRT
<213> ORGANISM: peptide

<400> SEQUENCE: 20
```

Met Ala Arg Ser Leu Cys Phe Met Ala Phe Ala Ile Leu Ala Met Met
1               5                   10                  15

Leu Phe Val Ala Tyr Glu Val Gln Ala Arg Glu Cys Lys Thr Glu Ser
                20                  25                  30

Asn Thr Phe Pro Gly Ile Cys Ile Thr Lys Pro Pro Cys Arg Lys Ala
            35                  40                  45

Cys Ile Ser Glu Lys Phe Thr Asp Gly His Cys Ser Lys Leu Leu Arg
    50                  55                  60

Arg Cys Leu Cys Thr Lys Pro Cys Val Phe Asp Glu Lys Met Ile Lys
65              70                  75                  80

Thr Gly Ala Glu Thr Leu Val Glu Glu Ala Lys Thr Leu Ala Ala Ala
                85                  90                  95

Leu Leu Glu Glu Glu Ile Met Asp Asn
            100                 105

<210> SEQ ID NO 21
<211> LENGTH: 105
<212> TYPE: PRT
<213> ORGANISM: peptide

<400> SEQUENCE: 21

Met Ala Arg Ser Ile Phe Phe Met Ala Phe Leu Val Leu Ala Met Met
1               5                   10                  15

Leu Phe Val Thr Tyr Glu Val Glu Ala Gln Gln Ile Cys Lys Ala Pro
                20                  25                  30

Ser Gln Thr Phe Pro Gly Leu Cys Phe Met Asp Ser Ser Cys Arg Lys
            35                  40                  45

Tyr Cys Ile Lys Glu Lys Phe Thr Gly Gly His Cys Ser Lys Leu Gln
    50                  55                  60

Arg Lys Cys Leu Cys Thr Lys Pro Cys Val Phe Asp Lys Ile Ser Ser
65              70                  75                  80

Glu Val Lys Ala Thr Leu Gly Glu Glu Ala Lys Thr Leu Ser Glu Val
                85                  90                  95

Val Leu Glu Glu Glu Ile Met Met Glu
            100                 105

<210> SEQ ID NO 22
<211> LENGTH: 78
<212> TYPE: PRT
<213> ORGANISM: peptide

<400> SEQUENCE: 22

Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Arg
                20                  25                  30

Thr Cys Glu Ser Gln Ser His Arg Phe Lys Gly Pro Cys Ser Arg Asp
            35                  40                  45

Ser Asn Cys Ala Thr Val Cys Leu Thr Glu Gly Phe Ser Gly Gly Arg
    50                  55                  60

Cys Pro Trp Ile Pro Pro Arg Cys Phe Cys Thr Ser Pro Cys
65              70                  75

<210> SEQ ID NO 23
<211> LENGTH: 78
<212> TYPE: PRT
<213> ORGANISM: peptide

<400> SEQUENCE: 23

Met Gly Arg Ser Ile Arg Leu Phe Ala Thr Phe Phe Leu Ile Ala Met
1               5                   10                  15

Leu Phe Leu Ser Thr Glu Met Gly Pro Met Thr Ser Ala Glu Ala Arg
            20                  25                  30

Thr Cys Glu Ser Gln Ser His Arg Phe His Gly Thr Cys Val Arg Glu
        35                  40                  45

Ser Asn Cys Ala Ser Val Cys Gln Thr Glu Gly Phe Ile Gly Gly Asn
    50                  55                  60

Cys Arg Ala Phe Arg Arg Arg Cys Phe Cys Thr Arg Asn Cys
65                  70                  75

<210> SEQ ID NO 24
<211> LENGTH: 77
<212> TYPE: PRT
<213> ORGANISM: peptide

<400> SEQUENCE: 24

Met Lys Leu Ser Met Arg Leu Ile Ser Ala Val Leu Ile Met Phe Met
1               5                   10                  15

Ile Phe Val Ala Thr Gly Met Gly Pro Val Thr Val Glu Ala Arg Thr
            20                  25                  30

Cys Glu Ser Gln Ser His Arg Phe Lys Gly Thr Cys Val Ser Ala Ser
        35                  40                  45

Asn Cys Ala Asn Val Cys His Asn Glu Gly Phe Val Gly Gly Asn Cys
    50                  55                  60

Arg Gly Phe Arg Arg Arg Cys Phe Cys Thr Arg His Cys
65                  70                  75

<210> SEQ ID NO 25
<211> LENGTH: 47
<212> TYPE: PRT
<213> ORGANISM: peptide

<400> SEQUENCE: 25

Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Leu Leu Arg Arg Cys Leu Cys Thr Lys Pro Cys
        35                  40                  45

<210> SEQ ID NO 26
<211> LENGTH: 47
<212> TYPE: PRT
<213> ORGANISM: peptide

<400> SEQUENCE: 26

Gln Ile Cys Lys Ala Pro Ser Gln Thr Phe Pro Gly Leu Cys Phe Met
1               5                   10                  15

Asp Ser Ser Cys Arg Lys Tyr Cys Ile Lys Glu Lys Phe Thr Gly Gly
            20                  25                  30

His Cys Ser Lys Leu Gln Arg Lys Cys Leu Cys Thr Lys Pro Cys
        35                  40                  45

<210> SEQ ID NO 27
<211> LENGTH: 47
<212> TYPE: PRT
<213> ORGANISM: peptide

<400> SEQUENCE: 27

Arg His Cys Glu Ser Leu Ser His Arg Phe Lys Gly Pro Cys Thr Arg
1               5                   10                  15

Asp Ser Asn Cys Ala Ser Val Cys Glu Thr Glu Arg Phe Ser Gly Gly
                20                  25                  30

Asn Cys His Gly Phe Arg Arg Arg Cys Phe Cys Thr Lys Pro Cys
            35                  40                  45

<210> SEQ ID NO 28
<211> LENGTH: 47
<212> TYPE: PRT
<213> ORGANISM: peptide

<400> SEQUENCE: 28

Arg Val Cys Glu Ser Gln Ser His Gly Phe His Gly Leu Cys Asn Arg
1               5                   10                  15

Asp His Asn Cys Ala Leu Val Cys Arg Asn Glu Gly Phe Ser Gly Gly
                20                  25                  30

Arg Cys Lys Gly Phe Arg Arg Arg Cys Phe Cys Thr Arg Ile Cys
            35                  40                  45

<210> SEQ ID NO 29
<211> LENGTH: 47
<212> TYPE: PRT
<213> ORGANISM: peptide

<400> SEQUENCE: 29

Arg Thr Cys Glu Ser Gln Ser His Arg Phe His Gly Thr Cys Val Arg
1               5                   10                  15

Glu Ser Asn Cys Ala Ser Val Cys Gln Thr Glu Gly Phe Ile Gly Gly
                20                  25                  30

Asn Cys Arg Ala Phe Arg Arg Arg Cys Phe Cys Thr Arg Asn Cys
            35                  40                  45

<210> SEQ ID NO 30
<211> LENGTH: 47
<212> TYPE: PRT
<213> ORGANISM: peptide

<400> SEQUENCE: 30

Arg Ile Cys Arg Arg Arg Ser Ala Gly Phe Lys Gly Pro Cys Val Ser
1               5                   10                  15

Asn Lys Asn Cys Ala Gln Val Cys Met Gln Glu Trp Gly Glu Gly Gly
                20                  25                  30

Asn Cys Asp Gly Pro Leu Arg Arg Cys Lys Cys Met Arg Arg Cys
            35                  40                  45

<210> SEQ ID NO 31
<211> LENGTH: 51
<212> TYPE: PRT
<213> ORGANISM: peptide

<400> SEQUENCE: 31

Gln Lys Leu Cys Gln Arg Pro Ser Gly Thr Trp Ser Gly Val Cys Gly
1               5                   10                  15

Asn Asn Asn Ala Cys Arg Asn Gln Cys Ile Asn Leu Glu Lys Ala Arg
                20                  25                  30

His Gly Ser Cys Asn Tyr Val Phe Pro Ala His Lys Cys Ile Cys Tyr
            35                  40                  45

```
Phe Pro Cys
    50

<210> SEQ ID NO 32
<211> LENGTH: 20
<212> TYPE: PRT
<213> ORGANISM: peptide

<400> SEQUENCE: 32

Arg Asn Cys Glu Ser Leu Ser His Arg Phe Lys Gly Pro Cys Thr Arg
1               5                   10                  15

Asp Ser Asn Cys
            20

<210> SEQ ID NO 33
<211> LENGTH: 51
<212> TYPE: PRT
<213> ORGANISM: peptide

<400> SEQUENCE: 33

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Asn Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
    50

<210> SEQ ID NO 34
<211> LENGTH: 51
<212> TYPE: PRT
<213> ORGANISM: peptide

<400> SEQUENCE: 34

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
    50

<210> SEQ ID NO 35
<211> LENGTH: 51
<212> TYPE: PRT
<213> ORGANISM: peptide

<400> SEQUENCE: 35

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Asn Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
    50
```

<210> SEQ ID NO 36
<211> LENGTH: 52
<212> TYPE: PRT
<213> ORGANISM: peptide

<400> SEQUENCE: 36

Gln Lys Leu Cys Ala Arg Pro Ser Gly Thr Trp Ser Gly Asn Cys
1               5                   10                  15

Arg Asn Asn Ala Cys Arg Asn Phe Cys Ile Lys Leu Glu Lys Ser
            20                  25                  30

Arg His Gly Ser Cys Asn Ile Pro Phe Pro Ser Asn Lys Cys Ile Cys
        35                  40                  45

Tyr Phe Pro Cys
    50

<210> SEQ ID NO 37
<211> LENGTH: 47
<212> TYPE: PRT
<213> ORGANISM: peptide

<400> SEQUENCE: 37

Lys Ile Cys Arg Arg Ser Ala Gly Phe Lys Gly Pro Cys Met Ser
1               5                   10                  15

Asn Lys Asn Cys Ala Gln Val Cys Gln Gln Glu Gly Trp Gly Gly Gly
            20                  25                  30

Asn Cys Asp Gly Pro Phe Arg Arg Cys Lys Cys Ile Arg Gln Cys
        35                  40                  45

<210> SEQ ID NO 38
<211> LENGTH: 47
<212> TYPE: PRT
<213> ORGANISM: peptide

<400> SEQUENCE: 38

Lys Val Cys Arg Gln Arg Ser Ala Gly Phe Lys Gly Pro Cys Val Ser
1               5                   10                  15

Asp Lys Asn Cys Ala Gln Val Cys Leu Gln Glu Gly Trp Gly Gly Gly
            20                  25                  30

Asn Cys Asp Gly Pro Phe Arg Arg Cys Lys Cys Ile Arg Gln Cys
        35                  40                  45

<210> SEQ ID NO 39
<211> LENGTH: 47
<212> TYPE: PRT
<213> ORGANISM: peptide

<400> SEQUENCE: 39

Lys Thr Cys Glu Asn Leu Val Asp Thr Tyr Arg Gly Pro Cys Phe Thr
1               5                   10                  15

Thr Gly Ser Cys Asp Asp His Cys Lys Asn Lys Glu His Leu Leu Ser
            20                  25                  30

Gly Arg Cys Arg Asp Asp Val Arg Cys Trp Cys Thr Arg Asn Cys
        35                  40                  45

<210> SEQ ID NO 40
<211> LENGTH: 48
<212> TYPE: PRT
<213> ORGANISM: peptide

<400> SEQUENCE: 40

Arg Val Cys Met Gly Lys Ser Ala Gly Phe Lys Gly Leu Cys Met Arg

```
                    1               5                  10                 15
Asp Gln Asn Cys Ala Gln Val Cys Leu Gln Glu Gly Trp Gly Gly Gly
                    20                 25                 30

Asn Cys Asp Gly Val Met Arg Gln Cys Lys Cys Ile Arg Gln Cys Trp
                    35                 40                 45

<210> SEQ ID NO 41
<211> LENGTH: 48
<212> TYPE: PRT
<213> ORGANISM: peptide

<400> SEQUENCE: 41

Arg Val Cys Arg Arg Ser Ala Gly Phe Lys Gly Leu Cys Met Ser
1               5                  10                 15

Asp His Asn Cys Ala Gln Val Cys Leu Gln Glu Gly Trp Gly Gly Gly
                    20                 25                 30

Asn Cys Asp Gly Val Ile Arg Gln Cys Lys Cys Ile Arg Gln Cys Trp
                    35                 40                 45

<210> SEQ ID NO 42
<211> LENGTH: 20
<212> TYPE: PRT
<213> ORGANISM: peptide

<400> SEQUENCE: 42

Glu Val Cys Glu Lys Ala Ser Lys Thr Trp Ser Gly Asn Cys Gly Asn
1               5                  10                 15

Thr Gly His Cys
            20

<210> SEQ ID NO 43
<211> LENGTH: 47
<212> TYPE: PRT
<213> ORGANISM: peptide

<400> SEQUENCE: 43

Arg Val Cys Met Lys Gly Ser Gln His His Ser Phe Pro Cys Ile Ser
1               5                  10                 15

Asp Arg Leu Cys Ser Asn Glu Cys Val Lys Glu Glu Gly Gly Trp Thr
                    20                 25                 30

Ala Gly Tyr Cys His Leu Arg Tyr Cys Arg Cys Gln Lys Ala Cys
                    35                 40                 45

<210> SEQ ID NO 44
<211> LENGTH: 45
<212> TYPE: PRT
<213> ORGANISM: peptide

<400> SEQUENCE: 44

Asn Thr Cys Glu Asn Leu Ala Gly Ser Tyr Lys Gly Val Cys Phe Gly
1               5                  10                 15

Gly Cys Asp Arg His Cys Arg Thr Gln Glu Gly Ala Ile Ser Gly Arg
                    20                 25                 30

Cys Arg Asp Asp Phe Arg Cys Trp Cys Thr Lys Asn Cys
                    35                 40                 45

<210> SEQ ID NO 45
<211> LENGTH: 50
<212> TYPE: PRT
<213> ORGANISM: peptide
```

```
<400> SEQUENCE: 45

Leu Cys Asn Glu Arg Pro Ser Gln Thr Trp Ser Gly Asn Cys Gly Asn
1               5                   10                  15

Thr Ala His Cys Asp Lys Gln Cys Gln Asp Trp Glu Lys Ala Ser His
                20                  25                  30

Gly Ala Cys His Lys Arg Glu Asn His Trp Lys Cys Phe Cys Tyr Phe
            35                  40                  45

Asn Cys
    50

<210> SEQ ID NO 46
<211> LENGTH: 51
<212> TYPE: PRT
<213> ORGANISM: peptide

<400> SEQUENCE: 46

Lys Leu Cys Asp Val Pro Ser Gly Thr Trp Ser Gly His Cys Gly Ser
1               5                   10                  15

Ser Ser Lys Cys Ser Gln Gln Cys Lys Asp Arg Glu His Phe Ala Tyr
                20                  25                  30

Gly Gly Ala Cys His Tyr Gln Phe Pro Ser Val Lys Cys Phe Cys Lys
            35                  40                  45

Arg Gln Cys
    50

<210> SEQ ID NO 47
<211> LENGTH: 50
<212> TYPE: PRT
<213> ORGANISM: peptide

<400> SEQUENCE: 47

Glu Leu Cys Glu Lys Ala Ser Lys Thr Trp Ser Gly Asn Cys Gly Asn
1               5                   10                  15

Thr Gly His Cys Asp Asn Gln Cys Lys Ser Trp Glu Gly Ala Ala His
                20                  25                  30

Gly Ala Cys His Val Arg Asn Gly Lys His Met Cys Phe Cys Tyr Phe
            35                  40                  45

Asn Cys
    50

<210> SEQ ID NO 48
<211> LENGTH: 46
<212> TYPE: PRT
<213> ORGANISM: peptide

<400> SEQUENCE: 48

Asn Thr Cys Glu His Leu Ala Asp Thr Tyr Arg Gly Val Cys Phe Thr
1               5                   10                  15

Asn Ala Ser Cys Asp Asp His Cys Lys Asn Lys Ala His Leu Ile Ser
                20                  25                  30

Gly Thr Cys His Asp Trp Lys Cys Phe Cys Thr Gln Asn Cys
            35                  40                  45

<210> SEQ ID NO 49
<211> LENGTH: 49
<212> TYPE: PRT
<213> ORGANISM: peptide

<400> SEQUENCE: 49
```

```
Asn Leu Cys Glu Arg Ala Ser Leu Thr Trp Thr Gly Asn Cys Gly Asn
1               5                   10                  15

Thr Gly His Cys Asp Thr Gln Cys Arg Asn Trp Glu Ser Ala Lys His
                20                  25                  30

Gly Ala Cys His Lys Arg Gly Asn Trp Lys Cys Phe Cys Tyr Phe Asn
            35                  40                  45

Cys
```

<210> SEQ ID NO 50
<211> LENGTH: 79
<212> TYPE: PRT
<213> ORGANISM: peptide

<400> SEQUENCE: 50

```
Leu Phe Val Ala Tyr Glu Val Gln Ala Arg Glu Cys Ala Arg Glu Ile
1               5                   10                  15

Phe Thr Gly Leu Cys Ile Thr Asn Pro Gln Cys Arg Lys Ala Cys Ile
                20                  25                  30

Lys Glu Lys Phe Thr Asp Gly His Cys Ser Lys Ile Leu Arg Arg Cys
            35                  40                  45

Leu Cys Thr Lys Pro Cys Gly Ala Glu Thr Leu Ala Glu Glu Ala
    50                  55                  60

Thr Thr Leu Ala Ala Ala Leu Leu Glu Glu Glu Ile Met Asp Asn
65                  70                  75
```

<210> SEQ ID NO 51
<211> LENGTH: 105
<212> TYPE: PRT
<213> ORGANISM: peptide

<400> SEQUENCE: 51

```
Met Ala Arg Ser Val Cys Phe Met Ala Phe Ala Ile Leu Ala Val Met
1               5                   10                  15

Leu Phe Val Ala Tyr Asp Val Glu Ala Lys Asp Cys Lys Thr Glu Ser
                20                  25                  30

Asn Thr Phe Pro Gly Ile Cys Ile Thr Lys Pro Pro Cys Arg Lys Ala
            35                  40                  45

Cys Ile Lys Glu Lys Phe Thr Asp Gly His Cys Ser Lys Ile Leu Arg
    50                  55                  60

Arg Cys Leu Cys Thr Lys Pro Cys Val Phe Asp Glu Lys Met Ile Lys
65                  70                  75                  80

Thr Gly Ala Glu Thr Leu Ala Glu Glu Ala Thr Thr Leu Ala Ala Ala
                85                  90                  95

Leu Leu Glu Glu Glu Ile Met Asp Asn
            100                 105
```

<210> SEQ ID NO 52
<211> LENGTH: 106
<212> TYPE: PRT
<213> ORGANISM: peptide

<400> SEQUENCE: 52

```
Met Ala Arg Ser Leu Cys Phe Met Ala Phe Ala Val Leu Ala Met Met
1               5                   10                  15

Leu Phe Val Ala Tyr Glu Val Gln Ala Lys Ser Thr Cys Lys Ala Glu
                20                  25                  30

Ser Asn Thr Phe Pro Gly Leu Cys Ile Thr Lys Pro Pro Cys Arg Lys
            35                  40                  45
```

```
Ala Cys Leu Ser Glu Lys Phe Thr Asp Gly Lys Cys Ser Lys Ile Leu
         50                  55                  60

Arg Arg Cys Ile Cys Tyr Lys Pro Cys Val Phe Asp Gly Lys Met Ile
 65                  70                  75                  80

Gln Thr Gly Ala Glu Asn Leu Ala Glu Ala Glu Thr Leu Ala Ala
             85                  90                  95

Ala Leu Leu Glu Glu Glu Met Met Asp Asn
            100                 105

<210> SEQ ID NO 53
<211> LENGTH: 47
<212> TYPE: PRT
<213> ORGANISM: peptide

<400> SEQUENCE: 53

Arg Thr Cys Glu Ser Gln Ser His Arg Phe Lys Gly Pro Cys Ser Arg
 1               5                   10                  15

Asp Ser Asn Cys Ala Thr Val Cys Leu Thr Glu Gly Phe Ser Gly Gly
                 20                  25                  30

Arg Cys Pro Trp Ile Pro Pro Arg Cys Phe Cys Thr Ser Pro Cys
             35                  40                  45

<210> SEQ ID NO 54
<211> LENGTH: 19
<212> TYPE: PRT
<213> ORGANISM: peptide

<400> SEQUENCE: 54

Arg Thr Cys Glu Ser Gln Ser His Arg Phe His Gly Thr Cys Val Arg
 1               5                   10                  15

Glu Ser Asn

<210> SEQ ID NO 55
<211> LENGTH: 47
<212> TYPE: PRT
<213> ORGANISM: peptide

<400> SEQUENCE: 55

Arg Thr Cys Glu Ser Gln Ser His Arg Phe Lys Gly Thr Cys Val Ser
 1               5                   10                  15

Ala Ser Asn Cys Ala Asn Val Cys His Asn Glu Gly Phe Val Gly Gly
                 20                  25                  30

Asn Cys Arg Gly Phe Arg Arg Arg Cys Phe Cys Thr Arg His Cys
             35                  40                  45

<210> SEQ ID NO 56
<211> LENGTH: 1104
<212> TYPE: DNA
<213> ORGANISM: Nicotiana alata
<220> FEATURE:
<221> NAME/KEY: CDS
<222> LOCATION: (1)..(1104)

<400> SEQUENCE: 56 aag gct tgt acc tta aac tgt gat cca aga att gcc tat gga gtt tgc      48
Lys Ala Cys Thr Leu Asn Cys Asp Pro Arg Ile Ala Tyr Gly Val Cys
 1               5                   10                  15 ccg cgt tca gaa gaa aag aag aat gat cgg ata tgc acc aac tgt tgc      96
Pro Arg Ser Glu Glu Lys Lys Asn Asp Arg Ile Cys Thr Asn Cys Cys
                 20                  25                  30
```

```
gca ggc acg aag ggt tgt aag tac ttc agt gat gat gga act ttt gtt      144
Ala Gly Thr Lys Gly Cys Lys Tyr Phe Ser Asp Asp Gly Thr Phe Val
        35                  40                  45 tgt gaa gga gag tct gat cct aga aat cca aag gct tgt acc tta aac      192
Cys Glu Gly Glu Ser Asp Pro Arg Asn Pro Lys Ala Cys Thr Leu Asn
 50                  55                  60 tgt gat cca aga att gcc tat gga gtt tgc ccg cgt tca gaa gaa aag      240
Cys Asp Pro Arg Ile Ala Tyr Gly Val Cys Pro Arg Ser Glu Glu Lys
 65                  70                  75                  80 aag aat gat cgg ata tgc acc aac tgt tgc gca ggc acg aag ggt tgt      288
Lys Asn Asp Arg Ile Cys Thr Asn Cys Cys Ala Gly Thr Lys Gly Cys
                 85                  90                  95 aag tac ttc agt gat gat gga act ttt gtt tgt gaa gga gag tct gat      336
Lys Tyr Phe Ser Asp Asp Gly Thr Phe Val Cys Glu Gly Glu Ser Asp
            100                 105                 110 cct aga aat cca aag gct tgt cct cgg aat tgc gat cca aga att gcc      384
Pro Arg Asn Pro Lys Ala Cys Pro Arg Asn Cys Asp Pro Arg Ile Ala
        115                 120                 125 tat ggg att tgc cca ctt gca gaa gaa aag aag aat gat cgg ata tgc      432
Tyr Gly Ile Cys Pro Leu Ala Glu Glu Lys Lys Asn Asp Arg Ile Cys
130                 135                 140 acc aac tgt tgc gca ggc aaa aag ggt tgt aag tac ttt agt gat gat      480
Thr Asn Cys Cys Ala Gly Lys Lys Gly Cys Lys Tyr Phe Ser Asp Asp
145                 150                 155                 160 gga act ttt gtt tgt gaa gga gag tct gat cct aaa aat cca aag gcc      528
Gly Thr Phe Val Cys Glu Gly Glu Ser Asp Pro Lys Asn Pro Lys Ala
                165                 170                 175 tgt cct cgg aat tgt gat gga aga att gcc tat ggg att tgc cca ctt      576
Cys Pro Arg Asn Cys Asp Gly Arg Ile Ala Tyr Gly Ile Cys Pro Leu
            180                 185                 190 tca gaa gaa aag aag aat gat cgg ata tgc acc aac tgc tgc gca ggc      624
Ser Glu Glu Lys Lys Asn Asp Arg Ile Cys Thr Asn Cys Cys Ala Gly
        195                 200                 205 aaa aag ggt tgt aag tac ttt agt gat gat gga act ttt gtt tgt gaa      672
Lys Lys Gly Cys Lys Tyr Phe Ser Asp Asp Gly Thr Phe Val Cys Glu
210                 215                 220 gga gag tct gat cct aaa aat cca aag gct tgt cct cgg aat tgt gat      720
Gly Glu Ser Asp Pro Lys Asn Pro Lys Ala Cys Pro Arg Asn Cys Asp
225                 230                 235                 240 gga aga att gcc tat ggg att tgc cca ctt tca gaa gaa aag aag aat      768
Gly Arg Ile Ala Tyr Gly Ile Cys Pro Leu Ser Glu Glu Lys Lys Asn
                245                 250                 255 gat cgg ata tgc aca aac tgt tgc gca ggc aaa aag ggc tgt aag tac      816
Asp Arg Ile Cys Thr Asn Cys Cys Ala Gly Lys Lys Gly Cys Lys Tyr
            260                 265                 270 ttt agt gat gat gga act ttt gtt tgt gaa gga gag tct gat cct aga      864
Phe Ser Asp Asp Gly Thr Phe Val Cys Glu Gly Glu Ser Asp Pro Arg
        275                 280                 285 aat cca aag gcc tgt cct cgg aat tgt gat gga aga att gcc tat gga      912
Asn Pro Lys Ala Cys Pro Arg Asn Cys Asp Gly Arg Ile Ala Tyr Gly
290                 295                 300 att tgc cca ctt tca gaa gaa aag aag aat gat cgg ata tgc acc aat      960
Ile Cys Pro Leu Ser Glu Glu Lys Lys Asn Asp Arg Ile Cys Thr Asn
305                 310                 315                 320 tgt tgc gca ggc aag aag ggc tgt aag tac ttt agt gat gat gga act     1008
Cys Cys Ala Gly Lys Lys Gly Cys Lys Tyr Phe Ser Asp Asp Gly Thr
                325                 330                 335 ttt att tgt gaa gga gaa tct gaa tat gcc agc aaa gtg gat gaa tat     1056
Phe Ile Cys Glu Gly Glu Ser Glu Tyr Ala Ser Lys Val Asp Glu Tyr
            340                 345                 350
```

```
gtt ggt gaa gtg gag aat gat ctc cag aag tct aag gtt gct gtt tcc      1104
Val Gly Glu Val Glu Asn Asp Leu Gln Lys Ser Lys Val Ala Val Ser
    355                 360                 365
```

<210> SEQ ID NO 57
<211> LENGTH: 368
<212> TYPE: PRT
<213> ORGANISM: Nicotiana alata

<400> SEQUENCE: 57

```
Lys Ala Cys Thr Leu Asn Cys Asp Pro Arg Ile Ala Tyr Gly Val Cys
1               5                   10                  15

Pro Arg Ser Glu Glu Lys Lys Asn Asp Arg Ile Cys Thr Asn Cys Cys
            20                  25                  30

Ala Gly Thr Lys Gly Cys Lys Tyr Phe Ser Asp Asp Gly Thr Phe Val
        35                  40                  45

Cys Glu Gly Glu Ser Asp Pro Arg Asn Pro Lys Ala Cys Thr Leu Asn
50                  55                  60

Cys Asp Pro Arg Ile Ala Tyr Gly Val Cys Pro Arg Ser Glu Glu Lys
65                  70                  75                  80

Lys Asn Asp Arg Ile Cys Thr Asn Cys Cys Ala Gly Thr Lys Gly Cys
            85                  90                  95

Lys Tyr Phe Ser Asp Asp Gly Thr Phe Val Cys Glu Gly Glu Ser Asp
        100                 105                 110

Pro Arg Asn Pro Lys Ala Cys Pro Arg Asn Cys Asp Pro Arg Ile Ala
    115                 120                 125

Tyr Gly Ile Cys Pro Leu Ala Glu Glu Lys Lys Asn Asp Arg Ile Cys
130                 135                 140

Thr Asn Cys Cys Ala Gly Lys Lys Gly Cys Lys Tyr Phe Ser Asp Asp
145                 150                 155                 160

Gly Thr Phe Val Cys Glu Gly Glu Ser Asp Pro Lys Asn Pro Lys Ala
            165                 170                 175

Cys Pro Arg Asn Cys Asp Gly Arg Ile Ala Tyr Gly Ile Cys Pro Leu
        180                 185                 190

Ser Glu Glu Lys Lys Asn Asp Arg Ile Cys Thr Asn Cys Cys Ala Gly
    195                 200                 205

Lys Lys Gly Cys Lys Tyr Phe Ser Asp Asp Gly Thr Phe Val Cys Glu
210                 215                 220

Gly Glu Ser Asp Pro Lys Asn Pro Lys Ala Cys Pro Arg Asn Cys Asp
225                 230                 235                 240

Gly Arg Ile Ala Tyr Gly Ile Cys Pro Leu Ser Glu Glu Lys Lys Asn
            245                 250                 255

Asp Arg Ile Cys Thr Asn Cys Cys Ala Gly Lys Lys Gly Cys Lys Tyr
        260                 265                 270

Phe Ser Asp Asp Gly Thr Phe Val Cys Glu Gly Glu Ser Asp Pro Arg
    275                 280                 285

Asn Pro Lys Ala Cys Pro Arg Asn Cys Asp Gly Arg Ile Ala Tyr Gly
290                 295                 300

Ile Cys Pro Leu Ser Glu Glu Lys Lys Asn Asp Arg Ile Cys Thr Asn
305                 310                 315                 320

Cys Cys Ala Gly Lys Lys Gly Cys Lys Tyr Phe Ser Asp Asp Gly Thr
            325                 330                 335

Phe Ile Cys Glu Gly Glu Ser Glu Tyr Ala Ser Lys Val Asp Glu Tyr
        340                 345                 350
```

```
Val Gly Glu Val Glu Asn Asp Leu Gln Lys Ser Lys Val Ala Val Ser
    355                 360                 365
```

```
<210> SEQ ID NO 58
<211> LENGTH: 47
<212> TYPE: PRT
<213> ORGANISM: Nicotiana alata
<220> FEATURE:
<221> NAME/KEY: misc_feature
<222> LOCATION: (1)..(1)
<223> OTHER INFORMATION: X = R or Q
<220> FEATURE:
<221> NAME/KEY: misc_feature
<222> LOCATION: (2)..(2)
<223> OTHER INFORMATION: X = E or I or T
<220> FEATURE:
<221> NAME/KEY: misc_feature
<222> LOCATION: (4)..(4)
<223> OTHER INFORMATION: X = K or E
<220> FEATURE:
<221> NAME/KEY: misc_feature
<222> LOCATION: (5)..(5)
<223> OTHER INFORMATION: X = T or A or S
<220> FEATURE:
<221> NAME/KEY: misc_feature
<222> LOCATION: (6)..(6)
<223> OTHER INFORMATION: X = E or P or Q
<220> FEATURE:
<221> NAME/KEY: misc_feature
<222> LOCATION: (8)..(8)
<223> OTHER INFORMATION: X = N or Q or H
<220> FEATURE:
<221> NAME/KEY: misc_feature
<222> LOCATION: (9)..(9)
<223> OTHER INFORMATION: X = T or R
<220> FEATURE:
<221> NAME/KEY: misc_feature
<222> LOCATION: (11)..(11)
<223> OTHER INFORMATION: X = P or K or H
<220> FEATURE:
<221> NAME/KEY: misc_feature
<222> LOCATION: (13)..(13)
<223> OTHER INFORMATION: X = I or L or P or T
<220> FEATURE:
<221> NAME/KEY: misc_feature
<222> LOCATION: (15)..(15)
<223> OTHER INFORMATION: X = I or F or S or V
<220> FEATURE:
<221> NAME/KEY: misc_feature
<222> LOCATION: (16)..(16)
<223> OTHER INFORMATION: X = T or M or R or S
<220> FEATURE:
<221> NAME/KEY: misc_feature
<222> LOCATION: (17)..(17)
<223> OTHER INFORMATION: X = K or D or E or A
<220> FEATURE:
<221> NAME/KEY: misc_feature
<222> LOCATION: (18)..(18)
<223> OTHER INFORMATION: X = P or S
<220> FEATURE:
<221> NAME/KEY: misc_feature
<222> LOCATION: (19)..(19)
<223> OTHER INFORMATION: X = P or S or N
<220> FEATURE:
<221> NAME/KEY: misc_feature
<222> LOCATION: (21)..(21)
<223> OTHER INFORMATION: X = R or A
<220> FEATURE:
<221> NAME/KEY: misc_feature
<222> LOCATION: (22)..(22)
<223> OTHER INFORMATION: X = K or T or S or N
<220> FEATURE:
<221> NAME/KEY: misc_feature
<222> LOCATION: (23)..(23)
<223> OTHER INFORMATION: X = A or Y or V
<220> FEATURE:
<221> NAME/KEY: misc_feature
<222> LOCATION: (25)..(25)
```

```
<223> OTHER INFORMATION: X = I or L or Q or H
<220> FEATURE:
<221> NAME/KEY: misc_feature
<222> LOCATION: (26)..(26)
<223> OTHER INFORMATION: X = S or K or T or N
<220> FEATURE:
<221> NAME/KEY: misc_feature
<222> LOCATION: (28)..(28)
<223> OTHER INFORMATION: X = K or G
<220> FEATURE:
<221> NAME/KEY: misc_feature
<222> LOCATION: (30)..(30)
<223> OTHER INFORMATION: X = T or S or I or V
<220> FEATURE:
<221> NAME/KEY: misc_feature
<222> LOCATION: (31)..(31)
<223> OTHER INFORMATION: X = D or G
<220> FEATURE:
<221> NAME/KEY: misc_feature
<222> LOCATION: (33)..(33)
<223> OTHER INFORMATION: X = H or R or N
<220> FEATURE:
<221> NAME/KEY: misc_feature
<222> LOCATION: (35)..(35)
<223> OTHER INFORMATION: X = S or P or R
<220> FEATURE:
<221> NAME/KEY: misc_feature
<222> LOCATION: (36)..(36)
<223> OTHER INFORMATION: X = K or W or A or G
<220> FEATURE:
<221> NAME/KEY: misc_feature
<222> LOCATION: (37)..(37)
<223> OTHER INFORMATION: X = I or L or F
<220> FEATURE:
<221> NAME/KEY: misc_feature
<222> LOCATION: (38)..(38)
<223> OTHER INFORMATION: X = L or Q or P or R
<220> FEATURE:
<221> NAME/KEY: misc_feature
<222> LOCATION: (39)..(39)
<223> OTHER INFORMATION: X = R or P
<220> FEATURE:
<221> NAME/KEY: misc_feature
<222> LOCATION: (40)..(40)
<223> OTHER INFORMATION: X = R or K
<220> FEATURE:
<221> NAME/KEY: misc_feature
<222> LOCATION: (42)..(42)
<223> OTHER INFORMATION: X = L or F
<220> FEATURE:
<221> NAME/KEY: misc_feature
<222> LOCATION: (45)..(45)
<223> OTHER INFORMATION: X = K or S or R

<400> SEQUENCE: 58

Xaa Xaa Cys Xaa Xaa Xaa Ser Xaa Xaa Phe Xaa Gly Xaa Cys Xaa Xaa
1               5                   10                  15

Xaa Xaa Xaa Cys Xaa Xaa Xaa Cys Xaa Xaa Glu Xaa Phe Xaa Xaa Gly
            20                  25                  30

Xaa Cys Xaa Xaa Xaa Xaa Xaa Xaa Cys Xaa Cys Thr Xaa Xaa Cys
        35                  40                  45

<210> SEQ ID NO 59
<211> LENGTH: 32
<212> TYPE: PRT
<213> ORGANISM: Nicotiana alata
<220> FEATURE:
<221> NAME/KEY: misc_feature
<222> LOCATION: (2)..(2)
<223> OTHER INFORMATION: X = A or G or K
<220> FEATURE:
<221> NAME/KEY: misc_feature
<222> LOCATION: (3)..(3)
<223> OTHER INFORMATION: X = R or N or L
<220> FEATURE:
```

```
<221> NAME/KEY: misc_feature
<222> LOCATION: (5)..(5)
<223> OTHER INFORMATION: X = L or I or M
<220> FEATURE:
<221> NAME/KEY: misc_feature
<222> LOCATION: (6)..(6)
<223> OTHER INFORMATION: X = C or F or R
<220> FEATURE:
<221> NAME/KEY: misc_feature
<222> LOCATION: (7)..(7)
<223> OTHER INFORMATION: X = F or L
<220> FEATURE:
<221> NAME/KEY: misc_feature
<222> LOCATION: (8)..(8)
<223> OTHER INFORMATION: X = M or F or I
<220> FEATURE:
<221> NAME/KEY: misc_feature
<222> LOCATION: (9)..(9)
<223> OTHER INFORMATION: X = A or S
<220> FEATURE:
<221> NAME/KEY: misc_feature
<222> LOCATION: (10)..(10)
<223> OTHER INFORMATION: X = F or T or A
<220> FEATURE:
<221> NAME/KEY: misc_feature
<222> LOCATION: (11)..(11)
<223> OTHER INFORMATION: X = A or L or V or F
<220> FEATURE:
<221> NAME/KEY: misc_feature
<222> LOCATION: (12)..(12)
<223> OTHER INFORMATION: X = I or V or L or F
<220> FEATURE:
<221> NAME/KEY: misc_feature
<222> LOCATION: (13)..(13)
<223> OTHER INFORMATION: X = L or I
<220> FEATURE:
<221> NAME/KEY: misc_feature
<222> LOCATION: (14)..(14)
<223> OTHER INFORMATION: X = A or I or M
<220> FEATURE:
<221> NAME/KEY: misc_feature
<222> LOCATION: (15)..(15)
<223> OTHER INFORMATION: X = M or A or F
<220> FEATURE:
<221> NAME/KEY: misc_feature
<222> LOCATION: (16)..(16)
<223> OTHER INFORMATION: X = M or L
<220> FEATURE:
<221> NAME/KEY: misc_feature
<222> LOCATION: (17)..(17)
<223> OTHER INFORMATION: X = L or I
<220> FEATURE:
<221> NAME/KEY: misc_feature
<222> LOCATION: (18)..(18)
<223> OTHER INFORMATION: X = F or V
<220> FEATURE:
<221> NAME/KEY: misc_feature
<222> LOCATION: (19)..(19)
<223> OTHER INFORMATION: X = V or T or L
<220> FEATURE:
<221> NAME/KEY: misc_feature
<222> LOCATION: (20)..(20)
<223> OTHER INFORMATION: X = A or T or S
<220> FEATURE:
<221> NAME/KEY: misc_feature
<222> LOCATION: (21)..(21)
<223> OTHER INFORMATION: X = Y or T
<220> FEATURE:
<221> NAME/KEY: misc_feature
<222> LOCATION: (22)..(22)
<223> OTHER INFORMATION: X = E or G
<220> FEATURE:
<221> NAME/KEY: misc_feature
<222> LOCATION: (23)..(23)
<223> OTHER INFORMATION: X = V or M
<220> FEATURE:
<221> NAME/KEY: misc_feature
<222> LOCATION: (24)..(24)
<223> OTHER INFORMATION: X = no amino acid or G
```

```
<220> FEATURE:
<221> NAME/KEY: misc_feature
<222> LOCATION: (25)..(25)
<223> OTHER INFORMATION: X = no amino acid or P
<220> FEATURE:
<221> NAME/KEY: misc_feature
<222> LOCATION: (26)..(26)
<223> OTHER INFORMATION: X = no amino acid or M or V
<220> FEATURE:
<221> NAME/KEY: misc_feature
<222> LOCATION: (27)..(27)
<223> OTHER INFORMATION: X = no amino acid or T
<220> FEATURE:
<221> NAME/KEY: misc_feature
<222> LOCATION: (28)..(28)
<223> OTHER INFORMATION: X = no amino acid or I or S
<220> FEATURE:
<221> NAME/KEY: misc_feature
<222> LOCATION: (29)..(29)
<223> OTHER INFORMATION: X = no amino acid or A or V
<220> FEATURE:
<221> NAME/KEY: misc_feature
<222> LOCATION: (30)..(30)
<223> OTHER INFORMATION: X = Q or E
<220> FEATURE:
<221> NAME/KEY: misc_feature
<222> LOCATION: (32)..(32)
<223> OTHER INFORMATION: X = no amino acid or Q

<400> SEQUENCE: 59

Met Xaa Xaa Ser Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Ala Xaa
            20                  25                  30

<210> SEQ ID NO 60
<211> LENGTH: 33
<212> TYPE: PRT
<213> ORGANISM: Nicotiana alata
<220> FEATURE:
<221> NAME/KEY: misc_feature
<222> LOCATION: (1)..(1)
<223> OTHER INFORMATION: X = no amino acid or V
<220> FEATURE:
<221> NAME/KEY: misc_feature
<222> LOCATION: (2)..(2)
<223> OTHER INFORMATION: X = no amino acid or F
<220> FEATURE:
<221> NAME/KEY: misc_feature
<222> LOCATION: (3)..(3)
<223> OTHER INFORMATION: X = no amino acid or D
<220> FEATURE:
<221> NAME/KEY: misc_feature
<222> LOCATION: (4)..(4)
<223> OTHER INFORMATION: X = no amino acid or E or K
<220> FEATURE:
<221> NAME/KEY: misc_feature
<222> LOCATION: (5)..(5)
<223> OTHER INFORMATION: X = no amino acid or K or I
<220> FEATURE:
<221> NAME/KEY: misc_feature
<222> LOCATION: (6)..(6)
<223> OTHER INFORMATION: X = no amino acid or M or S
<220> FEATURE:
<221> NAME/KEY: misc_feature
<222> LOCATION: (7)..(7)
<223> OTHER INFORMATION: X = no amino acid or T or I or S
<220> FEATURE:
<221> NAME/KEY: misc_feature
<222> LOCATION: (8)..(8)
<223> OTHER INFORMATION: X = no amino acid or K or E
<220> FEATURE:
<221> NAME/KEY: misc_feature
<222> LOCATION: (9)..(9)
<223> OTHER INFORMATION: X = no amino acid or T or V
<220> FEATURE:
```

```
<221> NAME/KEY: misc_feature
<222> LOCATION: (10)..(10)
<223> OTHER INFORMATION: X = no amino acid or G or K
<220> FEATURE:
<221> NAME/KEY: misc_feature
<222> LOCATION: (11)..(11)
<223> OTHER INFORMATION: X = no amino acid or A
<220> FEATURE:
<221> NAME/KEY: misc_feature
<222> LOCATION: (12)..(12)
<223> OTHER INFORMATION: X = no amino acid or E
<220> FEATURE:
<221> NAME/KEY: misc_feature
<222> LOCATION: (13)..(13)
<223> OTHER INFORMATION: X = no amino acid or I or T
<220> FEATURE:
<221> NAME/KEY: misc_feature
<222> LOCATION: (14)..(14)
<223> OTHER INFORMATION: X = no amino acid or L
<220> FEATURE:
<221> NAME/KEY: misc_feature
<222> LOCATION: (15)..(15)
<223> OTHER INFORMATION: X = no amino acid or A or V or G
<220> FEATURE:
<221> NAME/KEY: misc_feature
<222> LOCATION: (16)..(16)
<223> OTHER INFORMATION: X = no amino acid or E
<220> FEATURE:
<221> NAME/KEY: misc_feature
<222> LOCATION: (17)..(17)
<223> OTHER INFORMATION: X = no amino acid or E
<220> FEATURE:
<221> NAME/KEY: misc_feature
<222> LOCATION: (18)..(18)
<223> OTHER INFORMATION: X = no amino acid or A
<220> FEATURE:
<221> NAME/KEY: misc_feature
<222> LOCATION: (19)..(19)
<223> OTHER INFORMATION: X = no amino acid or K
<220> FEATURE:
<221> NAME/KEY: misc_feature
<222> LOCATION: (20)..(20)
<223> OTHER INFORMATION: X = no amino acid or T
<220> FEATURE:
<221> NAME/KEY: misc_feature
<222> LOCATION: (21)..(21)
<223> OTHER INFORMATION: X = no amino acid or L
<220> FEATURE:
<221> NAME/KEY: misc_feature
<222> LOCATION: (22)..(22)
<223> OTHER INFORMATION: X = no amino acid or A or S
<220> FEATURE:
<221> NAME/KEY: misc_feature
<222> LOCATION: (23)..(23)
<223> OTHER INFORMATION: X = no amino acid or A or E
<220> FEATURE:
<221> NAME/KEY: misc_feature
<222> LOCATION: (24)..(24)
<223> OTHER INFORMATION: X = no amino acid or A or V
<220> FEATURE:
<221> NAME/KEY: misc_feature
<222> LOCATION: (25)..(25)
<223> OTHER INFORMATION: X = no amino acid or L or V
<220> FEATURE:
<221> NAME/KEY: misc_feature
<222> LOCATION: (26)..(26)
<223> OTHER INFORMATION: X = no amino acid or L
<220> FEATURE:
<221> NAME/KEY: misc_feature
<222> LOCATION: (27)..(27)
<223> OTHER INFORMATION: X = no amino acid or E
<220> FEATURE:
<221> NAME/KEY: misc_feature
<222> LOCATION: (28)..(28)
<223> OTHER INFORMATION: X = no amino acid or E
<220> FEATURE:
<221> NAME/KEY: misc_feature
<222> LOCATION: (29)..(29)
<223> OTHER INFORMATION: X = no amino acid or E
```

```
<220> FEATURE:
<221> NAME/KEY: misc_feature
<222> LOCATION: (30)..(30)
<223> OTHER INFORMATION: X = no amino acid or I
<220> FEATURE:
<221> NAME/KEY: misc_feature
<222> LOCATION: (31)..(31)
<223> OTHER INFORMATION: X = no amino acid or M
<220> FEATURE:
<221> NAME/KEY: misc_feature
<222> LOCATION: (32)..(32)
<223> OTHER INFORMATION: X = no amino acid or D or M
<220> FEATURE:
<221> NAME/KEY: misc_feature
<222> LOCATION: (33)..(33)
<223> OTHER INFORMATION: X = no amino acid or N or E

<400> SEQUENCE: 60

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa

<210> SEQ ID NO 61
<211> LENGTH: 112
<212> TYPE: PRT
<213> ORGANISM: Nicotiana alata
<220> FEATURE:
<221> NAME/KEY: misc_feature
<222> LOCATION: (2)..(2)
<223> OTHER INFORMATION: X = A or G or K
<220> FEATURE:
<221> NAME/KEY: misc_feature
<222> LOCATION: (3)..(3)
<223> OTHER INFORMATION: X = R or N or L
<220> FEATURE:
<221> NAME/KEY: misc_feature
<222> LOCATION: (5)..(5)
<223> OTHER INFORMATION: X = L or I or M
<220> FEATURE:
<221> NAME/KEY: misc_feature
<222> LOCATION: (6)..(6)
<223> OTHER INFORMATION: X = C or F or R
<220> FEATURE:
<221> NAME/KEY: misc_feature
<222> LOCATION: (7)..(7)
<223> OTHER INFORMATION: X = F or L
<220> FEATURE:
<221> NAME/KEY: misc_feature
<222> LOCATION: (8)..(8)
<223> OTHER INFORMATION: X = M or F or I
<220> FEATURE:
<221> NAME/KEY: misc_feature
<222> LOCATION: (9)..(9)
<223> OTHER INFORMATION: X =  A or S
<220> FEATURE:
<221> NAME/KEY: misc_feature
<222> LOCATION: (10)..(10)
<223> OTHER INFORMATION: X =  F or T or A
<220> FEATURE:
<221> NAME/KEY: misc_feature
<222> LOCATION: (11)..(11)
<223> OTHER INFORMATION: X =  A or L or V or F
<220> FEATURE:
<221> NAME/KEY: misc_feature
<222> LOCATION: (12)..(12)
<223> OTHER INFORMATION: X =  I or V or L or F
<220> FEATURE:
<221> NAME/KEY: misc_feature
<222> LOCATION: (13)..(13)
<223> OTHER INFORMATION: X = L or I
<220> FEATURE:
<221> NAME/KEY: misc_feature
<222> LOCATION: (14)..(14)
```

```
<223> OTHER INFORMATION: X = A or I or M
<220> FEATURE:
<221> NAME/KEY: misc_feature
<222> LOCATION: (15)..(15)
<223> OTHER INFORMATION: X = M or A or F
<220> FEATURE:
<221> NAME/KEY: misc_feature
<222> LOCATION: (16)..(16)
<223> OTHER INFORMATION: X = M or L
<220> FEATURE:
<221> NAME/KEY: misc_feature
<222> LOCATION: (17)..(17)
<223> OTHER INFORMATION: X = L or I
<220> FEATURE:
<221> NAME/KEY: misc_feature
<222> LOCATION: (18)..(18)
<223> OTHER INFORMATION: X = F or V
<220> FEATURE:
<221> NAME/KEY: misc_feature
<222> LOCATION: (19)..(19)
<223> OTHER INFORMATION: X = V or T or L
<220> FEATURE:
<221> NAME/KEY: misc_feature
<222> LOCATION: (20)..(20)
<223> OTHER INFORMATION: X = A or T or S
<220> FEATURE:
<221> NAME/KEY: misc_feature
<222> LOCATION: (21)..(21)
<223> OTHER INFORMATION: X = Y or T
<220> FEATURE:
<221> NAME/KEY: misc_feature
<222> LOCATION: (22)..(22)
<223> OTHER INFORMATION: X = E or G
<220> FEATURE:
<221> NAME/KEY: misc_feature
<222> LOCATION: (23)..(23)
<223> OTHER INFORMATION: X = V or M
<220> FEATURE:
<221> NAME/KEY: misc_feature
<222> LOCATION: (24)..(24)
<223> OTHER INFORMATION: X = no amino acid or G
<220> FEATURE:
<221> NAME/KEY: misc_feature
<222> LOCATION: (25)..(25)
<223> OTHER INFORMATION: X = no amino acid or P
<220> FEATURE:
<221> NAME/KEY: misc_feature
<222> LOCATION: (26)..(26)
<223> OTHER INFORMATION: X = no amino acid or M or V
<220> FEATURE:
<221> NAME/KEY: misc_feature
<222> LOCATION: (27)..(27)
<223> OTHER INFORMATION: X = no amino acid or T
<220> FEATURE:
<221> NAME/KEY: misc_feature
<222> LOCATION: (28)..(28)
<223> OTHER INFORMATION: X = no amino acid or I or S
<220> FEATURE:
<221> NAME/KEY: misc_feature
<222> LOCATION: (29)..(29)
<223> OTHER INFORMATION: X = no amino acid or A or V
<220> FEATURE:
<221> NAME/KEY: misc_feature
<222> LOCATION: (30)..(30)
<223> OTHER INFORMATION: X = Q or E
<220> FEATURE:
<221> NAME/KEY: misc_feature
<222> LOCATION: (32)..(32)
<223> OTHER INFORMATION: X = no amino acid or Q
<220> FEATURE:
<221> NAME/KEY: misc_feature
<222> LOCATION: (33)..(33)
<223> OTHER INFORMATION: X = R or Q
<220> FEATURE:
<221> NAME/KEY: misc_feature
<222> LOCATION: (34)..(34)
<223> OTHER INFORMATION: X = E or I or T
<220> FEATURE:
<221> NAME/KEY: misc_feature
```

-continued

```
<222> LOCATION: (36)..(36)
<223> OTHER INFORMATION: X = K or E
<220> FEATURE:
<221> NAME/KEY: misc_feature
<222> LOCATION: (37)..(37)
<223> OTHER INFORMATION: X = T or A or S
<220> FEATURE:
<221> NAME/KEY: misc_feature
<222> LOCATION: (38)..(38)
<223> OTHER INFORMATION: X = E or P or Q
<220> FEATURE:
<221> NAME/KEY: misc_feature
<222> LOCATION: (40)..(40)
<223> OTHER INFORMATION: X = N or Q or H
<220> FEATURE:
<221> NAME/KEY: misc_feature
<222> LOCATION: (41)..(41)
<223> OTHER INFORMATION: X = T or R
<220> FEATURE:
<221> NAME/KEY: misc_feature
<222> LOCATION: (43)..(43)
<223> OTHER INFORMATION: X = P or K or H
<220> FEATURE:
<221> NAME/KEY: misc_feature
<222> LOCATION: (45)..(45)
<223> OTHER INFORMATION: X = I or L or P or T
<220> FEATURE:
<221> NAME/KEY: misc_feature
<222> LOCATION: (47)..(47)
<223> OTHER INFORMATION: X = I or F or S or V
<220> FEATURE:
<221> NAME/KEY: misc_feature
<222> LOCATION: (48)..(48)
<223> OTHER INFORMATION: X = T or M or R or S
<220> FEATURE:
<221> NAME/KEY: misc_feature
<222> LOCATION: (49)..(49)
<223> OTHER INFORMATION: X = K or D or E or A
<220> FEATURE:
<221> NAME/KEY: misc_feature
<222> LOCATION: (50)..(50)
<223> OTHER INFORMATION: X = P or S
<220> FEATURE:
<221> NAME/KEY: misc_feature
<222> LOCATION: (51)..(51)
<223> OTHER INFORMATION: X = P or S or N
<220> FEATURE:
<221> NAME/KEY: misc_feature
<222> LOCATION: (53)..(53)
<223> OTHER INFORMATION: X = R or A
<220> FEATURE:
<221> NAME/KEY: misc_feature
<222> LOCATION: (54)..(54)
<223> OTHER INFORMATION: X = K or T or S or N
<220> FEATURE:
<221> NAME/KEY: misc_feature
<222> LOCATION: (55)..(55)
<223> OTHER INFORMATION: X = A or Y or V
<220> FEATURE:
<221> NAME/KEY: misc_feature
<222> LOCATION: (57)..(57)
<223> OTHER INFORMATION: X = I or L or Q or H
<220> FEATURE:
<221> NAME/KEY: misc_feature
<222> LOCATION: (58)..(58)
<223> OTHER INFORMATION: X = S or K or T or N
<220> FEATURE:
<221> NAME/KEY: misc_feature
<222> LOCATION: (60)..(60)
<223> OTHER INFORMATION: X = K or G
<220> FEATURE:
<221> NAME/KEY: misc_feature
<222> LOCATION: (62)..(62)
<223> OTHER INFORMATION: X = T  or S or I or V
<220> FEATURE:
<221> NAME/KEY: misc_feature
<222> LOCATION: (63)..(63)
<223> OTHER INFORMATION: X = D or G
<220> FEATURE:
```

```
<221> NAME/KEY: misc_feature
<222> LOCATION: (65)..(65)
<223> OTHER INFORMATION: X = H or R or N
<220> FEATURE:
<221> NAME/KEY: misc_feature
<222> LOCATION: (67)..(67)
<223> OTHER INFORMATION: X = S or P or R
<220> FEATURE:
<221> NAME/KEY: misc_feature
<222> LOCATION: (68)..(68)
<223> OTHER INFORMATION: X = K or W or A or G
<220> FEATURE:
<221> NAME/KEY: misc_feature
<222> LOCATION: (69)..(69)
<223> OTHER INFORMATION: X = I or L or F
<220> FEATURE:
<221> NAME/KEY: misc_feature
<222> LOCATION: (70)..(70)
<223> OTHER INFORMATION: X = L or Q or P or R
<220> FEATURE:
<221> NAME/KEY: misc_feature
<222> LOCATION: (71)..(71)
<223> OTHER INFORMATION: X = R or P
<220> FEATURE:
<221> NAME/KEY: misc_feature
<222> LOCATION: (72)..(72)
<223> OTHER INFORMATION: X = R or K
<220> FEATURE:
<221> NAME/KEY: misc_feature
<222> LOCATION: (74)..(74)
<223> OTHER INFORMATION: X = L or F
<220> FEATURE:
<221> NAME/KEY: misc_feature
<222> LOCATION: (77)..(77)
<223> OTHER INFORMATION: X = K or S or R
<220> FEATURE:
<221> NAME/KEY: misc_feature
<222> LOCATION: (78)..(78)
<223> OTHER INFORMATION: X = P or N or H
<220> FEATURE:
<221> NAME/KEY: misc_feature
<222> LOCATION: (80)..(80)
<223> OTHER INFORMATION: X = no amino acid or V
<220> FEATURE:
<221> NAME/KEY: misc_feature
<222> LOCATION: (81)..(81)
<223> OTHER INFORMATION: X = no amino acid or F
<220> FEATURE:
<221> NAME/KEY: misc_feature
<222> LOCATION: (82)..(82)
<223> OTHER INFORMATION: X = no amino acid or D
<220> FEATURE:
<221> NAME/KEY: misc_feature
<222> LOCATION: (83)..(83)
<223> OTHER INFORMATION: X = no amino acid or E or K
<220> FEATURE:
<221> NAME/KEY: misc_feature
<222> LOCATION: (84)..(84)
<223> OTHER INFORMATION: X = no amino acid or K or I
<220> FEATURE:
<221> NAME/KEY: misc_feature
<222> LOCATION: (85)..(85)
<223> OTHER INFORMATION: X = no amino acid or M or S
<220> FEATURE:
<221> NAME/KEY: misc_feature
<222> LOCATION: (86)..(86)
<223> OTHER INFORMATION: X = no amino acid or T or I or S
<220> FEATURE:
<221> NAME/KEY: misc_feature
<222> LOCATION: (87)..(87)
<223> OTHER INFORMATION: X = no amino acid or K or E
<220> FEATURE:
<221> NAME/KEY: misc_feature
<222> LOCATION: (88)..(88)
<223> OTHER INFORMATION: X = no amino acid or T or V
<220> FEATURE:
<221> NAME/KEY: misc_feature
<222> LOCATION: (89)..(89)
<223> OTHER INFORMATION: X = no amino acid or G or K
```

-continued

```
<220> FEATURE:
<221> NAME/KEY: misc_feature
<222> LOCATION: (90)..(90)
<223> OTHER INFORMATION: X = no amino acid or A
<220> FEATURE:
<221> NAME/KEY: misc_feature
<222> LOCATION: (91)..(91)
<223> OTHER INFORMATION: X = no amino acid or E
<220> FEATURE:
<221> NAME/KEY: misc_feature
<222> LOCATION: (92)..(92)
<223> OTHER INFORMATION: X = no amino acid or I or T
<220> FEATURE:
<221> NAME/KEY: misc_feature
<222> LOCATION: (93)..(93)
<223> OTHER INFORMATION: X = no amino acid or L
<220> FEATURE:
<221> NAME/KEY: misc_feature
<222> LOCATION: (94)..(94)
<223> OTHER INFORMATION: X = no amino acid or A or V or G
<220> FEATURE:
<221> NAME/KEY: misc_feature
<222> LOCATION: (95)..(95)
<223> OTHER INFORMATION: X = no amino acid or E
<220> FEATURE:
<221> NAME/KEY: misc_feature
<222> LOCATION: (96)..(96)
<223> OTHER INFORMATION: X = no amino acid or E
<220> FEATURE:
<221> NAME/KEY: misc_feature
<222> LOCATION: (97)..(97)
<223> OTHER INFORMATION: X = no amino acid or A
<220> FEATURE:
<221> NAME/KEY: misc_feature
<222> LOCATION: (98)..(98)
<223> OTHER INFORMATION: X = no amino acid or K
<220> FEATURE:
<221> NAME/KEY: misc_feature
<222> LOCATION: (99)..(99)
<223> OTHER INFORMATION: X = no amino acid or T
<220> FEATURE:
<221> NAME/KEY: misc_feature
<222> LOCATION: (100)..(100)
<223> OTHER INFORMATION: X = no amino acid or L
<220> FEATURE:
<221> NAME/KEY: misc_feature
<222> LOCATION: (101)..(101)
<223> OTHER INFORMATION: X = no amino acid or A or S
<220> FEATURE:
<221> NAME/KEY: misc_feature
<222> LOCATION: (102)..(102)
<223> OTHER INFORMATION: X = no amino acid or A or E
<220> FEATURE:
<221> NAME/KEY: misc_feature
<222> LOCATION: (103)..(103)
<223> OTHER INFORMATION: X = no amino acid or A or V
<220> FEATURE:
<221> NAME/KEY: misc_feature
<222> LOCATION: (104)..(104)
<223> OTHER INFORMATION: X = no amino acid or L or V
<220> FEATURE:
<221> NAME/KEY: misc_feature
<222> LOCATION: (105)..(105)
<223> OTHER INFORMATION: X = no amino acid or L
<220> FEATURE:
<221> NAME/KEY: misc_feature
<222> LOCATION: (106)..(106)
<223> OTHER INFORMATION: X = no amino acid or E
<220> FEATURE:
<221> NAME/KEY: misc_feature
<222> LOCATION: (107)..(107)
<223> OTHER INFORMATION: X = no amino acid or E
<220> FEATURE:
<221> NAME/KEY: misc_feature
<222> LOCATION: (108)..(108)
<223> OTHER INFORMATION: X = no amino acid or E
<220> FEATURE:
<221> NAME/KEY: misc_feature
<222> LOCATION: (109)..(109)
```

```
<223> OTHER INFORMATION: X = no amino acid or I
<220> FEATURE:
<221> NAME/KEY: misc_feature
<222> LOCATION: (110)..(110)
<223> OTHER INFORMATION: X = no amino acid or M
<220> FEATURE:
<221> NAME/KEY: misc_feature
<222> LOCATION: (111)..(111)
<223> OTHER INFORMATION: X = no amino acid or D or M
<220> FEATURE:
<221> NAME/KEY: misc_feature
<222> LOCATION: (112)..(112)
<223> OTHER INFORMATION: X = no amino acid or N or E

<400> SEQUENCE: 61

Met Xaa Xaa Ser Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Ala Xaa
            20                  25                  30

Xaa Xaa Cys Xaa Xaa Xaa Ser Xaa Xaa Phe Xaa Gly Xaa Cys Xaa Xaa
        35                  40                  45

Xaa Xaa Xaa Cys Xaa Xaa Xaa Cys Xaa Xaa Glu Xaa Phe Xaa Xaa Gly
    50                  55                  60

Xaa Cys Xaa Xaa Xaa Xaa Xaa Cys Xaa Cys Thr Xaa Xaa Cys Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

<210> SEQ ID NO 62
<211> LENGTH: 47
<212> TYPE: PRT
<213> ORGANISM: Peptide
<220> FEATURE:
<221> NAME/KEY: misc_feature
<222> LOCATION: (1)..(46)
<223> OTHER INFORMATION: X is any amino acid. X is depicted as a in the
      text.

<400> SEQUENCE: 62

Xaa Xaa Cys Xaa Xaa Xaa Xaa Xaa Xaa Xaa Xaa Xaa Xaa Cys Xaa Xaa
1               5                   10                  15

Xaa Xaa Xaa Cys Xaa Xaa Xaa Cys Xaa Xaa Xaa Xaa Xaa Xaa Xaa
            20                  25                  30

Xaa Cys Xaa Xaa Xaa Xaa Xaa Xaa Cys Xaa Cys Xaa Xaa Xaa Cys
        35                  40                  45
```

We claim:

1. A genetic construct comprising a nucleotide sequence encoding a defensin wherein the defensin consists of the amino acid sequence of SEQ ID NO:8.

2. The genetic construct of claim 1 comprising the nucleotide sequence of SEQ ID NO:7.

3. The genetic construct of claim 1, wherein the nucleotide sequence encoding the defensin further encodes the amino acid sequence of SEQ ID NO:10 and/or SEQ ID NO:12.

4. The genetic construct of claim 1, wherein the nucleotide sequence encoding the defensin encodes the amino acid sequence set forth in SEQ ID NO:14, SEQ ID NO:16 or SEQ ID NO:18.

5. The genetic construct of claim 2, further comprising the nucleotide sequence of SEQ ID NO:9 and/or SEQ ID NO:11.

6. The genetic construct of claim 1, wherein the nucleotide sequence comprises SEQ ID NO:13, SEQ ID NO:15 or SEQ ID NO:17.

7. A transgenic plant comprising a genetic construct of claim 1.

8. The transgenic plant of claim 7, which is a monocotyledonous plant.

9. The transgenic plant of claim 7, which is a dicotyledonous plant.

10. The transgenic plant of claim 7, which is selected from the group consisting of wheat, rice, barley, soybean and sugarcane.

11. The transgenic plant of claim 7, which is selected from the group consisting of rose, carnation, petunia, lisianthus, lily, iris, tulip, freesia, delphinium, limorium and pelagonium.

12. A transgenic plant comprising the genetic construct of claim 3.

13. The transgenic plant of claim 12, which is a monocotyledonous plant.

14. The transgenic plant of claim 12, which is a dicotyledonous plant.

15. The transgenic plant of claim 12, which is selected from the group consisting of wheat, rice, barley, soybean and sugarcane.

16. The transgenic plant of claim 12, which is selected from the group consisting of rose, carnation, petunia, lisianthus, lily, iris, tulip, freesia, delphinium, limorium and pelagonium.

* * * * *